US010517564B2

(12) United States Patent
Konofagou et al.

(10) Patent No.: US 10,517,564 B2
(45) Date of Patent: Dec. 31, 2019

(54) SYSTEMS AND METHODS FOR MECHANICAL MAPPING OF CARDIAC RHYTHM

(71) Applicant: The Trustees of Columbia University in the City of New York, New York, NY (US)

(72) Inventors: Elisa E. Konofagou, New York, NY (US); Jean Provost, Paris (FR); Alok Gambhir, New York, NY (US); Alexandre Costet, New York, NY (US); Elaine Wan, Fresh Meadows, NY (US); Julien Grondin, Saint-Philippe (FR)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 262 days.

(21) Appl. No.: 14/682,980

(22) Filed: Apr. 9, 2015

(65) Prior Publication Data

US 2015/0289840 A1  Oct. 15, 2015

Related U.S. Application Data

(63) Continuation-in-part of application No. PCT/US2013/064377, filed on Oct. 10, 2013.
(Continued)

(51) Int. Cl.
*A61B 8/08* (2006.01)
*A61B 5/11* (2006.01)
(Continued)

(52) U.S. Cl.
CPC .......... *A61B 8/0883* (2013.01); *A61B 5/1102* (2013.01); *A61B 8/02* (2013.01);
(Continued)

(58) Field of Classification Search
CPC ....... A61B 8/0883; A61B 8/485; A61B 8/463; A61B 8/02; A61B 8/5207; A61B 8/5223;
(Continued)

(56) References Cited

U.S. PATENT DOCUMENTS 3,598,111 A    8/1971  Kahn
4,463,608 A    8/1984  Takeuchi et al.
(Continued)

FOREIGN PATENT DOCUMENTS

CN    102608212    7/2012
EP    0 221 409    5/1987
(Continued)

OTHER PUBLICATIONS

Provost et al., "Imaging the electromechanical activity of the heart in vivo", Proceedings of the National Academy of Sciences of the Unitied States of America, vol. 108, No. 21, May 24, 2011, pp. 8565-8570. (Year: 2011).*

(Continued)

*Primary Examiner* — Katherine L Fernandez
(74) *Attorney, Agent, or Firm* — Baker Botts L.L.P.

(57) ABSTRACT

Techniques for mapping behavior of a heart include acquiring a series of two or more images of the heart. The series of images is taken at one or more pixel locations, each pixel location corresponding to a region of the heart. Image data corresponding to the pixel locations can be obtained, and a periodicity of the image data measured for each of the pixel locations over the series of images. The periodicity corresponds to an electromechanical signal of the heart in the region corresponding to the measured one or more pixel locations.

31 Claims, 38 Drawing Sheets

Related U.S. Application Data

(60) Provisional application No. 61/712,057, filed on Oct. 10, 2012.

(51) Int. Cl.
*A61B 8/02* (2006.01)
*A61B 8/00* (2006.01)
*G01S 7/52* (2006.01)

(52) U.S. Cl.
CPC .............. *A61B 8/463* (2013.01); *A61B 8/485* (2013.01); *A61B 8/5207* (2013.01); *A61B 8/5223* (2013.01); *G01S 7/52036* (2013.01); *G01S 7/52042* (2013.01); *G01S 7/52087* (2013.01)

(58) Field of Classification Search
CPC .............. A61B 5/1102; G01S 7/52036; G01S 7/52042; G01S 7/52087
USPC .................................. 600/441, 438, 448, 449
See application file for complete search history.

(56) References Cited

U.S. PATENT DOCUMENTS

| | | |
|---|---|---|
| 4,777,599 A | 10/1988 | Dorogi et al. |
| 4,832,941 A | 5/1989 | Berwing et al. |
| 4,858,613 A | 8/1989 | Fry et al. |
| 4,882,679 A | 11/1989 | Tuy et al. |
| 4,926,675 A | 5/1990 | Schohl et al. |
| 5,038,787 A | 8/1991 | Antich et al. |
| 5,107,837 A | 4/1992 | Ophir et al. |
| 5,178,147 A | 1/1993 | Ophir et al. |
| 5,309,914 A | 5/1994 | Iinuma |
| 5,433,708 A | 7/1995 | Nichols et al. |
| 5,435,310 A | 7/1995 | Sheehan et al. |
| 5,457,754 A | 10/1995 | Han et al. |
| 5,601,084 A | 2/1997 | Sheehan et al. |
| 5,606,971 A | 3/1997 | Sarvazyan |
| 5,662,113 A | 9/1997 | Liu |
| 5,718,241 A | 2/1998 | Ben-Haim et al. |
| 5,722,411 A | 3/1998 | Suzuki et al. |
| 5,741,522 A | 4/1998 | Violante et al. |
| 5,752,515 A | 5/1998 | Jolesz et al. |
| 5,810,731 A | 9/1998 | Sarvazyan et al. |
| 5,840,028 A | 11/1998 | Chubachi et al. |
| 5,928,151 A | 7/1999 | Hossack et al. |
| 6,026,173 A | 2/2000 | Svenson et al. |
| 6,028,066 A | 2/2000 | Unger |
| 6,102,864 A | 8/2000 | Hatfield et al. |
| 6,102,865 A | 8/2000 | Hossack et al. |
| 6,106,465 A | 8/2000 | Napolitano et al. |
| 6,123,669 A | 9/2000 | Kanda et al. |
| 6,152,878 A | 11/2000 | Nachtomy et al. |
| 6,193,951 B1 | 2/2001 | Ottoboni et al. |
| 6,200,266 B1 | 3/2001 | Shokrollahi et al. |
| 6,241,675 B1 | 6/2001 | Smith et al. |
| 6,246,895 B1 | 6/2001 | Plews |
| 6,259,943 B1 | 7/2001 | Cosman et al. |
| 6,270,459 B1 | 8/2001 | Konofagou |
| 6,309,355 B1 | 10/2001 | Cain et al. |
| 6,312,382 B1 | 11/2001 | Mucci et al. |
| 6,352,507 B1 | 3/2002 | Torp et al. |
| 6,413,216 B1 | 7/2002 | Cain et al. |
| 6,425,865 B1 | 7/2002 | Salcudean et al. |
| 6,425,867 B1 | 7/2002 | Vaezy et al. |
| 6,447,450 B1 | 9/2002 | Oldstad |
| 6,488,629 B1 | 12/2002 | Saetre et al. |
| 6,491,636 B2 | 12/2002 | Chenal et al. |
| 6,508,768 B1 | 1/2003 | Hall et al. |
| 6,514,221 B2 | 2/2003 | Hynynen et al. |
| 6,529,770 B1 | 3/2003 | Grimblatov |
| 6,537,217 B1 | 3/2003 | Bjaerum et al. |
| 6,537,221 B2 | 3/2003 | Criton et al. |
| 6,671,541 B2 | 12/2003 | Bishop et al. |
| 6,683,454 B2 | 1/2004 | Rehwald et al. |
| 6,685,641 B2 | 2/2004 | Liu et al. |
| 6,689,060 B2 | 2/2004 | Phelps et al. |
| 6,701,341 B1 | 3/2004 | Wu |
| 6,770,033 B1 | 8/2004 | Fink et al. |
| 6,775,400 B1 | 8/2004 | Zhao et al. |
| 6,875,176 B2 | 4/2005 | Mourad et al. |
| 6,936,151 B1 | 8/2005 | Lock et al. |
| 6,984,209 B2 | 1/2006 | Hynynen et al. |
| 6,994,673 B2 | 2/2006 | Lysyansky et al. |
| 7,016,719 B2 | 3/2006 | Rudy et al. |
| 7,055,378 B2 | 6/2006 | Su et al. |
| 7,136,518 B2 | 11/2006 | Griffin et al. |
| 7,257,244 B2 | 8/2007 | Miga |
| 7,331,926 B2 | 2/2008 | Varghese et al. |
| 7,344,509 B2 | 3/2008 | Hynynen et al. |
| 7,421,101 B2 | 9/2008 | Georgescu et al. |
| 7,429,249 B1 | 9/2008 | Winder et al. |
| 7,449,306 B2 | 11/2008 | Elson et al. |
| 7,601,122 B2 | 10/2009 | Zagzebski et al. |
| 7,753,847 B2 | 7/2010 | Greenleaf et al. |
| 7,809,426 B2 | 10/2010 | Kim et al. |
| 7,896,821 B1 | 3/2011 | Magnin et al. |
| 8,029,444 B2 | 10/2011 | Pedrizzetti et al. |
| 8,150,128 B2 | 4/2012 | Konofagou et al. |
| 8,208,709 B2 | 6/2012 | Ding |
| 8,257,338 B2 | 9/2012 | Keenan et al. |
| 9,063,220 B2 | 6/2015 | Yoda |
| 9,358,023 B2 | 6/2016 | Konofagou et al. |
| 2002/0034757 A1 | 3/2002 | Cubicciotti |
| 2002/0038086 A1 | 3/2002 | Hynynen et al. |
| 2002/0039594 A1 | 4/2002 | Unger |
| 2002/0065461 A1 | 5/2002 | Cosman |
| 2002/0095081 A1 | 7/2002 | Vilsmeier |
| 2002/0151792 A1 | 10/2002 | Conston et al. |
| 2002/0169394 A1 | 11/2002 | Eppstein et al. |
| 2002/0169484 A1 | 11/2002 | Mathis et al. |
| 2002/0193784 A1 | 12/2002 | McHale et al. |
| 2003/0040675 A1 | 2/2003 | Sharrock |
| 2003/0097068 A1 | 5/2003 | Hossack et al. |
| 2003/0125621 A1 | 7/2003 | Drukker et al. |
| 2003/0135124 A1 | 7/2003 | Russell |
| 2003/0171672 A1 | 9/2003 | Varghese et al. |
| 2003/0174890 A1 | 9/2003 | Yamauchi |
| 2003/0220556 A1 | 11/2003 | Porat et al. |
| 2003/0236466 A1 | 12/2003 | Tarjan et al. |
| 2004/0006266 A1 | 1/2004 | Ustuner et al. |
| 2004/0049134 A1 | 3/2004 | Tosaya et al. |
| 2004/0049232 A1 | 3/2004 | Ideker et al. |
| 2004/0054357 A1 | 3/2004 | O'Donnell |
| 2004/0059220 A1 | 3/2004 | Mourad et al. |
| 2004/0059224 A1 | 3/2004 | Varghese et al. |
| 2004/0092816 A1 | 5/2004 | Ossmann et al. |
| 2004/0097805 A1 | 5/2004 | Verard et al. |
| 2004/0116812 A1 | 6/2004 | Selzer et al. |
| 2004/0122320 A1 | 6/2004 | Murashita |
| 2004/0143189 A1 | 7/2004 | Lysyansky et al. |
| 2004/0167403 A1 | 8/2004 | Nightingale et al. |
| 2004/0172081 A1 | 9/2004 | Wang |
| 2004/0210134 A1 | 10/2004 | Hynynen et al. |
| 2004/0210135 A1 | 10/2004 | Hynynen |
| 2004/0234113 A1 | 11/2004 | Miga |
| 2004/0236219 A1 | 11/2004 | Liu et al. |
| 2004/0249580 A1 | 12/2004 | Pourcelot et al. |
| 2004/0258760 A1 | 12/2004 | Wheatley et al. |
| 2005/0004466 A1 | 1/2005 | Hynenen et al. |
| 2005/0026262 A1 | 2/2005 | Yoshitani et al. |
| 2005/0054930 A1 | 3/2005 | Rickets et al. |
| 2005/0059876 A1 | 3/2005 | Krishnan |
| 2005/0080336 A1 | 4/2005 | Byrd et al. |
| 2005/0080469 A1 | 4/2005 | Larson et al. |
| 2005/0084538 A1 | 4/2005 | Dayton et al. |
| 2005/0124892 A1 | 6/2005 | Weitzel et al. |
| 2005/0175541 A1 | 8/2005 | Lanza et al. |
| 2005/0201942 A1 | 9/2005 | Dugstad et al. |
| 2005/0203395 A1 | 9/2005 | Sui et al. |
| 2005/0203399 A1 | 9/2005 | Vaezy et al. |
| 2005/0259864 A1 | 11/2005 | Dickinson et al. |
| 2005/0267695 A1 | 12/2005 | German |

(56) References Cited

U.S. PATENT DOCUMENTS

| | | | |
|---|---|---|---|
| 2005/0277824 A1 | 12/2005 | Aubry et al. |
| 2005/0277835 A1 | 12/2005 | Angelsen et al. |
| 2006/0034904 A1 | 2/2006 | Weimann |
| 2006/0058651 A1 | 3/2006 | Chiao et al. |
| 2006/0058671 A1 | 3/2006 | Vitek et al. |
| 2006/0058673 A1 | 3/2006 | Aase et al. |
| 2006/0074315 A1 | 4/2006 | Liang et al. |
| 2006/0078501 A1 | 4/2006 | Goertz et al. |
| 2006/0173320 A1 | 8/2006 | Radulescu |
| 2006/0241462 A1 | 10/2006 | Chou et al. |
| 2006/0241529 A1 | 10/2006 | Hynynen et al. |
| 2007/0049824 A1 | 3/2007 | Konofagou et al. |
| 2007/0055179 A1 | 3/2007 | Deem et al. |
| 2007/0059247 A1 | 3/2007 | Lindner et al. |
| 2007/0071683 A1 | 3/2007 | Dayton et al. |
| 2007/0129652 A1 | 6/2007 | Henry |
| 2007/0207194 A1 | 9/2007 | Grayburn et al. |
| 2007/0219447 A1 | 9/2007 | Kanai et al. |
| 2007/0232962 A1 | 10/2007 | Zumeris et al. |
| 2007/0239001 A1 | 10/2007 | Mehi et al. |
| 2007/0276242 A1 | 11/2007 | Konofagou |
| 2007/0276245 A1 | 11/2007 | Konofagou et al. |
| 2008/0194957 A1 | 8/2008 | Hoctor et al. |
| 2008/0200417 A1 | 8/2008 | Semple et al. |
| 2008/0243214 A1 | 10/2008 | Koblish |
| 2008/0260802 A1 | 10/2008 | Sawhney et al. |
| 2008/0269606 A1 | 10/2008 | Matsumura |
| 2008/0269668 A1 | 10/2008 | Keenan et al. |
| 2008/0285819 A1 | 11/2008 | Konofagou et al. |
| 2008/0319355 A1 | 12/2008 | Nita |
| 2008/0319375 A1 | 12/2008 | Hardy |
| 2009/0005711 A1 | 1/2009 | Konofagou et al. |
| 2009/0191244 A1 | 7/2009 | Kheir et al. |
| 2009/0221916 A1 | 9/2009 | Konofagou et al. |
| 2009/0247911 A1 | 10/2009 | Novak et al. |
| 2009/0270790 A1 | 10/2009 | Raghavan |
| 2010/0049036 A1 | 2/2010 | Kimh |
| 2010/0056924 A1 | 3/2010 | Powers |
| 2010/0143241 A1 | 6/2010 | Johnson et al. |
| 2010/0286527 A1 | 11/2010 | Cannon et al. |
| 2011/0028854 A1 | 2/2011 | Addison et al. |
| 2011/0098562 A1 | 4/2011 | Salgo et al. |
| 2011/0177005 A1 | 7/2011 | Rapoport et al. |
| 2011/0208038 A1 | 8/2011 | Konofagou et al. |
| 2011/0295105 A1 | 12/2011 | Konofagou et al. |
| 2011/0313328 A1 | 12/2011 | Nita |
| 2012/0004693 A1 | 1/2012 | Lo et al. |
| 2012/0179073 A1 | 7/2012 | Nita |
| 2013/0038479 A1 | 2/2013 | Eldar |
| 2013/0046229 A1 | 2/2013 | Konofagou et al. |
| 2013/0066211 A1 | 3/2013 | Konofagou et al. |
| 2013/0131495 A1 | 5/2013 | Konofagou et al. |
| 2013/0195313 A1 | 8/2013 | Gauthier |
| 2013/0289398 A1 | 10/2013 | Borden et al. |
| 2013/0304407 A1 | 11/2013 | George |
| 2013/0315491 A1 | 11/2013 | Konofagou et al. |
| 2014/0114216 A1 | 4/2014 | Konofagou et al. |
| 2016/0107002 A1 | 4/2016 | Nita |

FOREIGN PATENT DOCUMENTS

| | | |
|---|---|---|
| EP | 0 627 206 | 12/1994 |
| WO | WO 1999/037938 | 7/1999 |
| WO | WO 2007/0148279 | 12/2007 |
| WO | WO 2008/015012 | 2/2008 |
| WO | WO 2008/027520 | 3/2008 |
| WO | WO 2008/062342 | 5/2008 |
| WO | WO 2008/131217 | 10/2008 |
| WO | WO 2008/131302 | 10/2008 |
| WO | WO 2008/157422 | 12/2008 |
| WO | WO 2010/044385 | 4/2010 |
| WO | WO 2010/063951 | 6/2010 |
| WO | WO 2011/028690 | 3/2011 |
| WO | WO 2011/035312 | 3/2011 |
| WO | WO 2011/153268 | 12/2011 |

OTHER PUBLICATIONS

U.S. Appl. No. 11/433,510 (U.S. Pat. No. 8,858,441), filed May 12, 2006 (Oct. 14, 2014).

U.S. Appl. No. 11/697,573 (US 2007/0276245), filed Apr. 6, 2007 (Nov. 29, 2007).

U.S. Appl. No. 11/697,579 (US 2007/0276242), filed Apr. 6, 2007 (Nov. 29, 2007).

U.S. Appl. No. 11/899,004 (U.S. Pat. No. 8,150,128), filed Aug. 30, 2007 (Apr. 3, 2012).

U.S. Appl. No. 12/077,612 (US 2009/0005711), filed Mar. 19, 2008 (Jan. 1, 2009).

U.S. Appl. No. 12/096,254 (US 2009/0221916), filed Nov. 26, 2008 (Sep. 3, 2009).

U.S. Appl. No. 13/019,029 (U.S. Pat. No. 8,428,687), filed Feb. 1, 2011 (Apr. 23, 2013).

U.S. Appl. No. 13/045,070 (U.S. Pat. No. 9,302,124), filed Mar. 10, 2011 (Apr. 5, 2016).

U.S. Appl. No. 13/353,148 (US 2013/0066211), filed Jan. 18, 2012 (Mar. 14, 2013).

U.S. Appl. No. 13/426,400 (U.S. Pat. No. 9,358,023), filed Mar. 21, 2012 (Jun. 7, 2016).

U.S. Appl. No. 13/529,239 (US 2013/0131495), filed Jun. 21, 2012 (May 23, 2013).

U.S. Appl. No. 13/848,436 (U.S. Pat. No. 9,514,358), filed Mar. 21, 2013 (Dec. 6, 2016).

U.S. Appl. No. 14/091,010 (US 2014/0114216), filed Nov. 26, 2013 (Apr. 24, 2014).

U.S. Appl. No. 14/300,106 (U.S. Pat. No. 9,247,921), filed Jun. 9, 2014 (Feb. 2, 2016).

U.S. Appl. No. 14/449,820 (US 2014/0343424), filed Aug. 1, 2014 (Nov. 20, 2014).

U.S. Appl. No. 14/695,674 (US 2015/0297188), filed Apr. 24, 2015 (Oct. 22, 2015).

U.S. Appl. No. 15/048,761 (US 2016/0249880), filed Feb. 19, 2016 (Sep. 1, 2016).

U.S. Appl. No. 11/433,510, filed Jul. 23, 2014 Issue Fee Payment.

U.S. Appl. No. 11/433,510, filed Apr. 23, 2014 Notice of Allowance.

U.S. Appl. No. 11/433,510, filed Apr. 7, 2014 Applicant Initiated Interview Summary.

U.S. Appl. No. 11/433,510, filed Apr. 4, 2014 Response to Non-Final Office Action.

U.S. Appl. No. 11/433,510, filed Oct. 4, 2013 Non-Final Office Action.

U.S. Appl. No. 11/433,510, filed Mar. 30, 2012 Request for Continued Examination (RCE).

U.S. Appl. No. 11/433,510, filed Mar. 28, 2012 Advisory Action.

U.S. Appl. No. 11/433,510, filed Dec. 29, 2011 Response to Final Office Action.

U.S. Appl. No. 11/433,510, filed Sep. 30, 2011 Final Office Action.

U.S. Appl. No. 11/433,510, filed May 23, 2011 Response to Non-Final Office Action.

U.S. Appl. No. 11/433,510, filed Jan. 21, 2011 Non-Final Office Action.

U.S. Appl. No. 11/433,510, filed Oct. 28, 2010 Response to Non-Final Office Action.

U.S. Appl. No. 11/433,510, filed Apr. 28, 2010 Non-Final Office Action.

U.S. Appl. No. 11/433,510, filed Apr. 13, 2010 Amendment and Request for Continued Examination (RCE).

U.S. Appl. No. 11/433,510, filed Nov. 12, 2009 Final Office Action.

U.S. Appl. No. 11/433,510, filed Aug. 6, 2009 Response to Non-Final Office Action.

U.S. Appl. No. 11/433,510, filed Mar. 17, 2009 Non-Final Office Action.

U.S. Appl. No. 11/697,573, filed Jan. 12, 2015 Notice of Abandonment.

U.S. Appl. No. 11/697,573, filed Jun. 16, 2014 Non-Final Office Action.

U.S. Appl. No. 11/697,573, filed Apr. 17, 2014 Amendment and Request for Continued Examination (RCE).

U.S. Appl. No. 11/697,573, filed Feb. 21, 2014 Applicant Initiated Interview Summary.

(56) References Cited

OTHER PUBLICATIONS

U.S. Appl. No. 11/697,573, filed Oct. 17, 2013 Final Office Action.
U.S. Appl. No. 11/697,573, filed Sep. 4, 2013 Response to Non-Final Office Action.
U.S. Appl. No. 11/697,573, filed May 10, 2013 Non-Final Office Action.
U.S. Appl. No. 11/697,573, filed Jan. 18, 2013 Amendment and Request for Continued Examination (RCE).
U.S. Appl. No. 11/697,573, filed Jul. 18, 2012 Final Office Action.
U.S. Appl. No. 11/697,573, filed Jun. 27, 2012 Response to Non-Final Office Action.
U.S. Appl. No. 11/697,573, filed Jan. 26, 2012 Non-Final Office Action.
U.S. Appl. No. 11/697,573, filed Aug. 18, 2011 Amendment and Request for Continued Examination (RCE).
U.S. Appl. No. 11/697,573, filed Mar. 18, 2011 Final Office Action.
U.S. Appl. No. 11/697,573, filed Dec. 22, 2010 Response to Non-Final Office Action.
U.S. Appl. No. 11/697,573, filed Jun. 23, 2010 Non-Final Office Action.
U.S. Appl. No. 11/697,579, filed Nov. 28, 2011 Notice of Abandonment.
U.S. Appl. No. 11/697,579, filed Apr. 29, 2011 Final Office Action.
U.S. Appl. No. 11/697,579, filed Feb. 7, 2011 Response to Non-Final Office Action.
U.S. Appl. No. 11/697,579, filed Aug. 6, 2010 Non-Final Office Action.
U.S. Appl. No. 11/697,579, filed May 17, 2010 Response to Non-Final Office Action.
U.S. Appl. No. 11/697,579, filed Nov. 17, 2009 Non-Final Office Action.
U.S. Appl. No. 11/697,579, filed Oct. 15, 2009 Amendment and Request for Continued Examination (RCE).
U.S. Appl. No. 11/697,579, filed Jul. 15, 2009 Response to Final Office Action.
U.S. Appl. No. 11/697,579, filed Apr. 15, 2009 Final Office Action.
U.S. Appl. No. 11/697,579, filed Jan. 16, 2009 Response to Non-Final Office Action.
U.S. Appl. No. 11/697,579, filed Jul. 18, 2008 Non-Final Office Action.
U.S. Appl. No. 11/899,004, filed Jan. 3, 2012 Issue Fee payment.
U.S. Appl. No. 11/899,004, filed Oct. 4, 2012 Amendment after Allowance.
U.S. Appl. No. 11/899,004, filed Oct. 3, 2012 Notice of Allowance.
U.S. Appl. No. 11/899,004, filed Sep. 23, 2011 Amendment and Request for Continued Examination (RCE).
U.S. Appl. No. 11/899,004, filed Jul. 18, 2011 Notice of Allowance.
U.S. Appl. No. 11/899,004, filed May 10, 2011 Response to Non-Final Office Action.
U.S. Appl. No. 11/899,004, filed Feb. 8, 2011 Non-Final Office Action.
U.S. Appl. No. 12/077,612, filed Oct. 29, 2015 Notice of Abandonment.
U.S. Appl. No. 12/077,612, filed Apr. 9, 2015 Non-Final Office Action.
U.S. Appl. No. 12/077,612, filed Sep. 22, 2014 Amendment and Request for Continued Examination (RCE).
U.S. Appl. No. 12/077,612, filed Mar. 21, 2014 Final Office Action.
U.S. Appl. No. 12/077,612, filed Jan. 30, 2014 Response to Non-Final Office Action.
U.S. Appl. No. 12/077,612, filed Aug. 30, 2013 Non-Final Office Action.
U.S. Appl. No. 12/077,612, filed Oct. 26, 2011 Amendment and Request for Continued Examination (RCE).
U.S. Appl. No. 12/077,612, filed May 26, 2011 Final Office Action.
U.S. Appl. No. 12/077,612, filed Mar. 23, 2011 Response to Non-Final Office Action.
U.S. Appl. No. 12/077,612, filed Nov. 16, 2010 Non-Final Office Action.
U.S. Appl. No. 12/096,254, filed Sep. 28, 2015 Notice of Abandonment.
U.S. Appl. No. 12/096,254, filed Feb. 27, 2015 Non-Final Office Action.
U.S. Appl. No. 12/096,254, filed Sep. 22, 2014 Amendment and Request for Continued Examination (RCE).
U.S. Appl. No. 12/096,254, filed Mar. 21, 2014 Final Office Action.
U.S. Appl. No. 12/096,254, filed Dec. 23, 2013 Response to Non-Final Office Action.
U.S. Appl. No. 12/096,254, filed Dec. 17, 2013 Applicant Initiated Interview Summary.
U.S. Appl. No. 12/096,254, filed Aug. 23, 2013 Non-Final Office Action.
U.S. Appl. No. 12/096,254, filed Nov. 30, 2012 Amendment and Request for Continued Examination (RCE).
U.S. Appl. No. 12/096,254, filed May 31, 2012 Final Office Action.
U.S. Appl. No. 12/096,254, filed Apr. 4, 2012 Response to Non-Final Office Action.
U.S. Appl. No. 12/096,254, filed Oct. 5, 2011 Non-Final Office Action.
U.S. Appl. No. 13/019,029, filed Mar. 21, 2013 Issue Fee payment.
U.S. Appl. No. 13/019,029, filed Dec. 26, 2012 Notice of Allowance.
U.S. Appl. No. 13/045,070, filed Feb. 24, 2016 Issue Fee Payment.
U.S. Appl. No. 13/045,070, filed Jan. 15, 2016 Notice of Allowance.
U.S. Appl. No. 13/045,070, filed Jan. 15, 2016 Applicant Initiated Interview Summary.
U.S. Appl. No. 13/045,070, filed Jan. 15, 2016 After Final Consideration Program Decision.
U.S. Appl. No. 13/045,070, filed Jan. 7, 2016 Notice of Appeal Filed.
U.S. Appl. No. 13/045,070, filed Nov. 17, 2015 Amendment after Final and After Final Consideration Program Request.
U.S. Appl. No. 13/045,070, filed Jul. 7, 2015 Final Office Action.
U.S. Appl. No. 13/045,070, filed May 18, 2015 Applicant Initiated Interview Summary.
U.S. Appl. No. 13/045,070, filed May 15, 2015 Response to Non-Final Office Action.
U.S. Appl. No. 13/045,070, filed Jan. 16, 2015 Non-Final Office Action.
U.S. Appl. No. 13/045,070, filed Nov. 7, 2013 Amendment and Request for Continued Examination (RCE).
U.S. Appl. No. 13/045,070, filed May 9, 2013 Final Office Action.
U.S. Appl. No. 13/045,070, filed Dec. 21, 2012 Response to Non-Final Office Action.
U.S. Appl. No. 13/045,070, filed Jun. 22, 2012 Non-Final Office Action.
U.S. Appl. No. 13/353,148, filed Feb. 26, 2016 Notice of Abandonment.
U.S. Appl. No. 13/353,148, filed Aug. 12, 2015 Non-Final Office Action.
U.S. Appl. No. 13/353,148, filed Jul. 6, 2015 Amendment and Request for Continued Examination (RCE).
U.S. Appl. No. 13/353,148, filed Mar. 3, 2015 Final Office Action.
U.S. Appl. No. 13/353,148, filed Oct. 24, 2014 Response to Non-Final Office Action.
U.S. Appl. No. 13/353,148, filed Oct. 14, 2014 Applicant Initiated Interview Summary.
U.S. Appl. No. 13/353,148, filed Apr. 24, 2014 Non-Final Office Action.
U.S. Appl. No. 13/353,148, filed Oct. 17, 2013 Final Office Action.
U.S. Appl. No. 13/353,148, filed Sep. 11, 2013 Response to Non-Final Office Action.
U.S. Appl. No. 13/353,148, filed Jun. 20, 2013 Non-Final Office Action.
U.S. Appl. No. 13/426,400, filed May 13, 2016 Notice of Allowance.
U.S. Appl. No. 13/426,400, filed May 5, 2016 Issue Fee Payment.
U.S. Appl. No. 13/426,400, filed Feb. 5, 2016 Notice of Allowance.
U.S. Appl. No. 13/426,400, filed Dec. 4, 2015 Applicant Initiated Interview Summary.
U.S. Appl. No. 13/426,400, filed Dec. 4, 2015 Response to Non-Final Office Action.

(56) References Cited

OTHER PUBLICATIONS

U.S. Appl. No. 13/426,400, filed Jul. 2, 2015 Non-Final Office Action.
U.S. Appl. No. 13/426,400, filed Mar. 23, 2015 Amendment and Request for Continued Examination (RCE).
U.S. Appl. No. 13/426,400, filed Dec. 23, 2014 Final Office Action.
U.S. Appl. No. 13/426,400, filed Oct. 2, 2014 Response to Non-Final Office Action.
U.S. Appl. No. 13/426,400, filed May 5, 2014 Non-Final Office Action.
U.S. Appl. No. 13/529,239, filed Jan. 8, 2016 Notice of Abandonment.
U.S. Appl. No. 13/529,239, filed Jun. 4, 2015 Final Office Action.
U.S. Appl. No. 13/529,239, filed Mar. 5, 2015 Applicant Initiated Interview Summary.
U.S. Appl. No. 13/529,239, filed Mar. 3, 2015 Response to Non-Final Office Action.
U.S. Appl. No. 13/529,239, filed Sep. 3, 2014 Non-Final Office Action.
U.S. Appl. No. 13/529,239, filed Jun. 30, 2014 Amendment and Request for Continued Examination (RCE).
U.S. Appl. No. 13/529,239, filed Dec. 31, 2013 Final Office Action.
U.S. Appl. No. 13/529,239, filed Dec. 3, 2013 Response to Non-Final Office Action.
U.S. Appl. No. 13/529,239, filed Jul. 5, 2013 Non-Final Office Action.
U.S. Appl. No. 13/848,436, filed Nov. 1, 2016 Issue Fee Payment.
U.S. Appl. No. 13/848,436, filed Aug. 2, 2016 Notice of Allowance.
U.S. Appl. No. 13/848,436, filed Jul. 15, 2016 Terminal Disclaimer Filed.
U.S. Appl. No. 13/848,436, filed Jun. 21, 2016 Response to Non-Final Office Action.
U.S. Appl. No. 13/848,436, filed Jan. 21, 2016 Non-Final Office Action.
U.S. Appl. No. 13/848,436, filed Dec. 21, 2015 Response to Restriction Requirement.
U.S. Appl. No. 13/848,436, filed Jul. 22, 2015 Restriction Requirement Filed.
U.S. Appl. No. 14/091,010, filed Sep. 12, 2016 Non-Final Office Action.
U.S. Appl. No. 14/300,106, filed Dec. 22, 2015 Issue Fee Payment.
U.S. Appl. No. 14/300,106, filed Sep. 24, 2015 Notice of Allowance.
(Multiple Sources) Sixth International Conference on the Measurement and Imaging of Tissue Elasticity. Nov. 2, 2007 [Retrieved on Mar. 12, 2014], pp. 1-154, retrieved from the internet: <URL:http://www.elasticityconference.org/prior_conf/2007/2007Proceedings.pdf>.
"Vial", Retrieved from http://en.wikipedia.org/w/index.php?title=Vial&oldid=603936258 [Downloaded on May 20, 2014].
Abbott, et al., "Astrocyte-Endothelial Interactions at the Blood-Brain Barrier", Nat. Rev. Neurosci., 7(1):41-53 (2006).
Alam, et al., "An Adaptive Strain Estimator for Elastography", IEEE Transactions on Ultrasonics, Ferroelectrics, and Frequency Control, vol. 45, No. 2, Mar. 1998.
Ammi, et al., "Ultrasonic contrast agent shell rupture detected by inertial cavitation and rebound signals", IEEE Transactions, 53(1):126-136 (2006).
Ashikaga, et al., "Transmural Dispersion of Myofiber Mechanics: Implications for Electrical Heterogeneity In Vivo", Journal of the American College of Cardiology, 49(8):909-916 (2007).
Aubry, et al., "Experimental Demonstration of Noninvasive Transskull Adaptive Focusing Based on Prior Computed Tomography Scans", The Journal of the Acoustical Society of America, 113:84 (2003).
Avolio, et al., "Effects of aging on changing arterial compliance and left ventricular load in a northern Chinese urban community", Circulation, 68(1):50-58 (1983).

Azuma, et al., "Bubble Generation by Standing Wave in Water Surrounded by Cranium With Transcranial Ultrasonic Beam", Japanese Journal of Applied Physics, 44:4625-4630 (2005).
Badke, et al., "Effects of Ventricular Pacing on Regional Left Ventricular Performance in the Dog", Am J Physiol Heart Circ Physiol., 238:H858-867 (1980).
Baron, et al., "Simulation of Intracranial Acoustic Fields in Clinical Trials of Sonothrombolysis", Ultrasound Med. Biol., 35(7):1148-1158 (2009).
Baseri, et al., "Multi-Modality Safety Assessment of Blood-Brain Barrier Opening Using Focused Ultrasound and Definity Microbubbles: A Short-Term Study", Ultrasound Med. Biol., 6(9):1445-1459 (2010).
Behrens, et al., "Low-Frequency, Low-Intensity Ultrasound Accelerates Thrombolysis Through the Skull", Ultrasound in Medicine & Biology, 25:269-273 (1999).
Bercoff, et al., "Supersonic Shear Imaging: A New Technique for Soft Tissue Elasticity Mapping", IEEE Transactions on Ultrasonics Ferroelectrics and Frequency Control, 51:396-409 (2004).
Berger, et al., "Single-Beat Noninvasive Imaging of Cardiac Electrophysiology of Ventricular Pre-Excitation", Journal of the American College of Cardiology, 48:2045-2052 (2006).
Bers, "Cardiac Excitation-Contraction Coupling", Nature, 415:198-205 (2002).
Bonnefous, et al, "Time Domain Formulation of Pulse-Doppler Ultrasound and Blood Velocity Estimation by Cross Correlation", Ultrason Imaging, 8(2):73-85 (1986).
Borden, et al., "Ultrasound Radiation Force Modulates Ligand Availability on Target Contrast Agents", Mol. Imaging, 5:139-147 (2006).
Brekke, et al., "Tissue Doppler Gated (TDOG) Dynamic Three-Dimensional Ultrasound Imaging of the Fetal Heart", Ultrasound Obstet Gynecol., 24(2):192-198 (2004).
Brooks, et al., "Electrical Imaging of the Heart", IEEE Signal Processing Magazine, 14:24-42 (1997).
Brundin, et al., "Restorative Therapies in Parkinson's Disease", Springer Verlag (2006).
Campbell, et al., "Mechanisms of Transmurally Varying Myocyte Electromechanics in an Integrated Computational Model", Philos Transact A Math Phys Eng Sci., 366:3361-3380 (2008).
Carman, et al., "Adenosine receptor signaling modulates permeability of the blood-brain barrier", The Journal of Neuroscience, 31(37):13272-13280 (2011).
Caskey, et al., "Direct Observations of Ultrasound Microbubble Contrast Agent Interaction With the Microvessel Wall", J. Acoust. Soc. Amer., 122(2):1191-1200 (2007).
Caskey, et al., "Microbubble Oscillation in Tubes With Diameters of 12, 25, and 195 Microns", Appl. Phys. Lett., 88(3):033902-1-033902-3 (2006).
Cavaglia, et al., "Regional Variation in Brain Capillary Density and Vascular Response to Ischemia", Brain Res., 910(1-2):81-93 (2001).
Chan, "Transgenic Nonhuman Primates for Neurodegenerative Diseases", Reproductive Biology and Endocrinology, 2:39 (2004).
Chang, et al., "3-D US Frame Positioning Using Speckle Decorrelation and Image Registration", Ultrasound in Medicine and Biology, pp. 801-812 (2003).
Chen, et al., "Architectural Acoustics and Noise: Advancements and Best Practices in Instrumentation for Architectural Acoustics and Noise", J. Acoust. Soc. Am.; 164th Meeting: Acoustical Society of America, 132(3, Pt. 2):1977-2018 (Sep. 2012).
Chen, et al., "Engineering Acoustics and ASA Committee on Standards: Sound Intensity Measurements", J. Acoust. Soc. Am.; 164th Meeting: Acoustical Society of America, 132(3, Pt. 2):1984 (Sep. 2012).
Chen, et al., "Estimation of Displacement Vectors and Strain Tensors in Elastography Using Angular Insonifications", IEEE Transactions on Medical Imaging, 23(12):1479-1489 (2004).
Chen, et al., "Optimization of Ultrasound Parameters for Cardiac Gene Delivery of Adenoviral or Plasmid Deoxyribonucleic Acid by Ultrasound-Targeted Microbubble Destruction", J. Amer. Coll. Cardiol., 42(2):301-308 (2003).
Chen, et al., "The size of blood-brain barrier opening induced by focused ultrasound is dictated by the acoustic pressure", J. Cereb. Blood Flow Metab., 34:1197-1204 (2014).

(56) References Cited

OTHER PUBLICATIONS

Choi et al., "Brain region and microbubble-size dependence of the focused ultrasound-induced blood-brain barrier opening in mice in vivo", IEEE International Ultrasonics Symposium, Rome, ITA, Sep. 20-23, 2009.
Choi, et al., "Delivery of pharmacologically-relevant sized molecules through the ultrasound-induced blood-brain barrier opening in vivo", Neuroscience, Chicago, IL, USA, Oct. 17-21, 2009.
Choi, et al., "Feasibility of Transcranial, Localized Drug-Delivery in the Brain of Alzheimer's-Model Mice Using Focused Ultrasound", 2005 IEEE Ultrasonics Symposium, pp. 988-991 (Sep. 18-21, 2005).
Choi, et al., "Focused Ultrasound-Induced Molecular Delivery Through the Blood-Brain Barrier", Presented at the IEEE Symp. Ultrason. Ferroelect. Freq. Control, New York, NY, pp. 1192-1195 (2007).
Choi, et al., "Microbubble-size dependence of focused ultrasound-induced blood-brain barrier opening in mice in vivo", IEEE transactions on Biomedical Engineering, 57(1):145-154 (2010).
Choi, et al., "Molecules of Various Pharmacologically-Relevant Sizes Can Cross the Ultrasound-Induced Blood-Brain Barrier Opening In Vivo", Ultrasound in Medicine & Biology, 36(1):58-67 (2009).
Choi, et al., "Noninvasive and Transient Blood-Brain Barrier Opening in the Hippocampus of Alzheimer's Double Transgenic Mice Using Pulsed Focused Ultrasound", Ultrasonic Imaging, pp. 189-200 (2008).
Choi, et al., "Noninvasive, Transcranial and Localized Opening of the Blood-Brain Barrier Using Focused Ultrasound in Mice", Ultrasound in Medicine & Biology, 33(1):95-104 (2007).
Choi, et al., "Optimization of Blood-Brain Barrier Opening in Mice using Focused Ultrasound", 2006 IEEE Ultrasounics Symposium [online], Jun. 2007.
Choi, et al., "Spatio-Temporal Analysis of Molecular Delivery Through the Blood-Brain Barrier Using Focused Ultrasound", Physics in Medicine and Biology, 52:5509-5530 (2007).
Chomas, et al., "Threshold of Fragmentation for Ultrasonic Contrast Agents", J. Biomed. Opt., 6(2):141-150 (2001).
Clarke, et al., "The changes in acoustic attenuation due to in vitro heating", Ultrasound Med Biol 29:127-135 (2003).
Clement, et al., "A Hemisphere Array for Non-Invasive Ultrasound Brain Therapy and Surgery", Phys Med Biol., 45:3707-3719 (2000).
Cobbold, R.S.C., "Foundations of biomedical ultrasound", Biomedical engineering series, Oxford University Press, pp. 422-423 (2006).
Connor, "Simulation Methods and Tissue Property Models for Non-Invasive Transcranial Focused Ultrasound Surgery", Ph.D. Thesis (2005).
Connor, et al., "A Unified Model for the Speed of Sound in Cranial Bone Based on Genetic Algorithm Optimization", Physics in Medicine and Biology, 47:3925-3944 (2002).
Cordeiro, et al., "Transmural Heterogeneity of Calcium Activity and Mechanical Function in the Canine Left Ventricle", Am J Physiol. Heart Circ. Physiol., 286:H1471-1479 (2004).
Coyle, "Arterial Patterns of the Rat Rhinencephalon and Related Structures", Exp. Neurol., 49(3):671-690 (1975).
Coyle, "Spatial Features of the Rat Hippocampal Vascular System", Exp. Neurol., 58(3): 549-561 (1978).
Coyle, "Vascular Patterns of the Rat Hippocampal Formation", Exp. Neurol., 52(3): 447-458 (1976).
Crum, et al., "Bjerknes Forces on Bubbles in a Stationary Sound Field", The Journal of the Acoustical Society of America, 57(6):1363-1370 (1975).
Cutnell, et al., (1998). Physics, Fourth Edition. New York. Table of Contents.
Daffertshofer, et al., "Transcranial Low-Frequency Ultrasound-Mediated Thrombolysis in Brain Ischemia: Increased Risk of Hemorrhage With Combined Ultrasound and Tissue Plasminogen Activator: Results of a Phase II Clinical Trial", Stroke, 36:1441-146 (2005).
Damianou, "In vitro and in vivo ablation of porcine renal tissues using high-intensity focused ultrasound", Ultrasound Med Biol 29:1321-30 (2003).
Damianou, et al., "Dependence of ultrasonic attenuation and absorption in dog soft tissues on temperature and thermal dose", J Acoust Soc Am, 102(1):628-634 (1997).
Datta, et al., "Correlation of Cavitation With Ultrasound Enhancement of Thrombolysis", Ultrasound in Medicine & Biology, 32(8):1257-1267 (2006).
De Craene, et al., "Temporal diffeomorphic free-form deformation: Application to motion and strain estimation from 3D echocardiography", Medical Image Analysis, 16(2):427-450 (2012).
Declerck, et al., "Left ventricular motion reconstruction from planar tagged MR images: a comparison", Phys Med Biol., 45(6):1611-1632 (2000).
Deffieux, et al., "Transcranial Focused Ultrasound for Blood-Brain Barrier Opening—Numerical Simulations With In Vitro Validation in Human and Monkey Skulls", Title page and Table of Contents for the AIUM Annual Convention, San Diego, CA, (2010).
Definition of "spatial filter" retrieved from http://www.onelook.com/ on May 26, 2015.
DeLong, "Primate Models of Movement Disorders of Basal Ganglia Origin", Trends Neurosci., 13(7):281-285 (1990).
DuBose, et al., "Confusion and Direction in Diagnostic Doppler Sonography", Journal of Diagnostic Medical Sonography, 25(3):173-177 (2009).
Duck, "Physical Properties of Tissue: A Comprehensive Reference Book", Academic Press, London, UK, 1990.
Duerinckx, et al., "In vivo acoustic attenuation in liver: correlations with blood tests and histology", Ultrasound Imaging, 14(5):405-413 (1988).
Duerinckx, et al., "Letter to the editor", Ultrasonic Imaging 1986; 8:225-6.
Durrer, et al., "Total Excitation of the Isolated Human Heart", Circulation, 41:899-912 (1970).
Edwards, et al., "Effects of Ischemia on Left-Ventricular Regional Function in the Conscious Dog", American Journal of Physiology, 240, H413-H420 (1981).
EPO Search Report and Opinion and Office Action for EP0684017.2 dated Dec. 7, 2009 and Mar. 8, 2010.
Epstein-Barasg, et al., "A microcomposite hydrogel for repeated on-demand ultrasound-triggered drug delivery", Biomaterials, 31(19):5208-5217 (2010).
Erpelding, et al., "Bubble-Based Acoustic Radiation Force Using Chirp Insonation to Reduce Standing Wave Effects", Ultrasound in Medicine & Biology, 33(2):263-269 (2007).
European Search Report for EP Application No. 10838238, dated May 6, 2014.
Everbach, et al., "Cavitational Mechanisms in Ultrasound-Accelerated Thrombolysis at 1 Mhz", Ultrasound in Medicine & Biology, 26(7):1153-1160 (2000).
Faris, et al., "Novel Technique for Cardiac Electromechanical Mapping With Magnetic Resonance Imaging Tagging and an Epicardial Electrode Sock", Ann Biomed Eng., 31:430-440 (2003).
Farook, et al., "Preparation of Microbubble Suspensions by Co-Axial Electrohydrodynamic Atomization", Med. Eng. Phys., 29(7):749-754 (2007).
Fenster, et al., "Three-dimensional ultrasound imaging", Phys Med Biol, 46(5):R67-R99 (2001).
Feshitan, et al., "Microbubble Size Isolation by Differential Centrifugation", Journal of Colloid and Interface Science, 329:316-324 (2009).
Fiske, et al., "Special Focus Section: Gene Therapy for Parkinson's Disease", Experimental Neurology, 209:28-29 (2008).
Fry, "Transkull Transmission of an Intense Focused Ultrasonic Beam", Ultrasound in Medicine & Biology, 3:179 (1977).
Fry, et al., "A Focused Ultrasound System for Tissue Volume Ablation in Deep Seated Brain Sites", IEEE 1986 Ultrasonics Symposium, pp. 1001-1004 (1986).
Fujii, et al., "A new method for attenuation coefficient measurement in the liver", Journal of Ultrasound Medicine, 21(7):783-788 (2002).
Fung, (1993). Biomechanics—Mechanical Properties of Living Tissues. New York. Table of Contents.

(56) References Cited

OTHER PUBLICATIONS

Ganan-Calvo, et al., "Perfectly Monodisperse Microbubbling by Capillary Flow Focusing", Phys. Rev. Lett., 87(27) Pt 1: 274501-1-274501-4 (2001).
Gaud, et al., "Acoustic Characterization of Single Ultrasound Contrast Agent Microbubbles", The Journal of the Acoustic Society of America, 124(6):4091 (2008).
Ghosh, et al., "Cardiac Memory in Patients With Wolff-Parkinson-White Syndrome: Noninvasive Imaging of Activation and Repolarization Before and After Catheter Ablation," Circulation, 118:907-915 (2008).
Giacobini, "Alzheimer Disease, From Molecular Biology to Therapy", Advances in Experimental Medicine and Biology, 429:235-245 (1997).
Ginat, et al., "High-resolution ultrasound elastography of articular cartilage in vitro", Proceedings of the 28th IEEE EMBS Annual International Conference, New York City, USA, pp. 6644-6647 (Aug. 30th-Sep. 3rd, 2006).
Greenstein, et al., "Mechanisms of Excitation-Contraction Coupling in an Integrative Model of the Cardiac Ventricular Myocyte", Biophysical Journal, 90:77-91 (2006).
Greenwald, "Pulse Pressure and Arterial Elasticity", Qjm-an International Journal of Medicine, 95(2):107-112 (2002).
Gupta, et al., "Changes in Passive Mechanical Stiffness of Myocardial Tissue with Aneurysm Formation", Circulation, 89:2315-2326 (1994).
Gurev, et al., "Distribution of Electromechanical Delay in the Heart: Insights From a Three-Dimensional Electromechanical Model", Biophysical Journal, 99:745-754 (2010).
Gurev, et al., "In Silico Characterization of Ventricular Activation Pattern by Electromechanical Wave Imaging", Supplement to Heart Rhythm., 6:S357 (2009).
Heimdal, et al., "Real-time Strain Rate Imaging of the Left Ventricle by Ultrasound", J Am Soc Echocardiography, 11(11):1013-1019 (1998).
Henderson, et al., "Series Elasticity of Heart Muscle During Hypoxia", Cardiovascular Research, 5:10-14 (1971).
Housden, et al., "Ultrasonic imaging of 3D displacement vectors using a simulated 2D array and beamsteering", Ultrasonics, 53(2):615-621 (2013).
Huang, et al. "Watershed Segmentation for Breast Tumor in 2-D Sonography", Ultrasound in Medicine and Biology, pp. 625-632 (2004).
Hynynen, et al., "Demonstration of Potential Noninvasive Ultrasound Brain Therapy Through an Intact Skull", Ultrasound in Medicine & Biology, 24(2):275-283 (1998).
Hynynen, et al., "Focal Disruption of the Blood-Brain Barrier Due to 260-Khz Ultrasound Bursts: A Method for Molecular Imaging and Targeted Drug Delivery", J. Neurosurg., 105(3):445-454 (2006).
Hynynen, et al., "Noninvasive MR Imaging—Guided Focal Opening of the Blood-Brain Barrier in Rabbits", Radiology, 220(3):640-646 (2001).
Hynynen, et al., "Trans-Skull Ultrasound Therapy: The Feasibility of Using Image-Derived Skull Thickness Information to Correct the Phase Distortion", IEEE Transactions on Ultrasonics, Ferroelectrics and Frequency Control, 46(3):752-755, (1999).
International Preliminary Report on Patentability, dated Apr. 17, 2007 and Written Opinion for PCT/US2005/037669, dated Jun. 13, 2006.
International Preliminary Report on Patentability, dated Apr. 17, 2007 and Written Opinion for PCT/US2005/037670, dated Nov. 22, 2006.
International Preliminary Report on Patentability, dated Jun. 11, 2008 and Written Opinion for PCT/US2006/061809, dated Oct. 4, 2007.
International Preliminary Report on Patentability, dated Nov. 14, 2007 and Written Opinion for PCT/US2006/018454, dated Aug. 9, 2007.
International Search Report and Written Opinion dated Feb. 3, 2014 in International Application No. PCT/US2013/064377.
International Search Report and Written Opinion dated Jul. 17, 2012 for International Application No. PCT/US12/34136.
International Search Report and Written Opinion dated Oct. 18, 2012 for International Application No. PCT/US12/35685.
International Search Report and Written Opinion for PCT/US2006/036460, dated Sep. 5, 2007; International Preliminary Report dated Mar. 26, 2008.
International Search Report and Written Opinion for PCT/US2009/056513, dated Oct. 30, 2009.
International Search Report and Written Opinion for PCT/US2009/052563 dated Oct. 8, 2009.
International Search Report and Written Opinion for PCT/US2009/056565 dated Nov. 2, 2009.
International Search Report and Written Opinion for PCT/US2010/049681, dated Dec. 7, 2010.
International Search Report and Written Opinion for PCT/US2010/061742, dated Mar. 1, 2011.
International Search Report and Written Opinion for PCT/US2011/034704, dated Aug. 18, 2011.
International Search Report for PCT/US2007/019149 dated Feb. 29, 2008.
International Search Report for PCT/US2014/011631, dated Mar. 31, 2014.
Jagannathan, et al., "High-Intensity Focused Ultrasound Surgery of the Brain: Part 1—A Historical Perspective With Modern Applications", Neurosurgery, 64(2):201-211 (2009).
Jasaityte, et al., "Current state of three-dimensional myocardial strain estimation using echocardiography", J Am Soc Echocardiogr., 26(1):15-28 (2013).
Jensen, et al., "Calculation of Pressure Fields From Arbitrarily Shaped, Apodized, and Excited Ultrasound Transducers", IEEE Transactions on Ultrasonics, Ferroelectrics and Frequency Control, 39(2):262-267 (1992).
Kallel, et al., "A Least-Squares Strain Estimator for Elastography", Ultrasonic Imaging, 19:195-208 (1997).
Kanai, et al. "Propagation of Spontaneously Actuated Pulsive Vibration in Human Heart Wall and In Vivo Viscoelasticity Estimation", IEEE Transactions on Ultrasonics, Ferroelectrics, and Frequency Control, 52(11):1931-1942 (2005).
Kanai, et al., "A New Method for Measuring Small Local Vibrations in the Heart Using Ultrasound", IEEE Transactions on Biomedical Engineering, 40(12):1233-1242 (1993).
Kanai, et al., "Myocardial Rapid Velocity Distribution", Ultrasound Med Biol., 27(4): 481-498 (2001).
Kanai, et al., "Transcutaneous Measurement of Frequency Dispersion in the Regional Pulse Wave Velocity", 2000 IEEE Ultrasonics Symposium, pp. 1-4 (2000).
Kaufman, et al., "Ultrasound Simulation in Bone", IEEE Transactions on Ultrasonics Ferroelectrics and Frequency Control, 55(6):1205-1218 (2008).
Kimber, et al., "A Comparison of Unipolar and Bipolar Electrodes During Cardiac Mapping Studies", Pacing Clin Electro., 19:1196-1204 (1996).
Kinoshita, et al., "Noninvasive Localized Delivery of Herceptin to the Mouse Brain by MRI-Guided Focused Ultrasound-Induced Blood-Brain Barrier Disruption", Proceedings of the National Academy of Sciences, 103(31):11719-11723 (2006).
Kinoshita, et al., "Targeted Delivery of Antibodies Through the Blood-Brain Barrier by MRI-Guided Focused Ultrasound", Biochemical and Biophysical Research Communications, 340:1085-1090 (2006).
Klein, et al., "Interdependency of Local Capillary Density, Blood Flow, and Metabolism in Rat Brains", Amer. J. Physiol., 251(6) Pt 2: H1333-H1340 (1986).
Klempner, et al., "Neutrophil Plasma Membranes I. High-Yield Purification of Human Neutrophil Plasma Membrane Vesicles by Nitrogen Cavitation and Differential Centrifugation", Journal of Cell Biology, 86:21-28 (1980).
Konofagou, et al. "Elastographic Imaging of the Strain Distribution at the Anterior Cruciate Ligament and ACL-Bone Insertions", Proceedings of the 2005 IEEE 27th Annual International Conference of the Engineering in Medicine and Biology Society, pp. 972-975 (Shanghai, China Sep. 1-4, 2005).

(56) References Cited

OTHER PUBLICATIONS

Konofagou, et al., "A New Elastographic Method for Estimation and Imaging of Lateral Strains, Corrected Axial Strains and Poison's Ratios in Tissues", Ultrasound in Medicine and Biology, 24(8):1183-1199 (1998).
Konofagou, et al., "Electromechanical Wave Imaging for Noninvasive Mapping of the 3D Electrical Activation Sequence in Canines and Humans In Vivo", Journal of Biomechanics, 45(5):856-864 (2012).
Konofagou, et al., "Mechanism and Safety at the Threshold of the Blood-Brain Barrier Opening In Vivo", International Society on Therapeutic Ultrasound (ISTU), Aix-en-Provence, France, Sep. 21-24, 2009.
Konofagou, et al., "Myocardial Elastography—Feasibility Study In Vivo", Ultrasound Med & Biol., 28(4):475-482 (2002).
Konofagou, et al., "Noninvasive electromechanical wave imaging and conduction-relevant velocity estimation in vivo", Ultrasonics, 50(2):208-215 (2010).
Konofagou, et al., "Noninvasive Electromechanical Wave Imaging and Conduction Velocity Estimation In Vivo", 2007 IEEE Ultrasonics Symposium, pp. 969-972 (2007).
Konofagou, et al., "Three-Dimensional Motion Estimation in Elastography", IEEE Proceedings of the Symposium of Ultrasonics, Ferroelectrics and Frequency Control in Sendai, Japan, pp. 1745-1748 (1998).
Konofagou, et al., "Ultrasound-Induced Blood-Brain Barrier Opening", Current Pharmaceutical Biotechnology, 13(7):1332-1345 (2012).
Korecka, et al., "Cell-Replacement and Gene-Therapy Strategies for Parkinson's and Alzheimers Disease", Regen. Med., 2(4):425-446 (2007).
Kremkau, et al., "Ultrasonic Attenuation and Propagation Speed in Normal Human Brain," The Journal of the Acoustical Society of America, 70:29 (1981).
Kunz, et al., "The Finite Difference Time Domain Method for Electromagnetics", CRC Press, Boca Raton, USA (1993).
Kvale, et al., "Size Fractionation of Gas-Filled Microspheres by Flotation", Separations Technol., 6(4):219-226 (1996).
Lai, et al., "Introduction to Continuum Mechanics", (Pergamon Pr). 3rd Ed. (1993).
Lee, et al., "Improving Stereotactic Surgery Using 3-D Reconstruction", IEEE Engineering in Medicine and Biology Magazine, 21:109-116 (2002).
Lee, et al., "Theoretical Quality Assessment of Myocardial Elastography With In Vivo Validation", IEEE Transactions, Ultrasonics, Ferroelectrics and Frequency Control, 54:2233-2245 (2007).
Liu, et al., "Hemorrhage Detection During Focused-Ultrasound Induced Blood-Brain-Barrier Opening by Using Susceptibility-Weighted Magnetic Resonance Imaging", Ultrasound in Med. & Biol., 34(4):598-606 (2008).
Liu, et al., "Magnetic Resonance Imaging Enhanced by Superparamagnetic Iron Oxide Particles: Usefulness for Distinguishing Between Focused Ultrasound-Induced Blood-Brain Barrier Disruption and Brain Hemorrhage", J. of Magnetic Resonance Imaging, 29:31-38 (2009).
Lu, et al., "Design and Experiment of 256-Element Ultrasound Phased Array for Noninvasive Focused Ultrasound Surgery", Ultrasonics, 44:e325-e330 (2006).
Luo, et al., "A Fast Normalized Cross-Correlation Method for Motion Estimation", IEEE Transactions, Ultrasonics, Ferroelectrics and Frequency Control, 57(6):1347-1357 (2010).
Luo, et al., "High-Frame Rate, Full-View Myocardial Elastography With Automated Contour Tracking In Murine Left Ventricles In Vivo", IEEE Transactions, Ultrasonics, Ferroelectrics and Frequency Control, 55(1):240-248 (2008).
Luo, et al., "Myocardial Elastography At Both High Temporal and Spatial Resolution for the Detection of Infarcts", Ultrasound Med. Biol., 33(8):1206-1223 (2007).
Luo, et al., "Pulse Wave Imaging of Normal and Aneurysmal Abdominal Aortas In Vivo", IEEE Trans. Med. Imaging, 28(4):477-486 (2009).

Maleke, et al., "In Vivo Feasibility of Real-Time Monitoring of Focused Ultrasound Surgery (FUS) Using Harmonic Motion Imaging (HMI)", IEEE Trans. Biomed. Eng., 57(1):7-11 (2010).
Maleke, et al., "Single-Element Focused Ultrasound Transducer Method for Harmonic Motion Imaging", Ultrasonic Imaging, 28(3):144-158 (2006).
Marquet, et al., "Non-Invasive Transcranial Ultrasound Therapy Based on a 3D CT Scan: Protocol Validation and In Vitro Results", Phys. Med. Biol., 54:2597-2613 (2009).
Mazziotta, et al., "A Probabilistic Atlas of the Human Brain: Theory and Rationale for Its Development the International Consortium For Brain Mapping (ICBM)", Neuroimage, 2:89-101 (1995).
McDannold, et al., "Blood-Brain Barrier Disruption Induced by Focused Ultrasound and Circulating Preformed Microbubbles Appears to be Characterized by the Mechanical Index", Ultrasound Med Biol., 34(5):834-840 (2008).
McDannold, et al., "MRI-Guided Targeted Blood-Brain Barrier Disruption With Focused Ultrasound: Histological Findings In Rabbits", Ultrasound Med. Biol., 31(11):1527-1537 (2005).
McDannold, et al., "Targeted Disruption of the Blood-Brain Barrier With Focused Ultrasound: Association With Cavitations Activity", Physics in Medicine and Biology, 51:793-808 (2006).
McDannold, et al., "Use of Ultrasound Pulses Combined With Definity for Targeted Blood-Brain Barrier Disruption: A Feasibility Study", Ultrasound In Medicine & Biology, 33(4):584-590 (2007).
McLaughlin, et al., "Piezoelectric Sensor Determination of Arterial Pulse Wave Velocity", Physiol Meas., 24(3):693-702 (2003).
McNally, et al., "Computer Vision Elastography: Speckle Adaptive Motion Estimation for Elastography Using Ultrasound Sequences", IEEE Transactions on Medical Imaging, 24(6):755-766 (2005).
Melodelima, et al., "Thermal Ablation by High-Intensity-Focused Ultrasound Using a Toroid Transducer Increases the Ccagulated Volume. Results of Animal Experiments", Ultrasound in Medicine & Biology, 35(3):425-435 (2009).
Mitri, et al., "Chirp Imaging Vibro-Acoustography for Removing the Ultrasound Standing Wave Artifact", IEEE Transactions on Medical Imaging, 24(10):1249-1255 (2005).
Mychaskiw, et al., "Optison (FS069) Disrupts the Blood-Brain Barrier in Rats", Anesthesia & Analgesia, 91:798 (2000).
Nichols, et al., "Vascular Impedance. In McDonald's: Blood Flow in Arteries: Theoretical, Experimental and Clinical Principles", E. Arnold. London, Oxford University Press, Table of Contents (1998).
Niels et al., "Transmural Ultrasound-based Visualization of Patters of Action Potential Wave Propagation in Cardiac Tissue," Annals of Biomedical Engineering 38(10):3112-3123 (2010).
Ophir, et al., "Elastography: A Quantitative Method for Imaging the Elasticity of Biological Tissues", Ultrasonic Imaging, 3(2):111-134 (1991).
Otani, "Use of ultrasound imaging to map propagating action potential waves in the heart", Computers in Cardiology, 36:617-620 (2009).
Otani, et al., "Transmural Ultrasound-Based Visualization of Patterns of Action Potential Wave Propagation in Cardiac Tissue", Annals Biomedical Engineering, 38(10):3112-3123 (2010).
Palmeri, et al., "Characterizing acoustic attenuation of homogeneous media using focused impulsive acoustic radiation force", Ultrason Imaging, 28(2):114-128 (2006).
Papadakis, Emmanuel P., "Ultrasonic Instruments & Devices", Academic Press, 8 pages (1999).
Pardridge, "Drug Targeting to the Brain", Pharmaceutical Research, 24:1733-1744 (2007).
Pardridge, "The Blood-Brain Barrier: Bottleneck in Brain Drug Development", NeuroRx, 2:3-14 (2005).
Parker, "Ultrasonic-attenuation and absorption in liver-tissue", Ultrasound Med Biol 1983; 9:363-9.
Patel, et al., "GDNF Delivery for Parkinson's Disease", ACTA Neurochirurgica-Supplementum, 97(2):135-154 (2007).
Pernot, et al., "ECG-Gated, Mechanical and Electromechanical Wave Imaging of Cardiovascular Tissues In Vivo", Ultrasound in Medicine & Biology, 33(7):1075-1085 (2007).
Pernot, et al., "Electromechanical Imaging of the Myocardium at Normal and Pathological States", 2005 IEEE Ultrasonics Symposium, pp. 1091-1094 (2005).

(56) References Cited

OTHER PUBLICATIONS

Philippens, "Non-Human Primate Models for Parkinson's Disease", Drug Discovery Today: Disease Models, 5:105-111 (2008).
Pichardo, et al., "Multi Frequency Characterization of Speed of Sound for Longitudinal Transmission on Freshly Excised Human Skulls", 9th International Society on Therapeutic Ultrasound, p. 136 (2009).
Prinzen, et al., "The Time Sequence of Electrical and Mechanical Activation During Spontaneous Beating and Ectopic Stimulation", Eur. Heart J., 13:535-543 (1992).
Provost, et al., "Electromechanical Wave Imaging of Normal and Ischemic Hearts In Vivo", IEEE Trans. Med. Imaging, 29:625-635 (2010).
Provost, et al., "Imaging the electromechanical activity of the heart in vivo", PNAS, 108(21):8565-8570 (2011).
Provost, et al., "Mapping of cardiac electrical activation with electromechanical wave imaging: An in silico-in vivo reciprocity study", Heart Rhythm., 8(5):752-759 (2011).
Qin, et al., "Acoustic Response of Compliable Microvessels Containing Ultrasound Contrast Agents", Phys. Med. Biol., 51:5065-5088 (2006).
Qin, et al., "The Natural Frequency of Nonlinear Oscillation of Ultrasound Contrast Agents in Microvessels", Ultrasound in Med. & Biol., 33(7):1140-1148 (2007).
Ramanathan, et al., "Activation and Repolarization of the Normal Human Heart Under Complete Physiological Conditions", Proceedings of the National Academy of Sciences, 103:6309-6314 (2006).
Ramanathan, et al., "Noninvasive Electrocardiographic Imaging for Cardiac Electrophysiology and Arrhythmia", Nat Med., 10:422-428 (2004).
Raymond, et al., "Ultrasound Enhanced Delivery of Molecular Imaging and Therapeutic Agents in Alzheimer's Disease Mouse Models", PLoS One, 3(5):e2175 (2008).
Rice, et al., "Approximate Model of Cooperative Activation and Crossbridge Cycling in Cardiac Muscle Using Ordinary Differential Equations", Biophys. J., 95:2368-2390 (2008).
Rockenstein, et al., "Transgenic Animal Models of Neurodegenerative Diseases and Their Application to Treatment Development", Adv. Drug Del. Rev., 59(11):1093-1102 (2007).
Rogers, et al., "Age-Associated Changes in Regional Aortic Pulse Wave Velocity", J Am Coll Cardiol., 38(4):1123-1129 (2001).
Roth, "Influence of a Perfusing Bath on the Foot of the Cardiac Action Potential", Circulation Research, 86:E19-E22 (2000).
Sabraoui, et al., "Feedback Loop Process to Control Acoustic Cavitation", Ultrasonics Sonochemistry, 18(2):589-594 (2011).
Samuel, et al., "An Ex Vivo Study of the Correlation Between Acoustic Emission and Microvascular Damage", Ultrasound Med. Biol., 35(9):1574-1586 (2009).
Sanberg, et al., "Brief Communication: Neural Transplants Disrupt the Blood-Brain Barrier and Allow Peripherally Acting Drugs to Exert a Centrally Mediated Behavioral Effect", Experimental Neurology, 102:149-152 (1988).
Sandrin, et al., "Time-Resolved Pulsed Elastography with Ultrafast Ultrasonic Imaging", Ultrason. Imaging, 21(4):259-72 (1999).
Sarvazyan, et al., "Shear Wave Elasticity Imaging: A New Ultrasonic Technology of Medical Diagnostics", Ultrasound Med Biol., 24(9):1419-1435 (1998).
Sassaroli, et al., "Cavitation Threshold of Microbubbles in Gel Tunnels by Focused Ultrasound", Ultrasound in Med. & Biol., 33(10):1651-1660 (2007).
Sassaroli, et al., "Forced Linear Oscillations of Microbubbles in Blood Capillaries", J. Acoust. Soc. Am., 115(6):3235-3243 (2004).
Sassaroli, et al., "Resonance Frequency of Microbubbles in Small Blood Vessels: a Numerical Study", Phys. Med. Biol., 50:5293-5305 (2005).
Schenk, et al., "Immunization With Amyloid-Beta Attenuates Alzheimer-Disease-Like Pathology in the PDAPP Mouse", Nature, 400:173-177 (1999).
Scher, et al., "The Pathway of Ventricular Depolarization in the Dog", Circ Res., 4:461-469 (1956).
Schilling, et al., "Simultaneous Endocardial Mapping in the Human Left Ventricle Using a Noncontact Catheter: Comparison of Contact and Reconstructed Electrograms During Sinus Rhythm", Circulation, 98:887-898 (1998).
Sengupta, et al., "Electromechanical Activation Sequence in Normal Heart", Heart Fail Clin., 4:303-314 (2008).
Shehata, et al., "Myocardial Tissue Tagging With Cardiovascular Magnetic Resonance", Journal of Cardiovascular Magnetic Resonance, 11:55 (2009).
Sheikov, et al., "Brain Arterioles Show More Active Vesicular Transport of Blood-Borne Tracer Molecules Than Capillaries and Venules After Focused Ultrasound-Evoked Opening of the Blood-Brain Barrier", Ultrasound Med. Biol., 32(9):1399-1409 (2006).
Sheikov, et al., "Cellular Mechanisms of the Blood-Brain Barrier Opening Induced by Ultrasound in Presence of Microbubbles", Ultrasound Med. Biol., 30(7):979-989 (2004).
Sheikov, et al., "Effect of Focused Ultrasound Applied With an Ultrasound Contrast Agent on the Tight Junctional Integrity of the Brain Microvascular Endothelium", Ultrasound Med. Biol., 34(7):1093-1104 (2008).
Shiina, et al., "Realtime tissue elasticity imaging using the combined autocorrelation method", J. Med. Ultrasonics, 29(autumn):119-128 (2002).
Siegel, et al., "Neurotrophic Factors in Alzheimer's and Parkinson's Disease Brain", Brain Research Reviews, 33:199-227 (2000).
Silva, "Nanotechnology Approaches to Crossing the Blood-Brain Barrier and Drug Delivery to the CNS", BMC Neruosci., 9(Suppl 3): S4 (2008).
Sinkus, et al., "High-Resolution Tensor MR Elastography for Breast Tumour Detection", Phys Med Biol., 45(6):1649-1664 (2000).
Sirsi, et al., "Effect of Microbubble Size on Fundamental Mode High Frequency Ultrasound Imaging in Mice", Ultrasound in Med. & Bio., 36(6):935-948 (2010).
Spach, et al., "Extracellular Discontinuities in Cardiac Muscle—Evidence for Capillary Effects on the Action Potential Foot", Circulation Research, 83:1144-1164 (1998).
Spalazzi, et al., "Elastographic Imaging of Strain Distribution within the Anterior Cruciate Ligament and at the ACL-Bone Insertions", IEEE Ultrasonics Symposium, Sep. 2005, pp. 1755-1758.
Stewart, et al., "Blood-Eye Barriers in the Rat: Correlation of Ultrastructure With Function", J. Comp. Neurol., 340(4):566-576 (1994).
Stieger, et al., "Enhancement of Vascular Permeability With Low-Frequency Contrast-Enhanced Ultrasound in the Chorioallantoic Membrane Model", Radiology, 243(1): 112-121 (2007).
Styner, et al., "Automatic Brain Segmentation in Rhesus Monkeys", 2007 Medical Imaging, Proc. of SPIE, 6512:65122L-1-65122L-8 (2007).
Sutherland, "Color Doppler Myocardial Imaging—Potential Applications in Acquired and Congenital Heart-Disease", Acta Paediatr., 84:40-48 (1995).
Suzuki, et al., "Dependence of ultrasonic attenuation of liver on pathologic fat and fibrosis: examination with experimental fatty liver and liver fibrosis models", Ultrasound Med Biol 1992; 18:657-666.
Sykova, et al., "Diffusion in Brain Extracellular Space", Physiol. Rev., 88(4):1277-1340 (2008).
Talu, et al., "Tailoring the Size Distribution of Ultrasound Contrast Agents: Possible Method for Improving Sensitivity in Molecular Imaging" Mol. Imag., 6(6):384-392 (2007).
Tang, et al., "Standing-Wave Suppression for Transcranial Ultrasound by Random Modulation", IEEE transactions on Biomedical Engineering, 57(1):203-205 (2010).
Tanter, et al., "Focusing and Steering Through Absorbing and Aberrating Layers: Application To Ultrasonic Propagation Through the Skull", The Journal of the Acoustical Society of America, 103:2403-2410 (1998).
Tanter, et al., "Ultrafast Compound Imaging for 2-D Motion Vector Estimation: Application to Transient Elastography", IEEE Trans Ultrason Ferroelectr Freq Control, 49(10):1363-1374 (2002).
Tavarozzi, et al., "Magnetocardiography: Current Status and Perspectives Part II: Clinical Applications", Ital Heart J., 3:151-165 (2002).

(56) References Cited

OTHER PUBLICATIONS

Techavipoo, et al., "Temperature dependence of ultrasonic propagation speed and attenuation in excised canine liver tissue measured using transmitted and reflected pulses", The Journal of Acoustical Society of America, 115(6):2859-2865 (2004).
Treat, et al., "Targeted Delivery of Doxorubicin to the Rat Brain at Therapeutic Levels Using MRI-Guided Focused Ultrasound", Int. J. Cancer, 121(4):901-907 (2007).
Tung, et al., "Feasibility of Noninvasive Cavitation-Guided Blood-Brain Barrier Opening Using Focused Ultrasound and Microbubbles in Nonhuman Primates", Applied Physics Letters, 98(16):163704 (2001).
Tung, et al., "Identifying the Inertial Cavitation Threshold and Skull Effects in a Vessel Phantom Using Focused Ultrasound and Microbubbles", Ultrasound in Medicine & Biology, 36(5):840-852 (2010).
Tung, et al., "Identifying the Inertial Cavitation Threshold in a Vessel Phantom Using Focused Ultrasound and Microbubbles", The Journal of the Acoustical Society of America, 124:2486 (2008).
Tung, et al., "Noninvasive In Vivo Cavitation Threshold Detection During Blood-Brain Barrier Opening Using Focused Ultrasound and the Contrast Agent and Definity", Joint 159th Meeting of the Acoustic Society of America, (Apr. 19, 2010).
Tuszynski, et al., "A Phase 1 Clinical Trial of Nerve Growth Factor Gene Therapy for Alzheimer Disease", Nature Medicine, 11:551-555 (2005).
Tuszynski, et al., "Nerve Growth Factor Gene Therapy in Alzheimer Disease", Alzheimer Disease & Associated Disorders, 21:179-189 (2007).
Tyreus, et al., "Two-dimensional acoustic attenuation mapping of high-temperature interstitial ultrasound lesions", Phys Med Biol 49:533-46 (2004).
Unger, E.C. et al., "Therapeutic Applications of Lipid-Coated Microbubbles", Advanced Drug Delivery Reviews, 56(9):1291-1314 (2004).
Vappou, et al., "Quantitative Viscoelastic Parameters Measured by Harmonic Motion Imaging", Phys. Med. Biol., 54:3579-3595 (2009).
Walker, et al., "A Fundamental Limit on Delay Estimation Using Partially Correlated Speckle Signals", IEEE Transactions, Ultrasonics, Ferroelectrics and Frequency Control, 42(2):301-308 (1995).
Walker, et al., "A Fundamental Limit on the Performance of Correlation Based Phase Correction and Flow Estimation Techniques", IEEE Transactions, Ultrasonics, Ferroelectrics and Frequency Control, 41(5):644-654 (1994).
Wang et al., "Qualitative and Quantitative Analysis of the Molecular Delivery Through the Ultrasound-Enhanced Blood-Brain Barrier Opening in the Murine Brain," presented at the IEEE Symp. Ultrason. Ferroelectr. Freq. Control, Beijing, China, 2008.
Wang, et al., "A Composite High-Frame-Rate System for Clinical Cardiovascular Imaging", IEEE Transactions, Ultrasonics, Ferroelectrics and Frequency Control, 55(10):2221-2233 (2008).
Wang, et al., "A Composite Imaging Technique for High Frame-Rate and Full-View Cardiovascular Ultrasound and Elasticity Imaging", IEEE International Ultrasonics Symposium, New York, NY, Oct. 28-31, 2007.
Wang, et al., "Increased Aortic Stiffness Assessed by Pulse Wave Velocity in Apolipoprotein E-Deficient Mice", Am J Physiol Heart Circ Physiol., 278(2):H428-34 (2000).
Wenk, "A Primate Model of Alzheimer's Disease", Behavioural Brain Research, 57:117-122 (1993).
White, et al., "Longitudinal and Shear Mode Ultrasound Propagation in Human Skull Bone", Ultrasound in Medicine & Biology, 32:1085-1096 (2006).
Wyman, et al., "Mapping Propagation of Mechanical Activation in the Paced Heart With MRI Tagging", Am J Physiol Heart Circ Physiol, 276:H881-891 (1999).
Xu, et al., "Controllable Gas-Liquid Phase Flow Patterns and Monodisperse Microbubbles in a Microfluidic T-Junction Device", Appl. Phys. Lett., 88(13):133506-1-133506-3 (2006).
Yin, et al., "A Numerical Study of Transcranial Focused Ultrasound Beam Propagation at Low Frequency", Physics in Medicine and Biology, 50:1821-1836 (2005).
Yuh, et. al. "Delivery of Systemic Chemotherapeutic Agent to Tumors by Using Focused Ultrasound: Study in a Murine Model", Radiology, 234(2):431-437 (2005).
Zerhouni, et al., "Human Heart: Tagging with MR Imaging—A Method for Noninvasive Assessment of Myocardial Motion", Radiology, 169(1):59-63 (1988).
Zhang, et al., "Noninvasive Three-Dimensional Electrocardiographic Imaging of Ventricular Activation Sequence", Am J Physiol Heart Circ Physiol., 289:H2724-32 (2005).
Zheng, et al. "High Resolution Ultrasound Elastomicroscopy Imaging of Soft Tissues: System Development and Feasibility; Ultrasound Elastomicroscopy", Physics in Medicine and Biology, 49(17):3925-3938 (2004).
Zheng, et al., "Ultrasonic measurement of depth-dependent transient behaviors of articular cartilage under compression", Journal of Biomechanics, 38:1830-1837 (2005).
Zheng, et al., "Ultrasound-Driven Microbubble Oscillation and Translation Within Small Phantom Vessels", Ultrasound Med. Biol., 33(12):1978-1987 (2007).
Zlokovic, "The Blood-Brain Barrier in Health and Chronic Neurodegenerative Disorders", Neuron, 57(2):178-201 (2008).
Zwanenburg, et al., "Timing of Cardiac Contraction in Humans Mapped by High-Temporal-Resolution MRI Tagging: Early Onset and Late Peak of Shortening in Lateral Wall", Am J Physiol Heart Circ Physiol., 286:H1872-1880 (2004).
U.S. Appl. No. 14/457,023 (US 2015/0045724), filed Aug. 11, 2014 (Feb. 12, 2015).
U.S. Appl. No. 14/476,543 (U.S. Pat. No. 10,028,723), filed Sep. 3, 2014 (Jul. 24, 2018).
U.S. Appl. No. 14/949,000 (US 2016/0074678), filed Nov. 23, 2015 (Mar. 17, 2016).
U.S. Appl. No. 14/449,820, filed Jul. 23, 2018 Final Office Action.
U.S. Appl. No. 14/449,820, filed Nov. 29, 2017 Response to Non-Final Office Action.
U.S. Appl. No. 14/449,820, filed Mar. 2, 2017 Non-Final Office Action.
U.S. Appl. No. 14/949,000, filed Feb. 28, 2018 Non-Final Office Action.
U.S. Appl. No. 14/949,000, filed Jan. 29, 2018 Amendment and Request for Continued Examination (RCE).
U.S. Appl. No. 14/949,000, filed Jul. 28, 2017 Final Office Action.
U.S. Appl. No. 14/695,674, filed Mar. 15, 2018 Final Office Action.
U.S. Appl. No. 14/695,674, filed Feb. 2, 2018 Response to Non-Final Office Action.
U.S. Appl. No. 14/695,674, filed Nov. 3, 2017 Non-Final Office Action.
U.S. Appl. No. 14/091,010, filed Jul. 3, 2018 Final Office Action.
U.S. Appl. No. 14/091,010, filed Jun. 1, 2018 Response to Non-Final Office Action.
U.S. Appl. No. 14/091,010, filed Dec. 1, 2017 Non-Final Office Action.
U.S. Appl. No. 14/091,010, filed Oct. 18, 2017 Amendment and Request for Continued Examination (RCE).
U.S. Appl. No. 14/091,010, filed Apr. 20, 2017 Final Office Action.
U.S. Appl. No. 14/091,010, filed Mar. 13, 2017 Response to Non-Final Office Action.
U.S. Appl. No. 14/457,023, filed May 2, 2018 Final Office Action.
U.S. Appl. No. 14/457,023, filed Dec. 26, 2017 Response to Non-Final Office Action.
U.S. Appl. No. 14/457,023, filed Jun. 23, 2017 Non-Final Office Action.
U.S. Appl. No. 14/457,023, filed Mar. 9, 2017 Amendment and Request for Continued Examination (RCE).
U.S. Appl. No. 14/476,543, filed Jun. 22, 2018 Issue Fee Payment.
U.S. Appl. No. 14/476,543, filed Mar. 22, 2018 Notice of Allowance.
U.S. Appl. No. 14/476,543, filed Jan. 17, 2018 Amendment and Request for Continued Examination (RCE).
U.S. Appl. No. 14/476,543, filed Jul. 17, 2017 Final Office Action.

(56) References Cited

OTHER PUBLICATIONS

U.S. Appl. No. 14/476,543, filed Mar. 22, 2017 Response to Non-Final Office Action.
Sheeran et al., "Formulation and Acoustic Studies of a New Phase-Shift Agent for Diagnostic and Therapeutic Ultrasound," Langmuir, 27(17):10412-10420 (2011).
U.S. Appl. No. 14/449,820, filed Jul. 8, 2019 Non-Final Office Action.

* cited by examiner

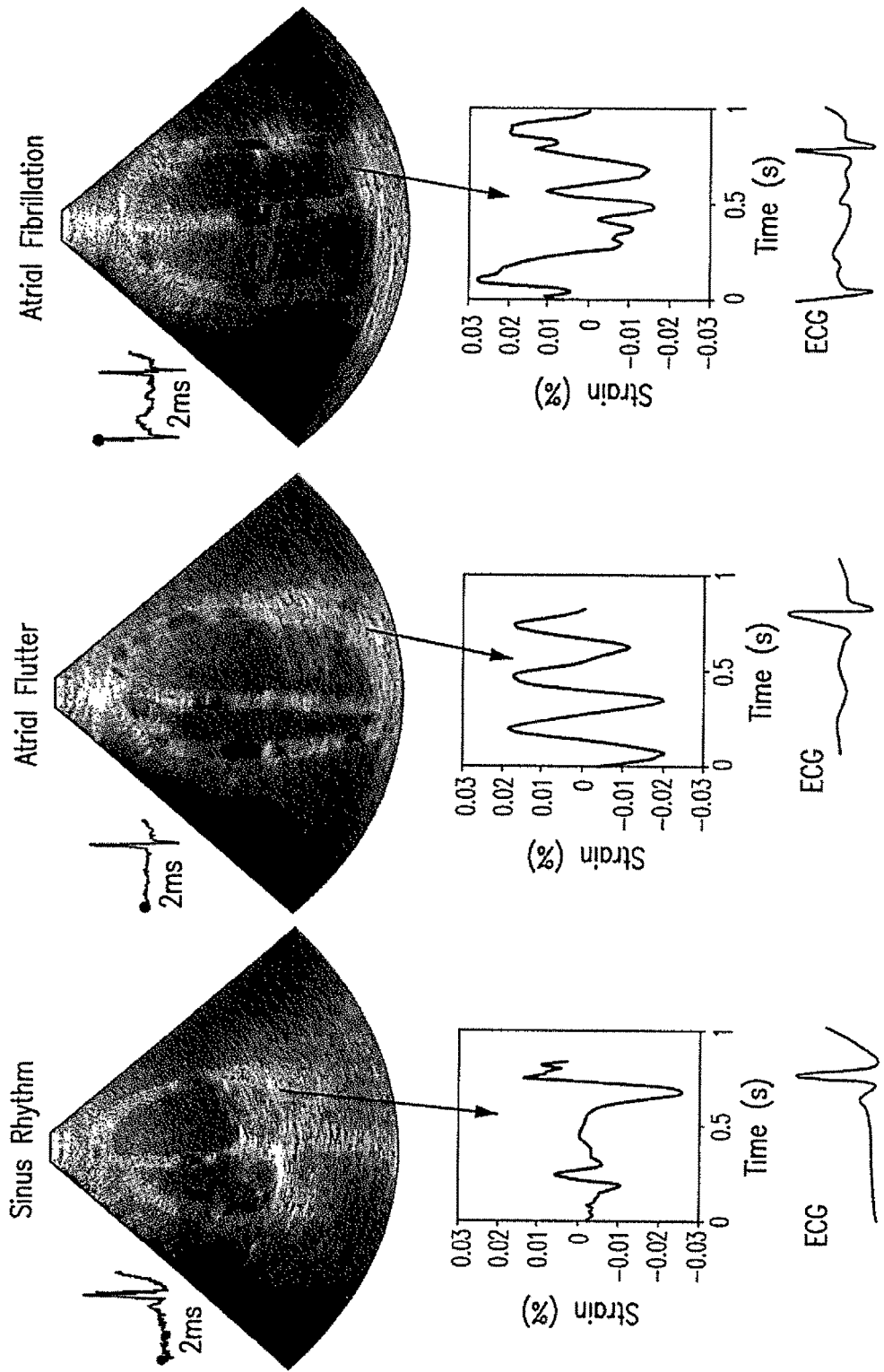

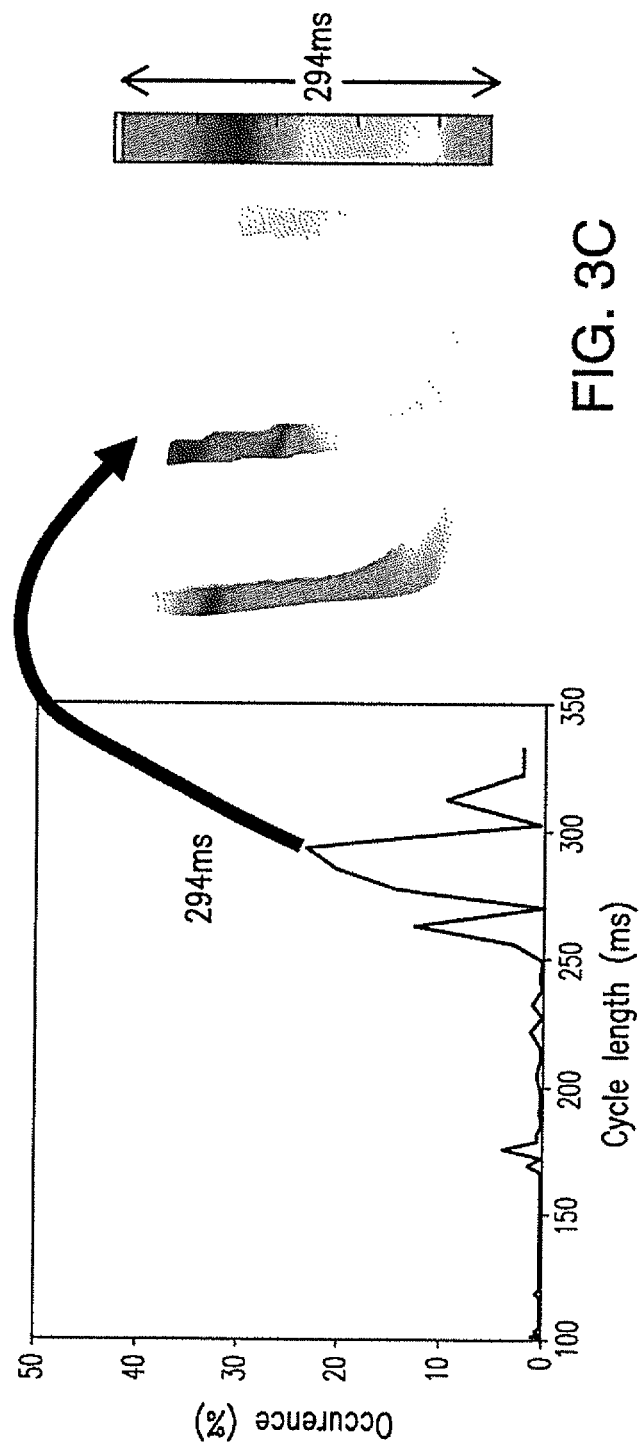

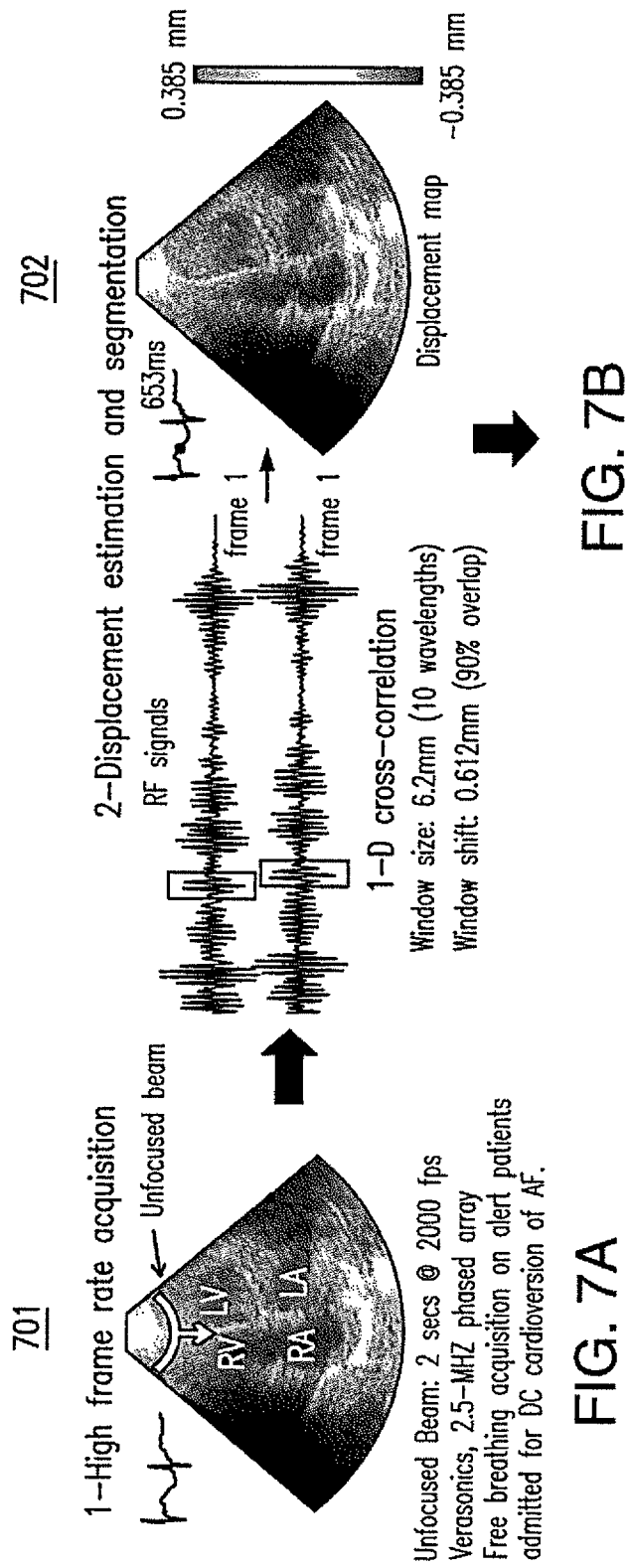

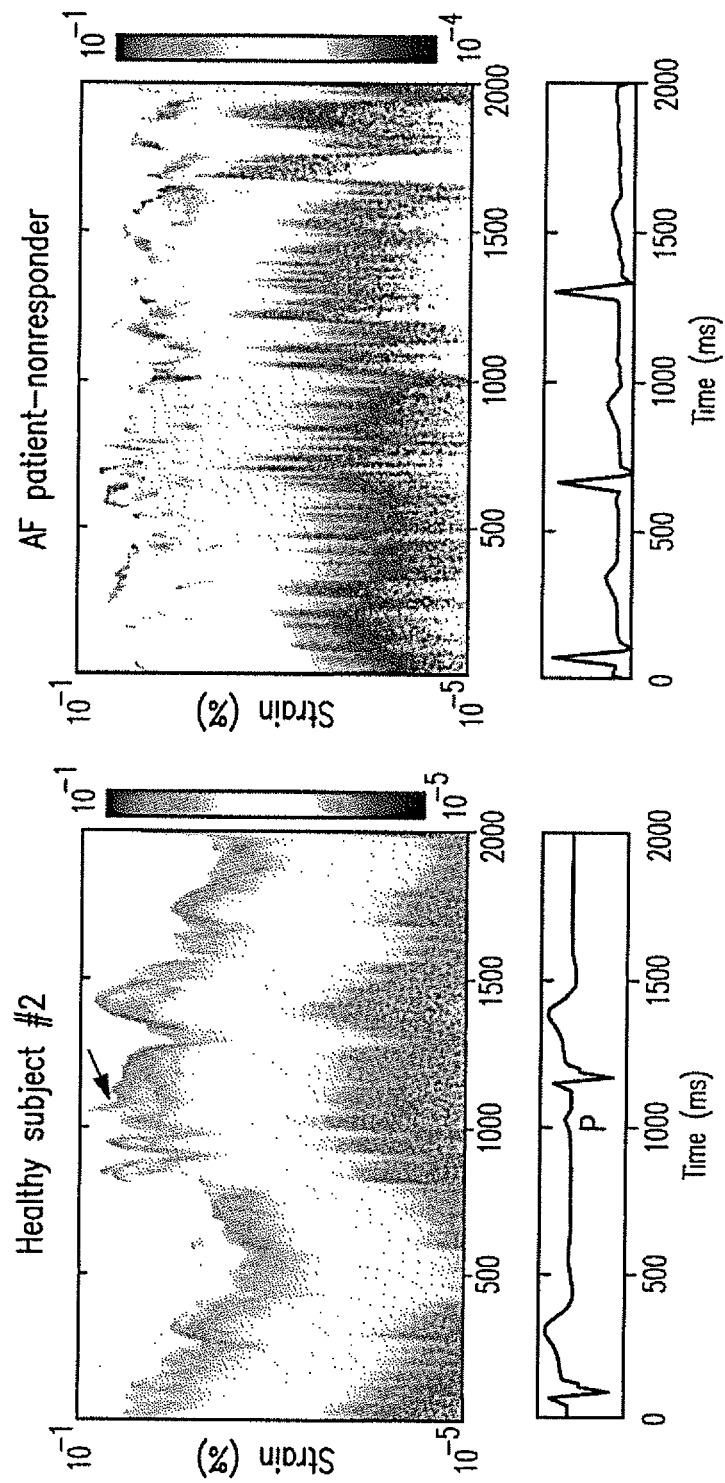

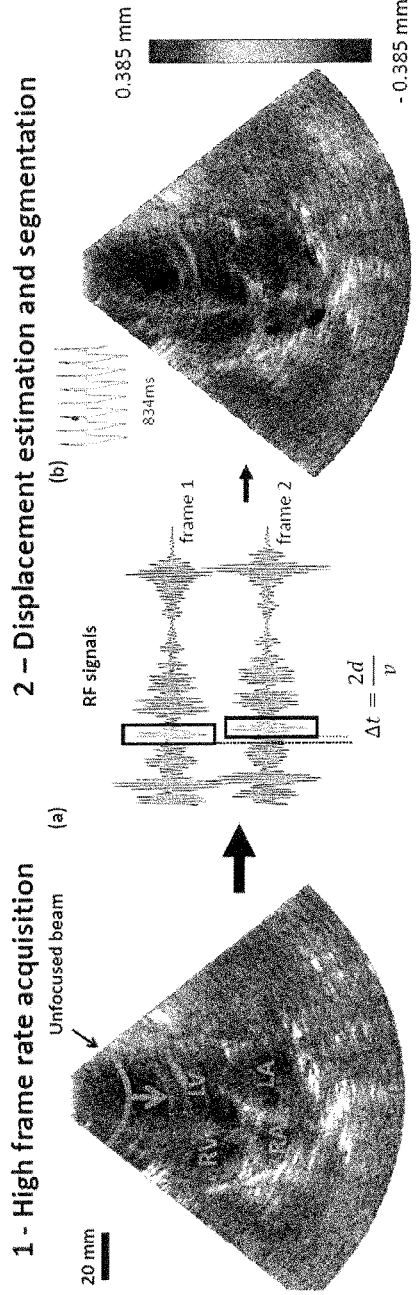
FIG. 11-1
1 - High frame rate acquisition
FIG. 11-2(a)    FIG. 11-2(b)
2 - Displacement estimation and segmentation
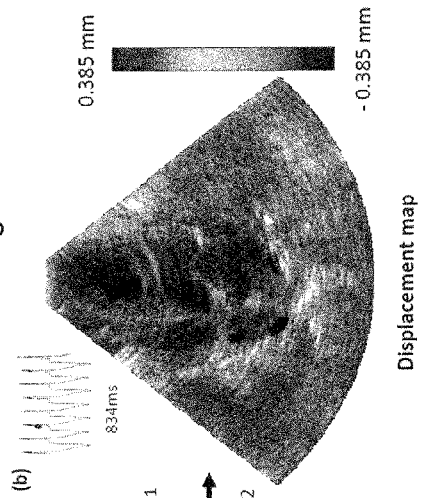
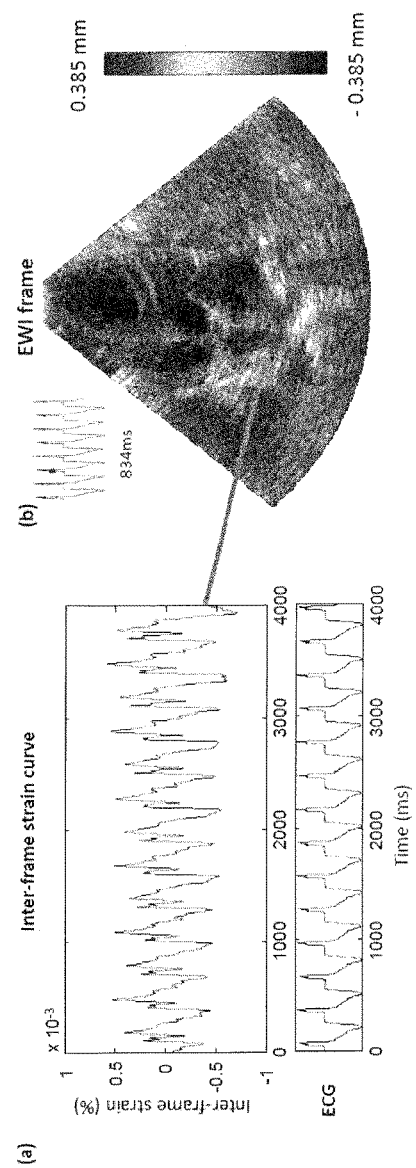
3 - Axial electromechanical strain estimation
FIG. 11-3(a)
FIG. 11-3(b)

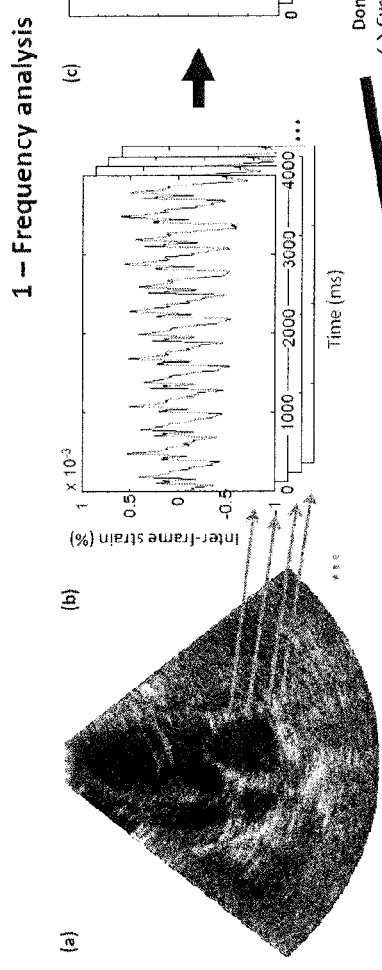
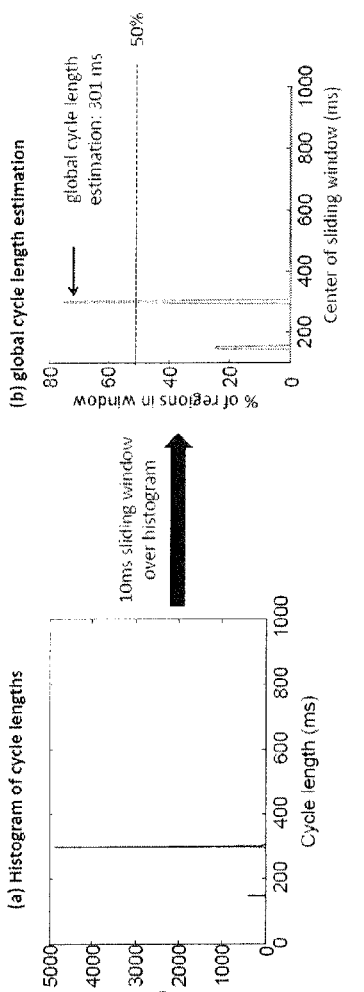
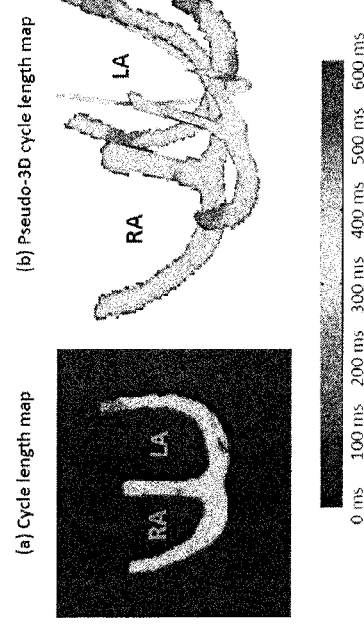
FIG. 12-1(a)    FIG. 12-1(b)    FIG. 12-1(c)
FIG. 12-2(a)    FIG. 12-2(b)
FIG. 12-3(a)    FIG. 12-3(b)

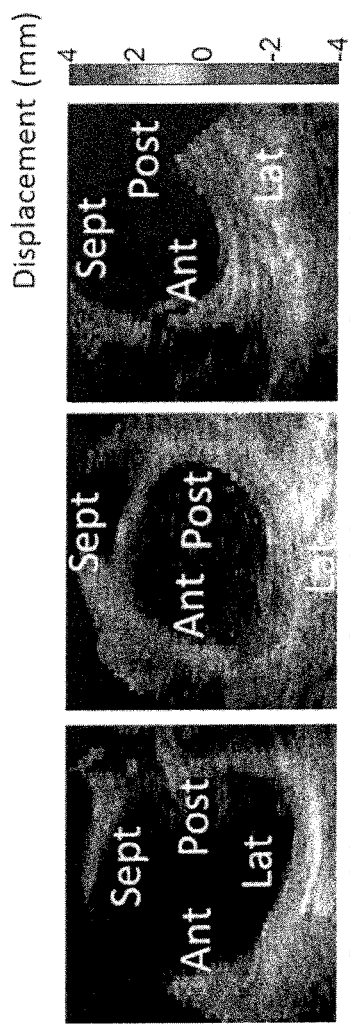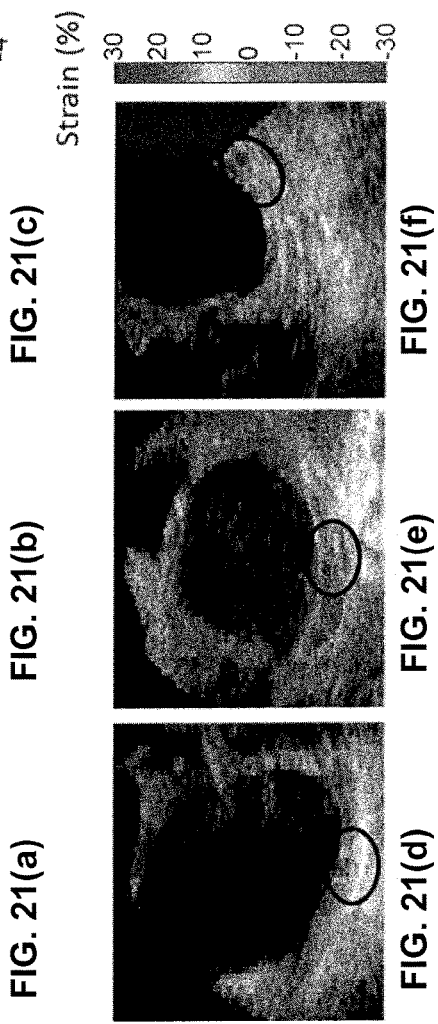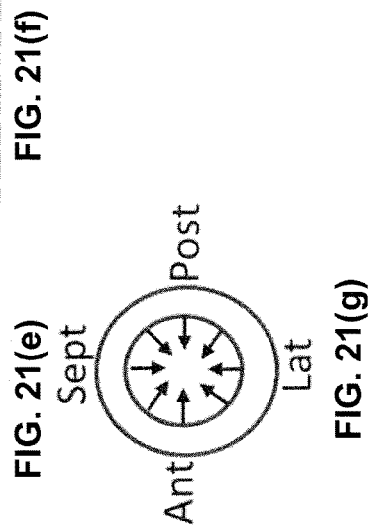
FIG. 21(a) FIG. 21(b) FIG. 21(c) FIG. 21(d) FIG. 21(e) FIG. 21(f) FIG. 21(g)

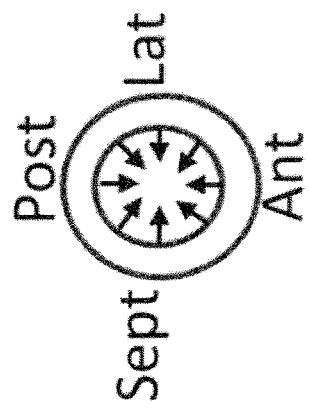
FIG. 22(c)
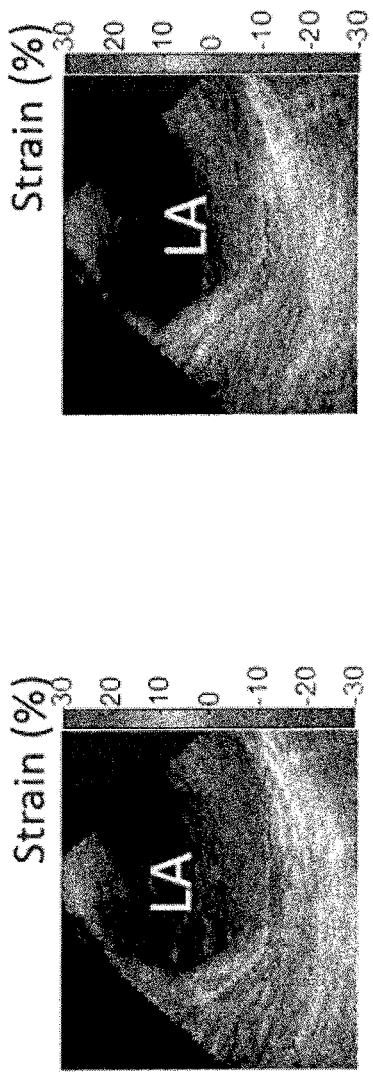
FIG. 22(b)
FIG. 22(a)
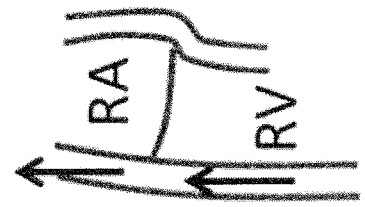
FIG. 22(f)
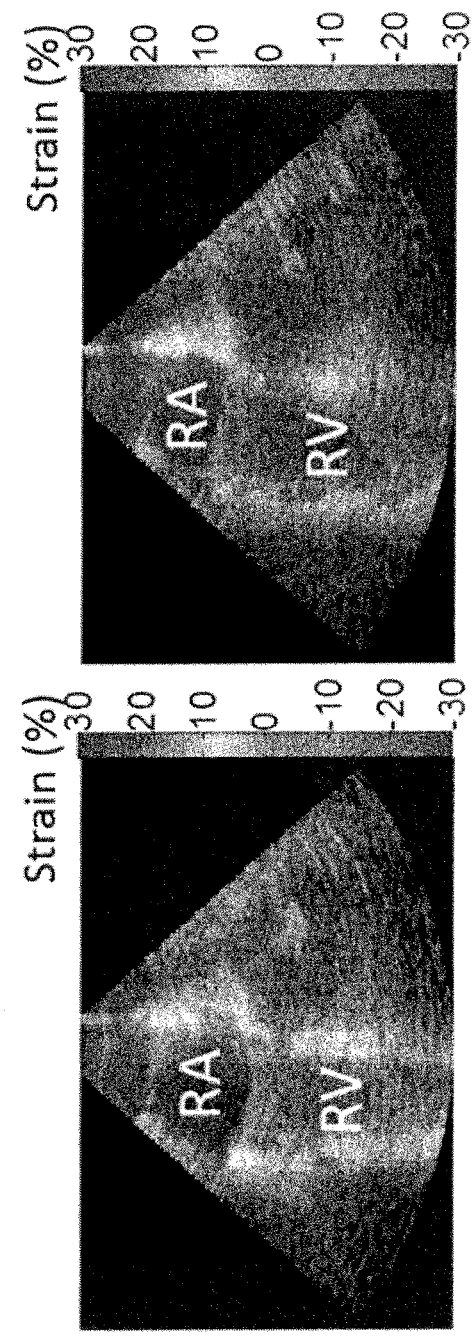
FIG. 22(e)
FIG. 22(d)

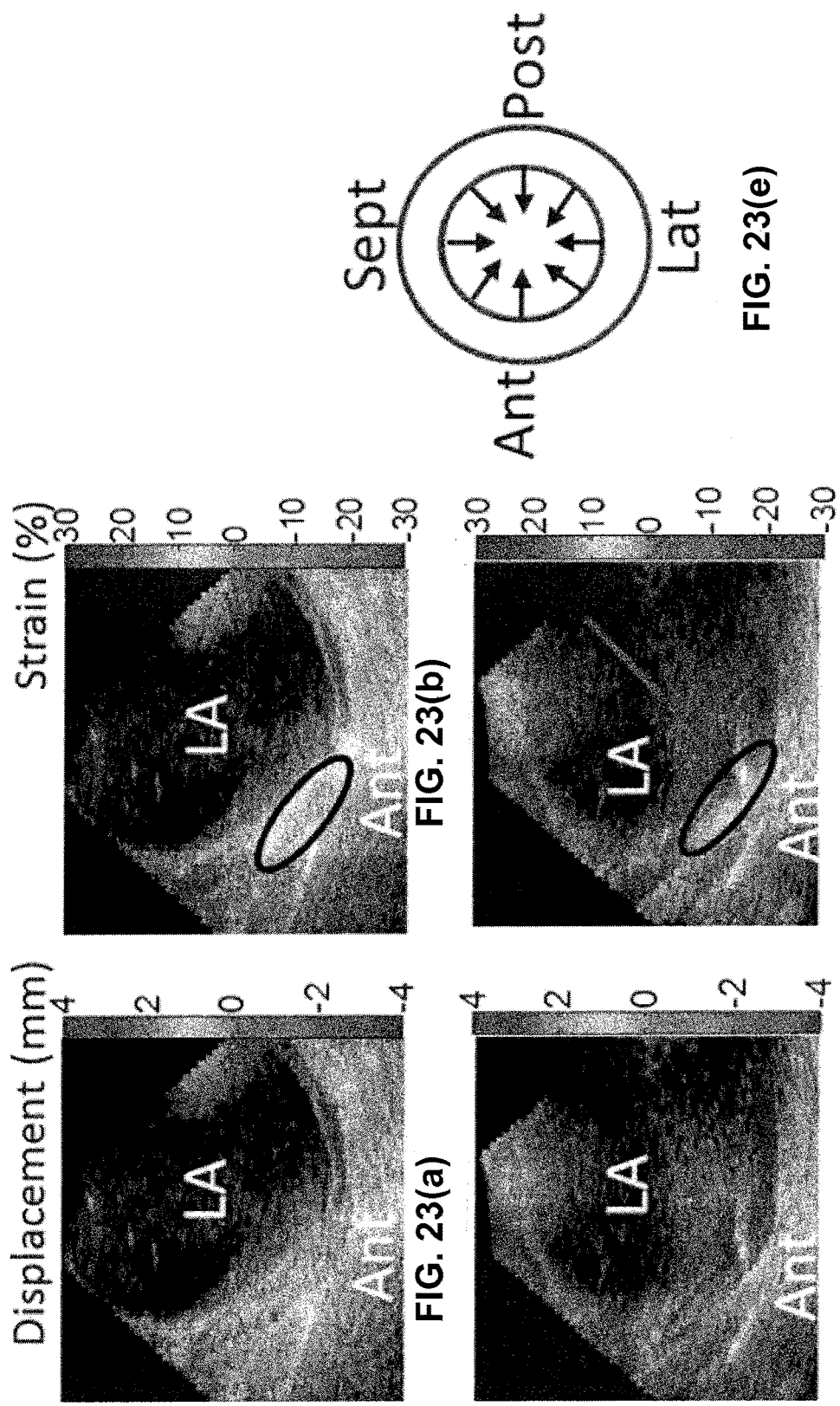

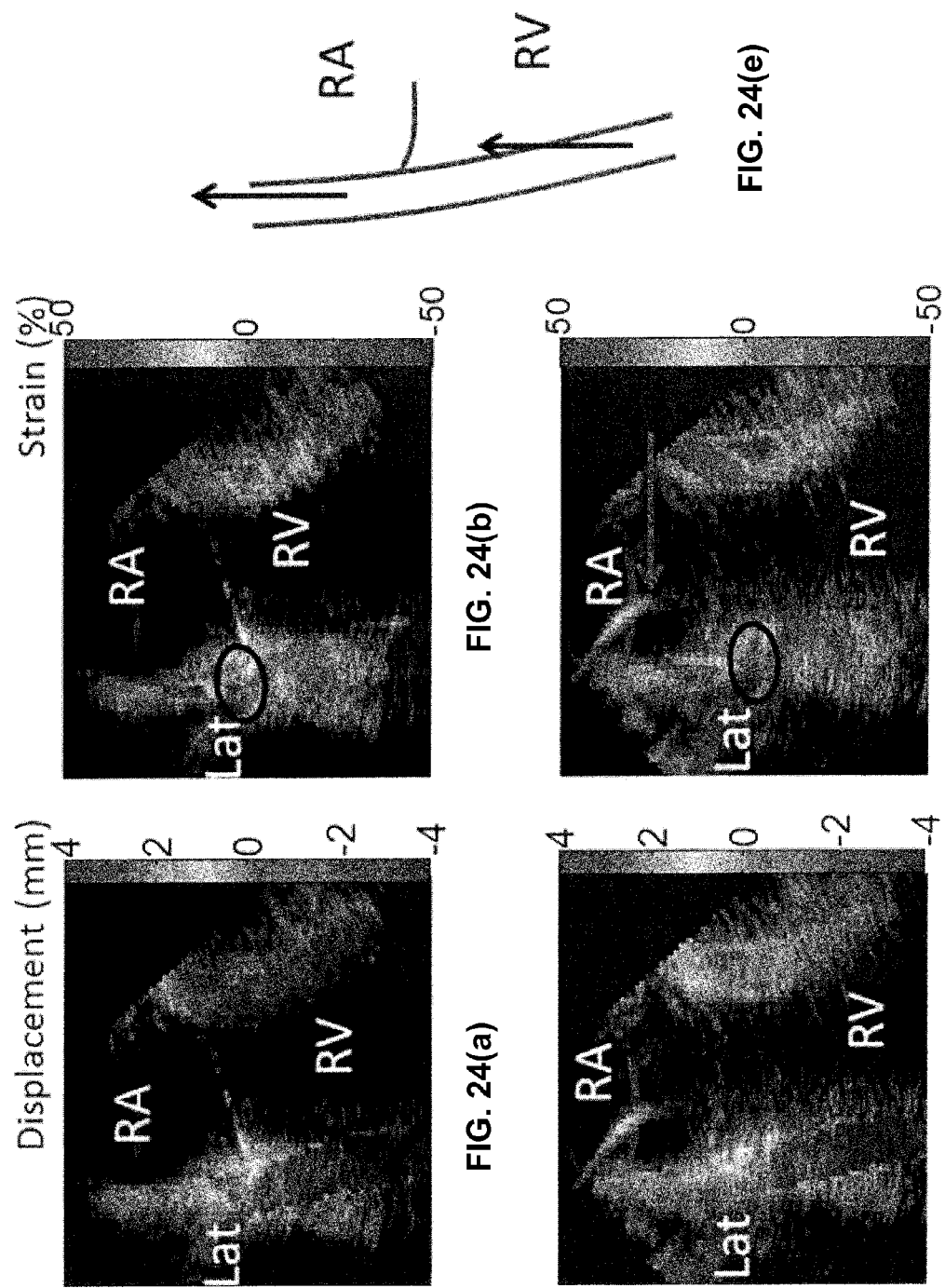

SYSTEMS AND METHODS FOR MECHANICAL MAPPING OF CARDIAC RHYTHM

CROSS REFERENCE TO RELATED APPLICATIONS

This application is a continuation-in-part of PCT/US13/64377, filed Oct. 10, 2013, which claims priority to U.S. Provisional Patent Application No. 61/712,057, filed Oct. 10, 2012, each of which is incorporated by reference herein in its entirety.

STATEMENT REGARDING FEDERALLY-SPONSORED RESEARCH

This invention was made with government support from the National Institutes of Health under Grant Nos. R01HL114358, R01EB006042 and R21HL096094. The government has certain rights in the invention.

BACKGROUND

Certain heart arrhythmias, including atrial fibrillation, can cause disability and/or death. The mechanics of the heart can be a factor in the onset and perpetuation of arrhythmias.

Certain ultrasound imaging systems can achieve ultra-high frame rates, e.g., 2000-5000 frames/s, compared with 50-200 frames/s in commercial clinical systems for the depths utilized for transthoracic cardiac applications. Such frame rates can allow for both improved temporal resolution, and motion and deformation mapping. For example, using such techniques, mapping the transient strains occurring in response to the electrical activation, i.e., the electromechanical wave, can be used to map the transmural activation sequence of the normal heart and to locate pacing sites in patients undergoing cardiac resynchronization therapy. Certain of such and related techniques are shown and described, for example and without limitation, in U.S. Patent Application Publication Nos. 2008/0285819 and 2007/0049824, each of which is incorporated by reference herein in its entirety.

However, there is an opportunity for improved systems and techniques for mechanical mapping of cardiac rhythm, including systems and techniques utilizing the spatio-temporal evolution of the local deformations of the heart during e.g., focal tachycardia, flutter, and fibrillation.

SUMMARY

Systems and methods for mapping behavior of electromechanical systems are disclosed herein.

In one embodiment of the disclosed subject matter, a method for mapping behavior of a heart includes acquiring a series of two or more images of the heart. The series of images can be taken at one or more pixel locations, each pixel location corresponding to a region of the heart. The method can further include obtaining image data corresponding to the one or more pixel locations during the series of images, and measuring, e.g., by an image processor, a periodicity of the image data for each of the one or more pixel locations over the series of images. The periodicity corresponds to an electromechanical signal of the heart in the region corresponding to the measured one or more pixel locations.

In some embodiments, measuring the periodicity of the image data can include measuring a peak frequency of the image data for each of the one or more pixel locations. The method can further include determining a peak cycle length from each peak frequency, and the peak cycle length can correspond to an electrical cycle length of the electromechanical signal of the heart in the region corresponding to the measured one or more pixel locations. The method can further include measuring a phase associated with each peak frequency, and the phase can correspond to a direction of propagation of the electromechanical signal in the heart.

In some embodiments, measuring the periodicity can include measuring a crossing of a threshold of the image data for each of the one or more pixel locations. The threshold can correspond to a condition of zero strain at the region of the heart corresponding to the one or more pixel locations. Additionally or alternatively, measuring the periodicity can include performing a Fourier transform of the image data for each of the one or more pixel locations.

In some embodiments, the image data can include first image data corresponding to one or more first pixel locations corresponding to a first region of the heart and second image data corresponding to one or more second pixel locations corresponding to a second region of the heart. As embodied herein, the method can further include comparing a first periodicity corresponding to the first region and a second periodicity corresponding to the second region. Additionally or alternatively, the method can further include measuring a first phase associated with the first periodicity and a second phase associated with the second periodicity, and comparing the first phase with the second phase to determine a direction of propagation of the electromechanical signal in the heart. The first region of the heart can include at least a portion of the right atrium, and the second region of the heart can include at least a portion of the left atrium or ventricles.

In some embodiments, the method can include determining a type of arrhythmia in the heart corresponding to the electromechanical signal. The method can further include estimating a likelihood of success of a treatment for the arrhythmia.

In another embodiment of the disclosed subject matter, an imaging system for mapping behavior of a heart includes an imaging device and an image processor coupled to the imaging device. The imaging device can be configured to acquire a series of two or more images of the heart at one or more pixel locations, each pixel location corresponding to a region of the heart. The image processor can be configured to obtain image data of the one or more pixel locations during the series of images, and measure a periodicity of the image data for each of the one or more pixel locations over the series of images. The periodicity corresponds to an electromechanical signal of the heart in the region corresponding to the measured one or more pixel locations.

In some embodiments, the image processor can be configured to measure the periodicity of the image data by measuring a peak frequency of the image data for each of the one or more pixel locations, and the image processor can be further configured to determine a peak cycle length from each peak frequency. The peak cycle length can correspond to an electrical cycle length of the electromechanical signal of the heart in the region corresponding to the measured one or more pixel locations. The image processor can be further configured to measure a phase associated with each peak frequency. The phase can correspond to a direction of propagation of the electromechanical signal in the heart.

In some embodiments, the image processor can be further configured to measure the periodicity by measuring a crossing of a threshold of the image data for each of the one or more pixel locations. The threshold can correspond to a condition of zero strain at the region of the heart corresponding to the one or more pixel locations. Additionally or alternatively, the image processor can be further configured to measure the periodicity by performing a Fourier transform of the image data for each of the one or more pixel locations.

In some embodiments, the image data can include an intensity of each of the one or more pixel locations. The imaging device can include an ultrasound transducer.

In some embodiments, the image data can include first image data corresponding to one or more first pixel locations corresponding to a first region of the heart and second image data corresponding to one or more second pixel locations corresponding to a second region of the heart. As embodied herein, the image processor can be further configured to compare a first periodicity corresponding to the first region and a second periodicity corresponding to the second region. The image processor can be further configured to compare a first phase associated with the first periodicity and a second phase associated with the second periodicity, and compare the first phase with the second phase to determine a direction of propagation of the electromechanical signal in the heart. The first region of the heart can include at least a portion of the right atrium, and the second region of the heart can include at least a portion of the left atrium.

In some embodiments, the image processor can be further configured to determine a type of arrhythmia in the heart corresponding to the electromechanical signal. The image processor can be further configured to estimate a likelihood of success of a treatment for the arrhythmia.

BRIEF DESCRIPTION OF THE DRAWINGS

The accompanying drawings, which are incorporated and constitute part of this disclosure, illustrate some embodiments of the disclosed subject matter.

FIGS. 1A-1C each illustrates an exemplary technique for mapping cardiac rhythm in a subject using electromechanical-wave imaging (EWI) according to the disclosed subject matter.

FIGS. 3A-3C each illustrates further details of the exemplary techniques of FIGS. 1A-1C.

FIGS. 7A-7E illustrates exemplary techniques for mapping cardiac rhythm in a subject undergoing a cardioversion procedure according to another aspect of the disclosed subject matter.

FIGS. 9A-9D illustrates further details of the exemplary techniques of FIGS. 7A-7E.

FIGS. 11-1 to 11-3(b) together illustrate exemplary techniques for data acquisition and motion and strain estimation according to other aspects of the disclosed subject matter.

FIGS. 12-1(a) to 12-3(b) together illustrate exemplary techniques for electromechanical cycle length mapping according to other aspects of the disclosed subject matter.

FIGS. 21(a)-21(g) are exemplary images illustrating further details of the techniques of FIG. 19.

FIGS. 22(a)-22(f) are exemplary images illustrating further details of the techniques of FIG. 19.

FIGS. 23(a)-23(e) are exemplary images illustrating further details of the techniques of FIG. 19.

FIGS. 24(a)-24(e) are exemplary images illustrating further details of the techniques of FIG. 19.

Throughout the figures and specification the same reference numerals are used to indicate similar features and/or structures.

DETAILED DESCRIPTION

Figure 2A:
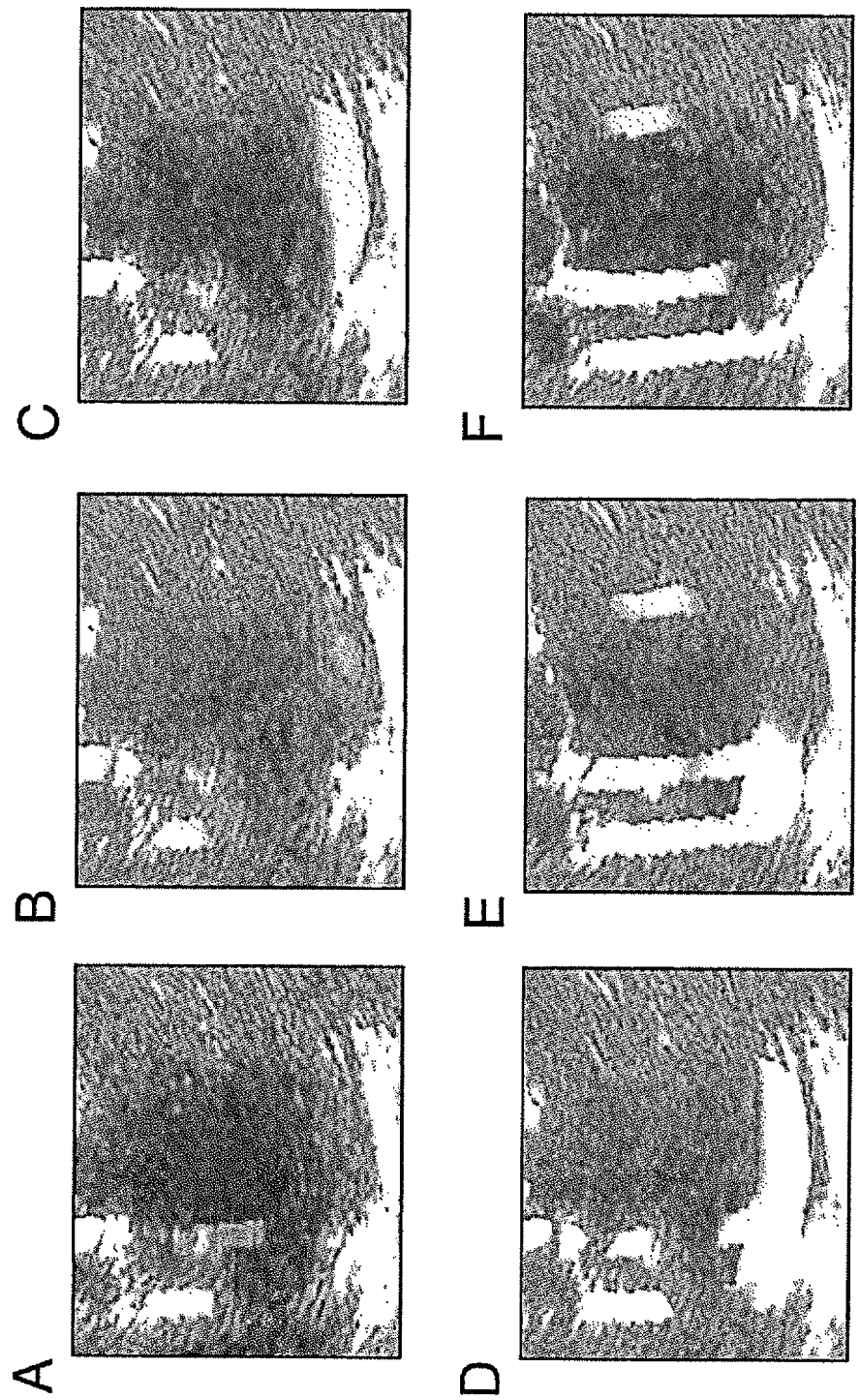
FIGS. 2A-2C each illustrates further details of the exemplary techniques of FIGS. 1A-1C.

The systems and methods described herein are useful for mapping behavior of an electromechanical system. Although the description provides as an example mapping behavior of the heart, the systems and methods herein are useful for mapping behavior of any suitable electromechanical system, including neural systems, skeletal systems, among others.

The subject matter disclosed herein includes methods and systems for mapping behavior of a heart. Accordingly, the techniques described herein can utilize of a series of two or more images of the heart. The series of images can be taken at one or more pixel locations, each pixel location corresponding to a region of the heart. The method can further include obtaining image data corresponding to the one or more pixel locations during the series of images, and measuring, by an image processor, a periodicity of the image data for each of the one or more pixel locations over the series of images. The periodicity corresponds to an electromechanical signal of the heart in the region corresponding to the measured one or more pixel locations.

Transient deformations imaged at suitable temporal and spatial resolution can be used to recover the electrical activation sequence in normal and paced human subjects non-invasively and can be used in planning and monitoring ablation-based arrhythmia treatments. In this manner, systems and techniques described herein can be used to quantitatively characterize focal and reentrant arrhythmias.

According to the disclosed subject matter, spatio-temporal maps of a full-view of the atrial and ventricular mechanics of a heart can be obtained in a single heartbeat, which can show the electromechanical patterns of atrial flutter, fibrillation, and tachycardia in the heart. During focal arrhythmias such as preventricular contraction and focal atrial tachycardia, electromechanical wave imaging (EWI) methodology can be used to identify the location of the focal zone and the subsequent propagation of cardiac activation. During reentrant arrhythmias such as atrial flutter and fibrillation, Fourier analysis of the strains can reveal highly correlated mechanical and electrical cycle lengths and propagation patterns. In this manner, EWI can be integrated in an ultrasound system to characterize the mechanical and electromechanical function representative of atrial and ventricular arrhythmias. As such, systems and techniques according to the disclosed subject matter can assist in the diagnosis and/or treatment of arrhythmias, including without limitation, foci localization in treatment planning, real-time guidance and monitoring of ablation and post-treatment assessment of the success of the treatment.

In an exemplary technique, strain maps can be generated using the methods developed for single-heartbeat electromechanical wave imaging (EWI), as shown and described for example in U.S. Patent Application Publication Nos. 2008/0285819 and 2007/0049824, each of which is incorporated by reference herein in its entirety. As embodied herein, an ultrasound system can be calibrated and configured to adhere to FDA standards both in terms of mechanical index and of spatial-peak-temporal-average intensity, and as such can be suitable for human use. A circular ultrasound wave can be emitted to estimate motion, and as embodied herein, the ultrasound wave can have a virtual focus 10.2 mm behind the probe at 2000 fps for 2 s. A standard B-mode acquisition can performed, as embodied herein for 1.5 s, to acquire B-mode frames depicting the heart anatomy. Frames from the motion-estimation sequence can be reconstructed, for example and as embodied herein by creating 128 lines in post-processing in the direction orthogonal to the ultrasound wavefront via sum-and-delay with a reconstructed sampling frequency of 20 MHz. As embodied herein, the motion-estimation rate and the motion-sampling rate can be 1000 and 2000 fps, respectively. Furthermore, and as embodied herein, the window used for motion-estimation can be 9.2 mm wide with an overlap of 95.8% (e.g., window shift of 0.3 mm), and the kernel used for strain estimation can be 4.9 mm wide. Beamforming, motion-estimation, strain estimation, spatial moving-average of the strains (e.g., 12 mm by 10 lines), and automated contour tracking techniques can be performed off-line, for example and as embodied herein using a Tesla GPU (Nvidia, Santa Clara, Calif.) and Matlab parallel processing toolbox (The Mathworks, Nattick, Mass.), which can have a computing speed of 2.4 frames/s.

Different types of rhythms, such as focal and reentrant rhythms, can be analyzed differently. For example, FIGS. 1A-1C depict strains mapped in subjects undergoing sinus rhythm (FIG. 1A), atrial flutter (FIG. 1B) and atrial fibrillation (FIG. 1C). As shown in FIG. 1A, in subjects undergoing sinus rhythm, the strains over time at one location in, e.g., one pixel in the left atrium, can present two events corresponding approximately to the beginning and the end of systole. The onset of these events, which can be represented as the first zero-crossing of the strain map, can be tracked for every pixel of the heart walls, and in this manner, the propagation of the electromechanical wave can be mapped.

With reference now to FIG. 1B, in atrial flutter patients, a similar location in the left atrium can reveal periodic strains, which can be, as embodied herein, represented by a single frequency. For purpose of comparison, as shown in FIG. 1C, in a patient with atrial fibrillation, multiple frequencies can be observed, and as such, an analysis based on a Fourier transform can be utilized.

Accordingly, as shown in FIG. 1A, in patients undergoing focal rhythms such as sinus rhythm and focal tachycardia, the onset of contraction can be determined as the first zero-crossing of the incremental strains occurring after the onset of the P-wave on the electrocardiogram (ECG), following the EWI techniques described herein. For purpose of comparison, as illustrated in FIGS. 1B-1C, in patients undergoing reentry, i.e., during atrial flutter and atrial fibrillation, a Goertzel algorithm can be performed, for example and as embodied herein on 1.5-s long incremental strains signals, to obtain a high resolution temporal Fourier transform for each individual pixel of the atria. For convenience, frequencies can be converted to cycle lengths, referred to herein as the mechanical cycle length (MCL). Peak MCL maps can be generated by selecting the MCL with the greatest amplitude within the 100-330 ms range for each pixel. Peak cycle length histograms can be constructed, and for purpose of comparison and verification of the disclosed techniques, can be compared to the electrical cycle length measured directly during the mapping and ablation procedure.

Figure 2B:
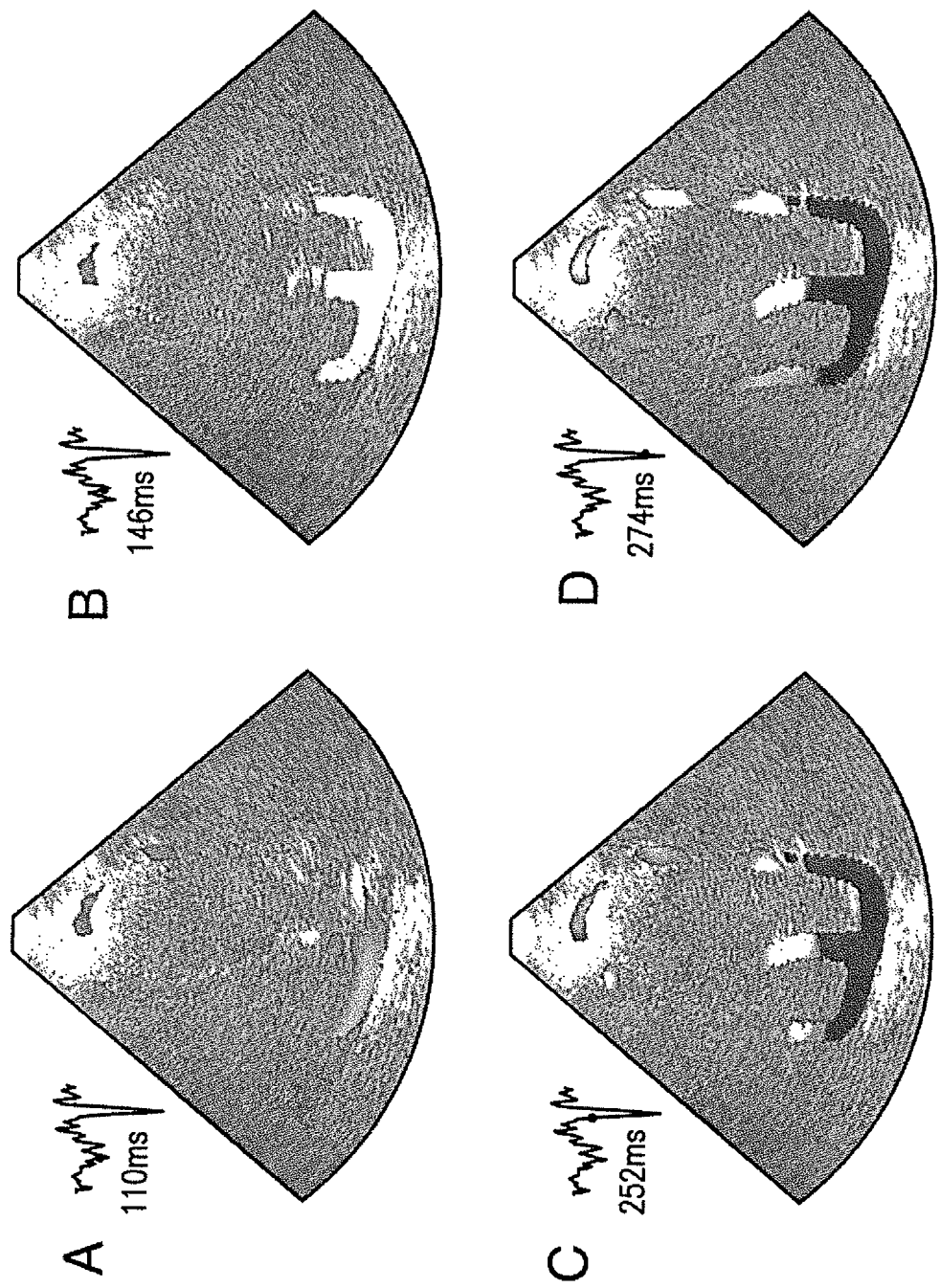
Figure 2C:
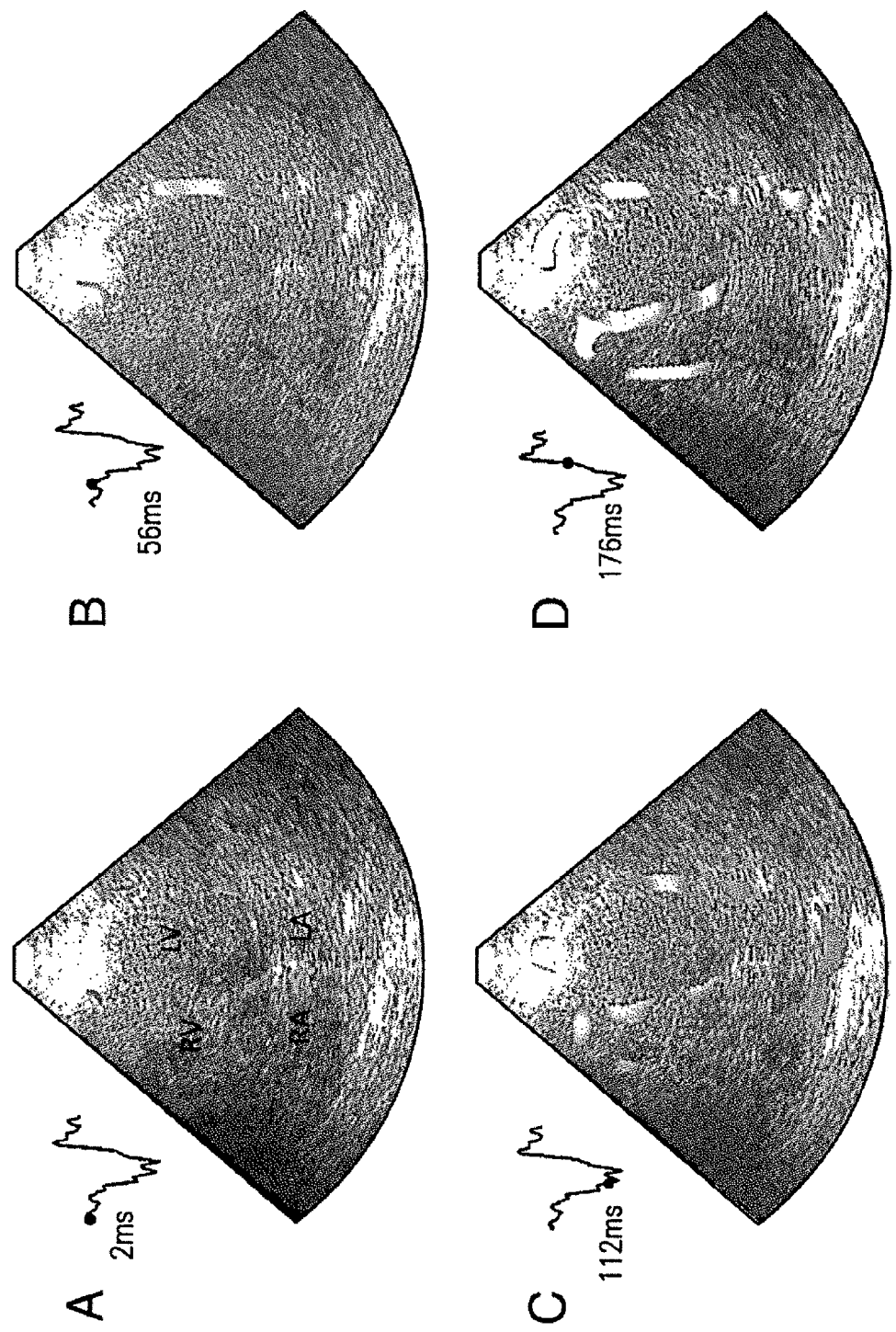

With reference now to FIGS. 2A-2C, EWI cine-loops and isochrones during focal rhythms are depicted. FIG. 2A shows an exemplary atria of a patient and illustrates that electrical mapping can reveal a focal atrial tachycardia, with a focus located high in the left atrium (LA). However, complete electrical mapping of the patient in this example was not completed in the LA due to potential complications associated with trans-septal punctures. EWI shows that electromechanical activation can originate from the LA. The electromechanical wave can propagate from the LA into the atria, after which further activation can be detected in the ventricles.

FIGS. 2B and 2C each show exemplary isochrones obtained in a different patient with an underlying ventricular tachycardia. EWI can be performed during sinus rhythm and during pre-ventricular contraction. As illustrated in FIG. 2B, the EWI isochrones obtained during sinus rhythm can depict propagation from the right atrium (RA), into the LA and into the ventricles. However, in the exemplary isochrone depicted in FIG. 2B, the ventricular activation sequence can be considered abnormal, with the lateral wall of the left ventricle (LV) undergoing activation prior to the bundle branches terminal in the septum and right ventricle (RV) apex. As such, during preventricular contraction, the region activated early in the ventricle during sinus rhythm can trigger the entire electromechanical activation sequence, i.e., from the ventricles to the atria.

Figure 3A:
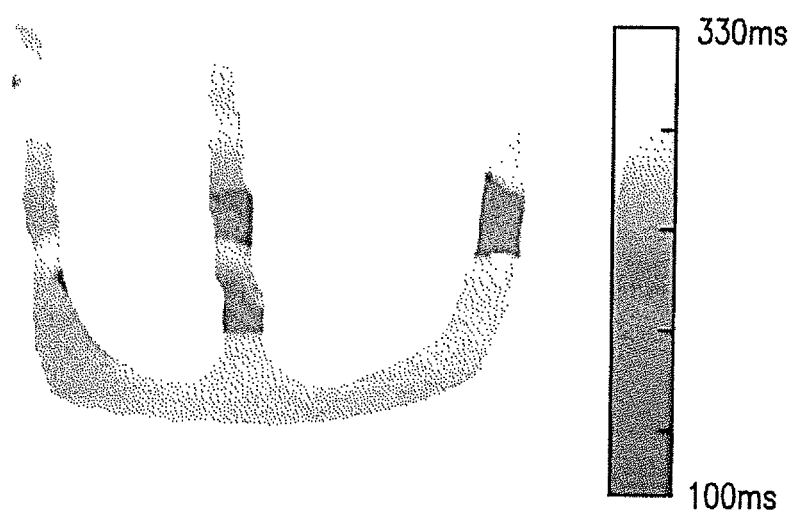

With reference now to FIGS. 3A-3C, mechanical behavior of a heart with atrial flutter is illustrated. FIG. 3A shows a peak MCL map corresponding to a heart having atrial flutter. In this exemplary heart, a single MCL can be represented as having a single dominant frequency, as further illustrated by the histogram of FIG. 3B, which shows a corresponding representative MCL of approximately 294 ms. The phase of the MCL can be analyzed in Fourier space, and a propagation pattern originating from the RA near the tricuspid valve towards the LA can be identified, as shown for example in FIG. 3C. As embodied herein, the electrical cycle length of the heart is 286 ms.

Figure 4A:
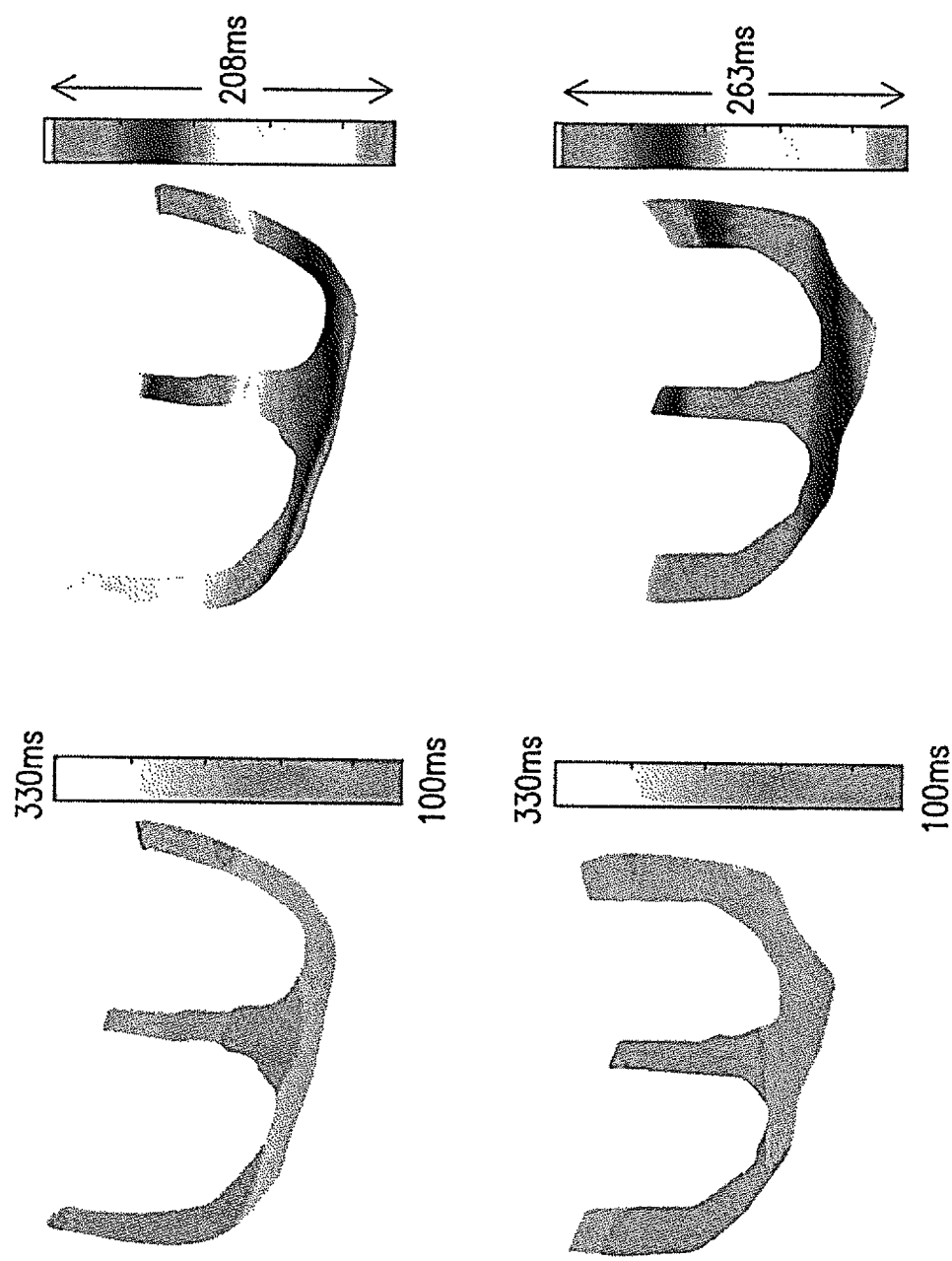
FIGS. 4A-4D each illustrates further details of the exemplary techniques for mapping cardiac rhythm in a subject.
Figure 4B:
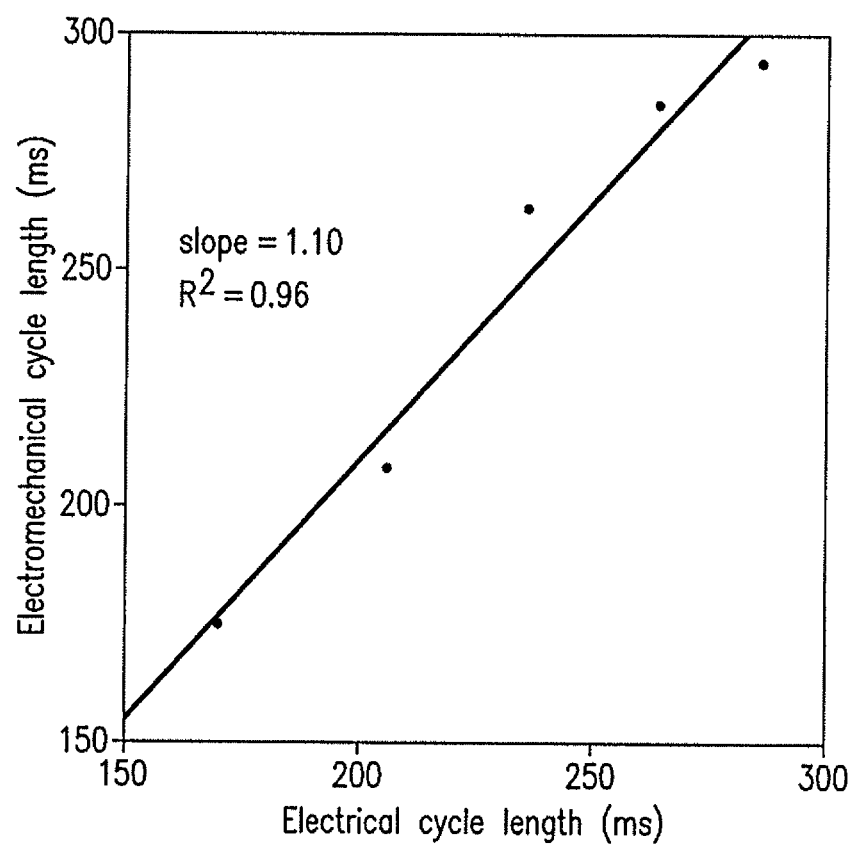

With reference now to FIGS. 4A-4D, for purpose of comparison, certain hearts having atrial flutter can be represented as having two or more dominant frequencies, which can be separated between the left and right atria. FIG. 4A shows two examples of atrial flutter exhibiting multiple frequencies. As shown in FIG. 4A, peak MCL maps can each exhibit two dominant frequencies, one mostly located in the RA, and another being mostly located in the LA. In each example, at least one of the two dominant MCLs can be considered to be close to the electrical cycle length, as shown for example in FIG. 4B.

Figure 4C:
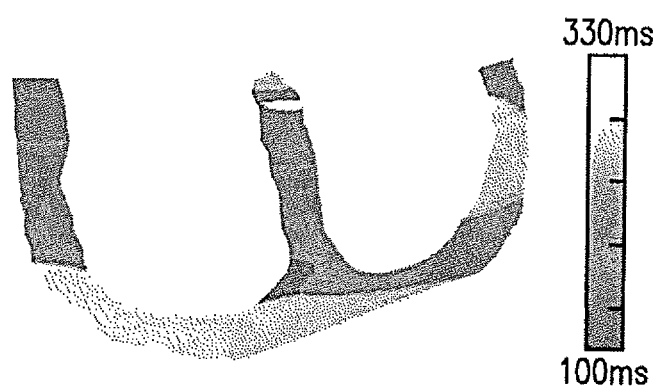
Figure 4D:
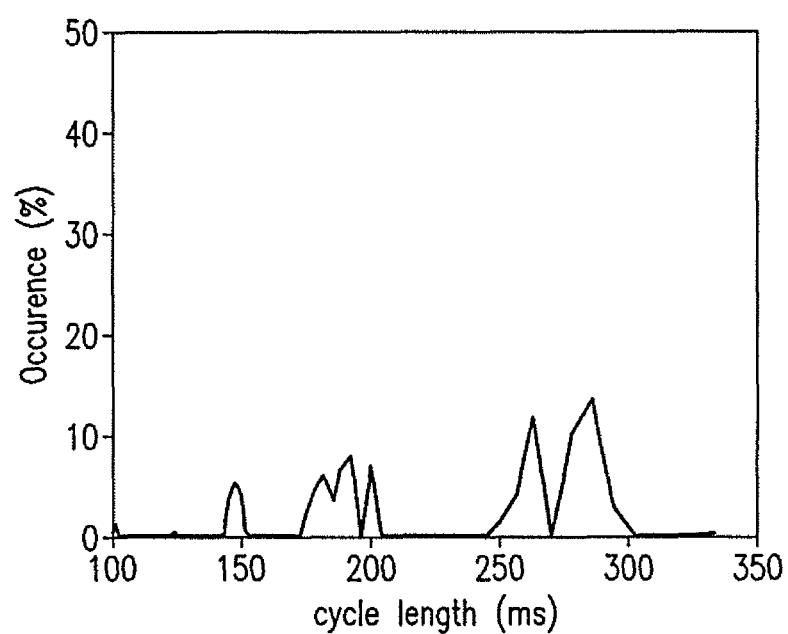

FIGS. 4C and 4D illustrate mechanical behavior of a heart undergoing atrial fibrillation. The peak MCL map in FIG. 4C shows multiple dominant frequencies, which can be quantified by a corresponding histogram, as shown for example in FIG. 4D. As shown in FIG. 4D, the resulting frequencies can be fragmented spatially, but can remain generally grouped together.

Accordingly to the disclosed subject matter, the mechanics of certain types of atrial and ventricular arrhythmias can be observed and characterized with high accuracy and spatial and temporal resolutions in a full field of view, and can include characterization of focal and reentrant rhythms. Electromechanical propagation pattern or dominant mechanical cycle lengths can be characterized, and can be associated with respective electrical equivalents.

Focal rhythms can behave similarly to paced rhythms, and as such, a single source of electromechanical activation can be located in the vicinity of the electrical focal zone. EWI can be utilized to characterize the propagation of the electromechanical activation from the sinus node in the atria and from the bundle branch terminals in the ventricles as well as during ventricular pacing.

According to the techniques described herein, electromechanical activation propagation patterns can be observed in the atria of a heart with underlying ventricular tachycardia during sinus rhythm, including with an early ventricular activation in the lateral wall of the left ventricle. The left ventricle can be considered to be at the electromechanical focus of preventricular contractions, and as such, the left ventricle exhibiting ventricular tachycardia during sinus rhythm can be considered to contain abnormal tissue or be part of an accessory pathway. In a heart with atrial tachycardia, the electromechanical activation propagation pattern can reveal a source located high in the LA, in accordance with electrical mapping. As such, the techniques described herein can be utilized for non-invasive, ultrasound-based, electromechanical activation mapping prior to invasive procedures. Indeed, knowledge of an electromechanical source located in the LA, for example prior to a trans-septal puncture procedure, can be used as a factor in the risk-benefit analysis performed to determine the best course of treatment, e.g., pharmacological compared to ablation treatment.

During atrial flutter, the electromechanical activation maps described herein can be considered to be closely correlated with their electrical counterpart, at least in part of the atrial tissue. Indeed, with reference to FIGS. 3A-3C, a single dominant frequency can be identified, and the phase of that frequency can reveal a propagation direction from the tricuspid valve to the LA. In other examples, with reference to FIGS. 4A-4D, two or more distinct behaviors in the atria can be identified: that is, one part of the atria can be contracting with the same frequency as the electrical activation, while another region does not necessarily do so. As such, mapping the mechanics of the heart can identify regions in which the mechanical and electrical activities appeared to be decoupled. Further spatial fragmentation of the periodicity of the mechanics of the atria can be observed during fibrillation.

In some embodiments, stretching of the atria, which can be caused at least in part by ventricular contraction, can affect frequency analysis involving multiple activation cycles. Indeed, the strains in the atria can be modified by the ventricular activity, and as such, the analysis can be timed by taking into account the surface ECG and the ventricular mechanical activity mapped simultaneously.

In practice, echocardiograms can typically be performed on arrhythmic patients, while other non-invasive electrical mapping techniques can typically utilize high-resolution CT or MRI scans. With suitable sequences and equipment, the electromechanical activation mapping according to the disclosed subject matter can be obtained from such echocardiograms without the need to utilize high-resolution CT or MRI scans.

Mapping non-invasively and in real-time the electromechanical activity during arrhythmias according to the disclosed subject matter can be used to better understand the function of atrial mechanics in the evolution and perpetuation of arrhythmias and can be used both for risk assessment of ablation procedures and/or for a better longitudinal monitoring of the outcomes of ablation procedures.

According to another aspect of the disclosed subject matter, intracardiac echocardiography (ICE) can be used to provide real-time imaging of the heart to identify anatomic structures and guide ablation. In this manner, ICE can provide suitable imaging for lesion characterization. In addition to being utilized for guiding electrophysiology procedures, ICE can also be used to acquire data for monitoring ablation lesions without requiring additional or modification of the ablation procedure.

Furthermore, ICE can be utilized along with myocardial elastography (ME) to assess strains at a high temporal resolution and a large field of view of the heart. In this manner, techniques for assessing myocardial strain can be provided to achieve high temporal resolution and large fields of view with ICE in vivo and to characterize myocardial strains with ICE before and after ablation.

In one embodiment, an exemplary technique for assessing myocardial strain in a subject can include anesthetizing the subject with an intravenous injection of propofol 2-5 mg·kg-1. The technique can further include mechanically ventilating the subject with a rate- and volume-regulated ventilator on a mixture of oxygen and titrated 0.5-5.0% isoflurane. An ICE catheter can be inserted in the right atrium of the subject through the jugular vein. For purpose of illustration and not limitation, the subject can be a canine. However, as further described herein, the subject can include any suitable animal or human subject. For example, for purpose of illustration and not limitation, a human subject with AF can be scanned with ICE during an ablation procedure. An ICE catheter can be inserted into the femoral vein and pushed into the right atrium of the human subject. In addition to RF signals and B-mode images acquired transthoracically, as discussed herein, additionally or alternatively, RF signals and B-mode images of the human subject can be acquired with ICE.

For purpose of illustration and not limitation, and as embodied herein, a 5.8-MHz ICE catheter (ViewFlex PLUS ICE catheter, St. Jude Medical, St. Paul, Minn., USA) on an ultrasound system (Z.one ultra, Zonare, Mountain View, Calif., USA) can be utilized to acquire ultrasound RF signals and/or B-mode images described herein. As embodied herein, the imaging depth can be set 90 mm, or any other suitable imaging depth to allow for imaging of at least one heart chamber. The ultrasound system can be connected to a computer via a data cable, which can allow for commands to be sent to the imaging system, for example to set parameters, start and stop the acquisition and transfer the data to a hard drive connected to the system. An unfocused diverging beam transmit can be used, which can achieve a high frame rate (e.g., 1200 fps or more) compared to conventional B-mode.

In the exemplary embodiments described herein, for purpose of illustration, echocardiographic views of the RV and LA were acquired for the canine subject, and views of the LA only were acquired for the human subject.

For each subject, in-phase/quadrature (IQ) data can be acquired on all the 64 channels in parallel and stored in the system buffer. For example and without limitation, at a 90-mm depth and 1200 fps, the buffer of the ultrasound system can store up to 620 ms of IQ signals. Conventional B-mode images can be acquired at 35 fps at the same location, for example for structure identification and to aid in segmentation. The data can be transferred to a computer processor for off-line processing.

The RF signals can be obtained from the IQ data and can be upsampled to 50 MHz, which can increase the quality of the motion estimation. The RF signals can be reconstructed, for example and without limitation, and as embodied herein, on a 90-mm depth and 90° angle field of view using a delay-and-sum algorithm. A B-mode image can be obtained from the reconstructed RF data, for example by using a Hilbert transform. A manual or automated segmentation can be performed to retrieve the myocardium. The B-mode images can be used as a visual reference to assist in the myocardium segmentation. The displacement between two frames can be estimated, for example, by normalized 1-D cross-correlation, which can have a window length of 10 wavelength (i.e., 2.7 mm) and 95% overlap. The estimated displacements can be integrated during systole or diastole, for example corresponding to the part of the cardiac cycle captured within the acquisition period.

In some embodiments, for example where electrocardiogram (ECG) can be available to be acquired synchronously and saved with the ultrasound channel data, the relative myocardial wall displacement can be used as a surrogate to determine the systolic and the diastolic phase. During contraction, the volume of the heart chamber can decrease. As such, the onset of systole can be determined as the time in which both walls of the heart chamber of the considered view can be seen to move toward each other. During relaxation, the volume of the heart chamber can increase. As such, the onset of diastole can be determined as the time in which both walls of the heart chamber of the considered view can be seen to move away one from each other. Cumulative axial strains can be computed, for example and without limitation, and as embodied herein, by taking the spatial derivative of cumulative axial displacements using a least-squares estimator with a kernel equal to 5.1 mm, which can decrease the noise.

According to the exemplary techniques described herein, displacement and strain was estimated in the myocardium of the canine with ICE at 1200 fps from RF data during sinus rhythm. The acquisition duration (i.e., 620 ms) was less than the cycle length (770 ms). As such, in this example, for each acquisition either the whole systolic or the whole diastolic phase was obtained, but not both.

Figure 5B:
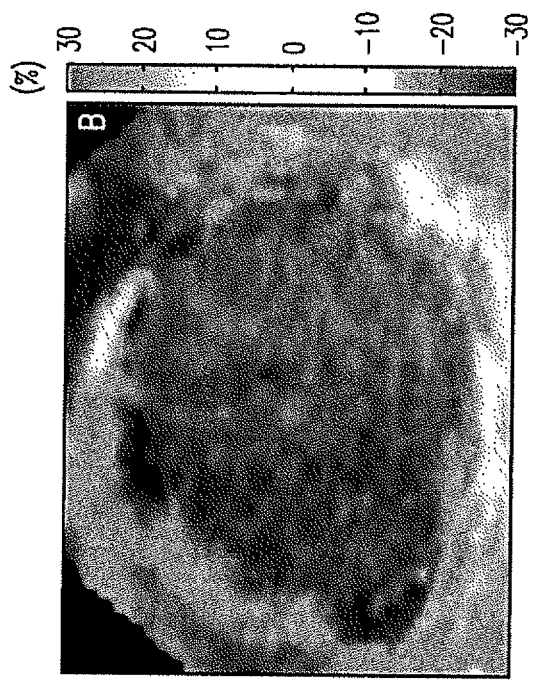
FIGS. 5A-5B each illustrates an exemplary technique for mapping cardiac rhythm using EWI and intracardiac echocardiography (ICE) according to another aspect of the disclosed subject matter.
Figure 5A:
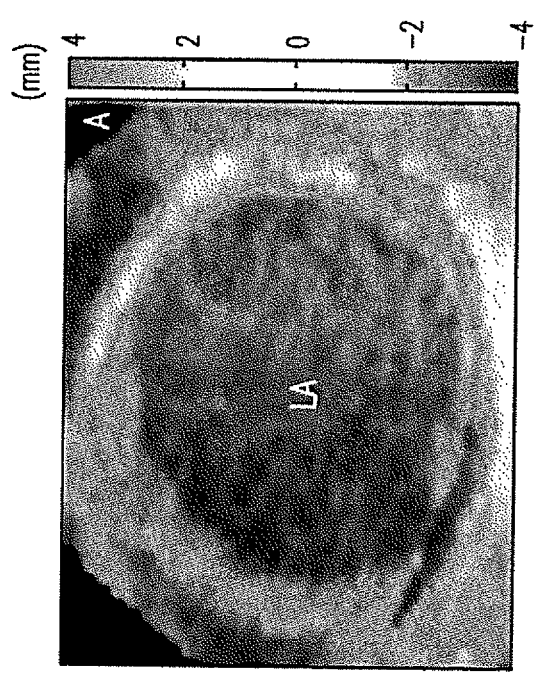

With reference to FIGS. 5A-5B, cumulative axial displacement (shown for example in FIG. 5A) and cumulative axial strain (shown for example in FIG. 5B) in canine LA during LA diastole are illustrated. The interatrial septum wall can be shown moving toward the transducer, and the left lateral wall can be shown moving away from the transducer. In this manner, relaxation can correspond to radial thinning and circumferential lengthening, and contraction can correspond to radial thickening and circumferential shortening. As shown, radial thinning can be observed in the interatrial septum and in the lateral wall whereas circumferential lengthening can occur in the anterior and posterior wall.

With reference to FIG. 5A, for purpose of illustration, displacement towards the transducer is shown in the positive side of the scale, and displacement away from the transducer is shown in the negative side of the scale. The interatrial septum wall can thus be shown as moving toward the transducer, and the left lateral wall can be shown as moving away from the transducer. With reference to FIG. 5B, in the corresponding strains, negative strain (i.e., relaxation) can be observed in the interatrial septum and in the lateral wall, and positive strain can be observed in the anterior and posterior wall.

Figure 6A:
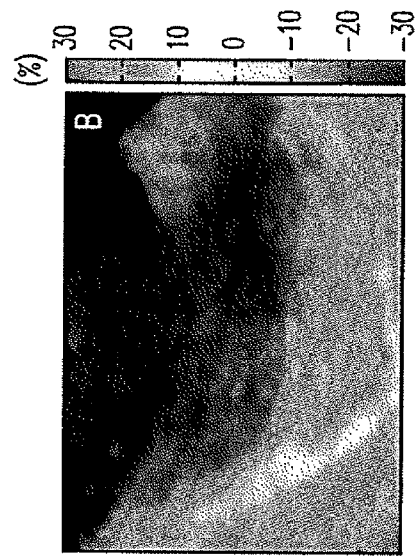
FIGS. 6A-6D each illustrates further details of the exemplary techniques of FIGS. 5A-5B.
Figure 6B:
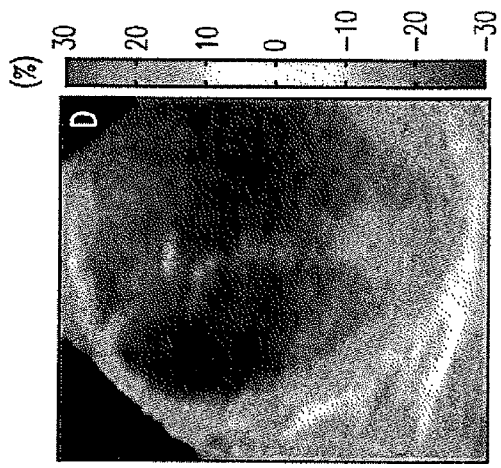
Figure 6C:
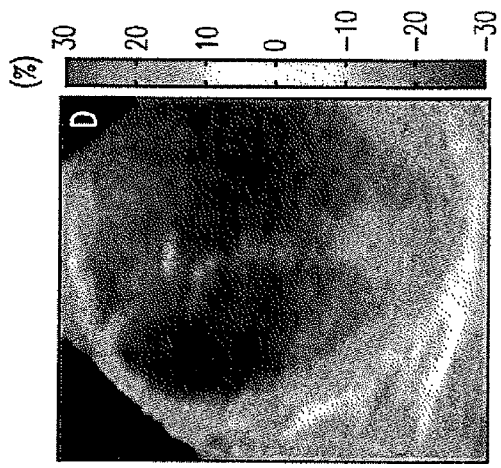
Figure 6D:
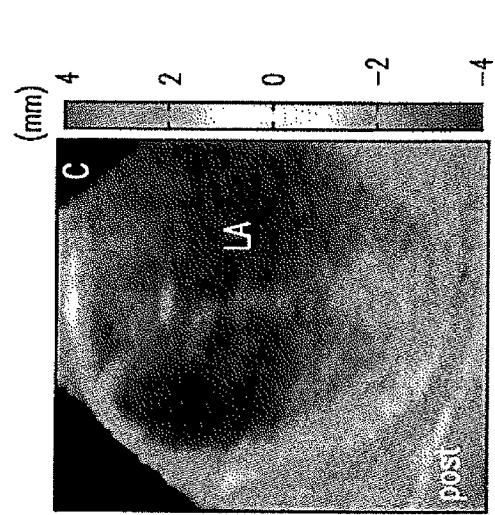
Figure 7C:
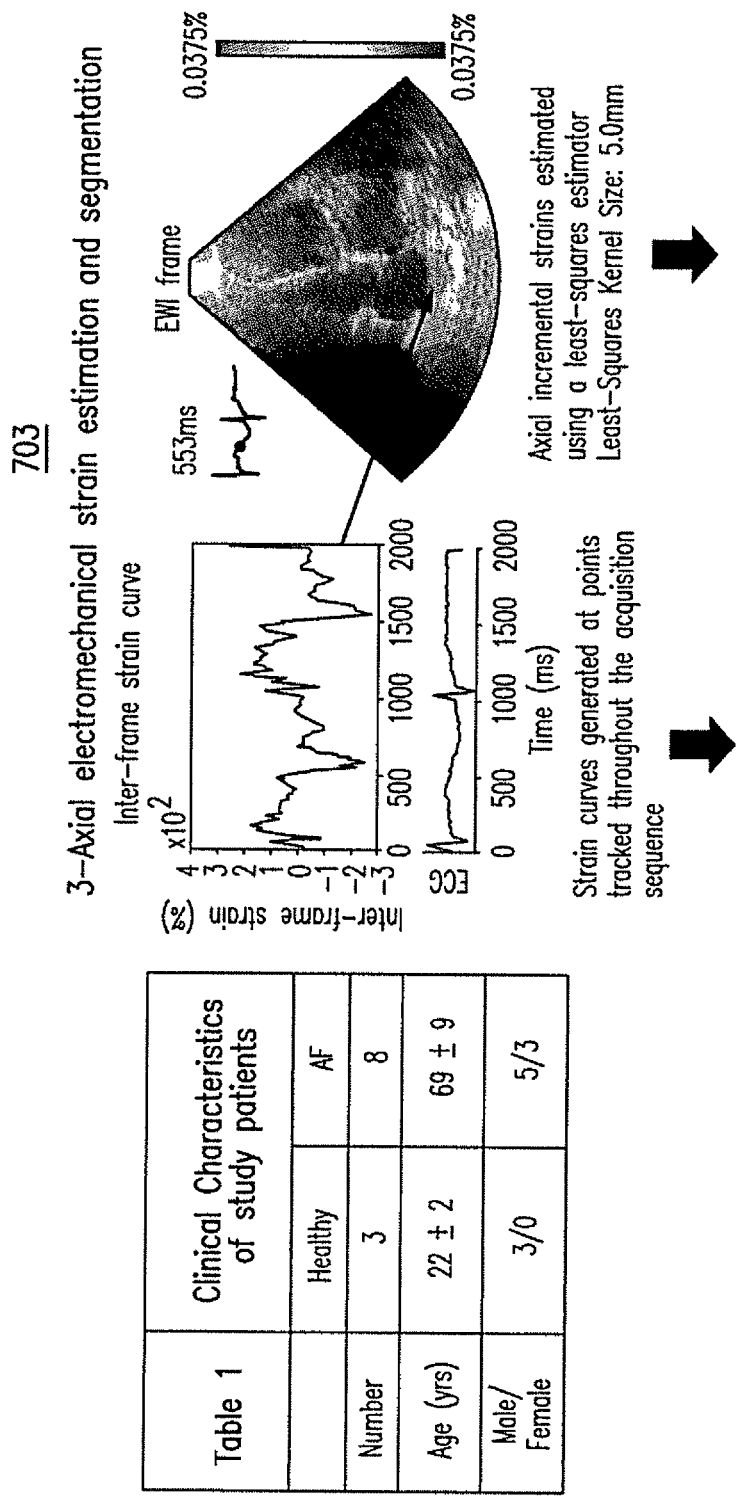
Figures 7D, 7E:
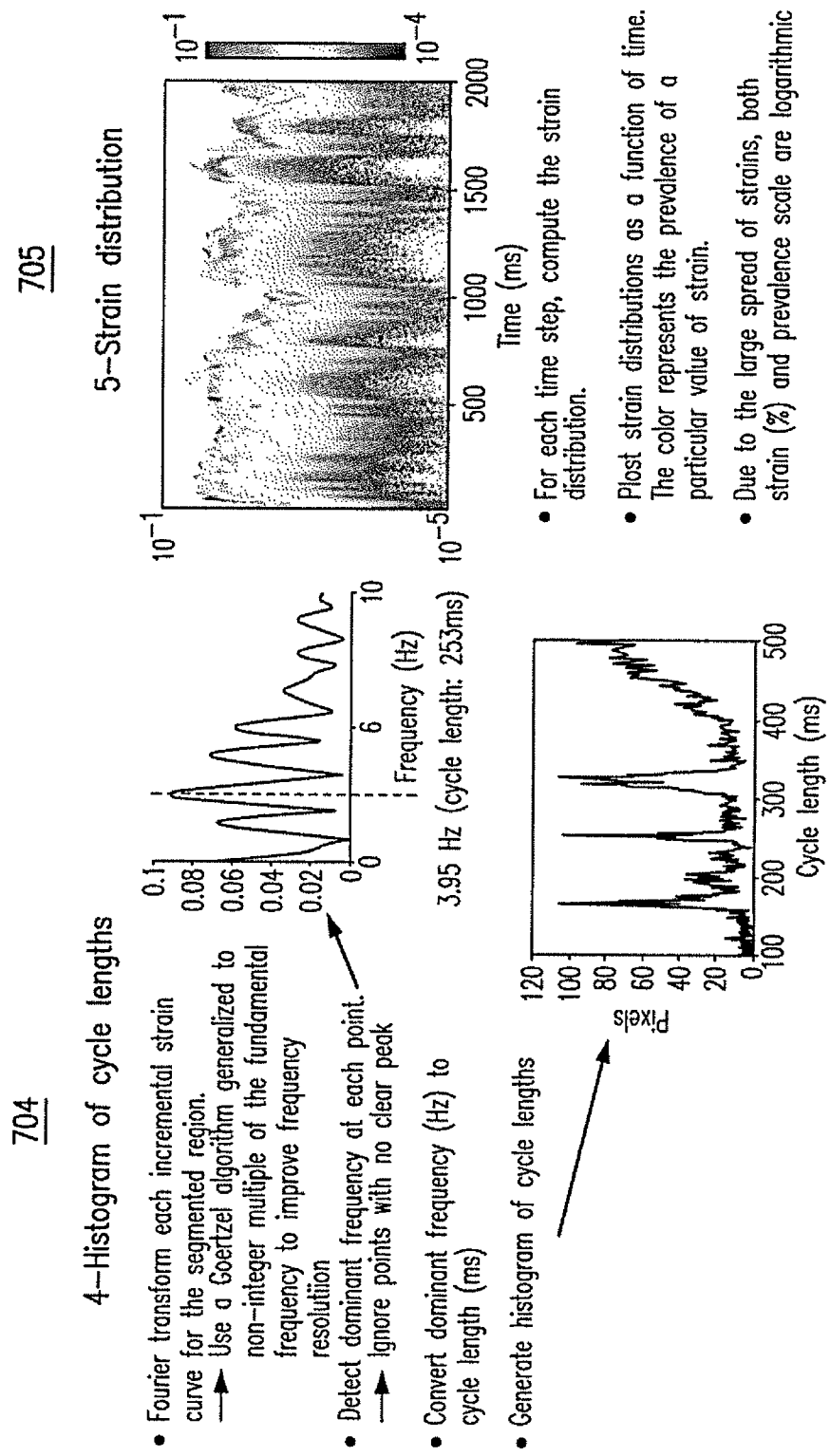

Referring now to FIGS. 6A-6D, displacements and strains can also be estimated in the LA of the human subject during the radio frequency (RF) ablation procedure according to the disclosed subject matter. Axial displacement before ablation is illustrated in FIG. 6A. As shown in FIG. 6A, the posterior wall can be observed moving toward the transducer, as indicated in the positive side of the scale. The corresponding strains are illustrated in FIG. 6B. As shown in FIG. 6B, radial thickening can be observed in the posterior wall, and the strain magnitude can be shown as approximately 30%. Axial displacements in the human LA during ablation and for the same cardiac phase are illustrated in FIG. 6C. The posterior wall can be observed moving towards the transducer. The corresponding strains are illustrated in FIG. 6D. As shown in FIG. 6D, radial thickening can be observed in the posterior wall, as indicated for example by positive strain. However, as shown, the strain magnitude can be lower (e.g., approximately 8%) in the region where ablation is occurring.

As discussed herein, myocardial strains can be measured with intracardiac echocardiography at a high temporal resolution in vivo and differences in strain can be measured with ICE before and after radio-frequency ablation. Such techniques can be used, for example and without limitation, for the assessment of one or more lesions induced by ablation during the ablation procedure to improve the efficiency of conduction block to treat the arrhythmia, for example as mechanical contraction of a region of the myocardium follows electrical activation of the same region. For purpose of illustration and not limitation, assessment of lesions induced by RF ablation is described herein. However, assessment of lesions induced by any ablation technique, for example and without limitation, cryoablation, microwave ablation, ultrasound ablation, laser ablation, can be performed using the techniques described herein.

For example, with reference to FIGS. 5A-5B, ME was performed in the canine LA. Displacements and strains were accumulated during LA diastole. The orientation of the ICE transducer relative to LA chamber allowed estimation in at least the radial and circumferential directions. Strains during LA diastole indicated radial thinning (negative) in the interatrial septum and the lateral wall, and circumferential lengthening (positive) in anterior and posterior region. This was consistent with the LA displacement, which showed that the interatrial septum wall moved toward the transducer (positive), and the left lateral wall moved away from the transducer (negative). As such, the displacement and strains can correspond to LA filling, during which LA volume increases can be concomitant to LA relaxation. In this manner, according to the techniques described herein, ME using ICE can assess ablation lesions in LA.

As a further example, the techniques according to the disclosed subject matter, as described herein, were also performed in a human subject during which an AF patient was scanned with a clinical ICE system at different sites before and during an ablation procedure. As shown in FIGS. 6A-6D, displacement and strain were obtained for LA systole. The lateral wall was observed moving toward the posterior wall, and radial thickening was observed. Strain in LA was found to be lower during ablation (8%) than before (30%) in the same region. The decrease in strain can be due, at least in part, to local stiffening of the tissue caused by the ablation.

As described herein, myocardial strain can be estimated from RF data acquired at high spatial and temporal resolution in vivo with ICE, for example during a clinical ablation procedure. Higher temporal resolution can allow for improved motion estimation, and thus, improved strain quality, at least in part because the higher temporal resolution can be less subjected to decorrelation. Higher spatial resolution can improve the characterization of the strain transmurally as well as along the myocardium. As such, the efficacy of lesions to block conduction as conduction recovery can be shown to be related to the non-transmurality and gap between lesions created during ablation. For example, RF ablation procedure of AF, which can be initiated with pulmonary vein isolation, can also include targeted sites for linear ablation, including for example LA roof, anterior and posterior wall or the cavotricuspid isthmus (CTI) in the RA. As such, characterization of thermal lesions in these regions can improve the assessment of conduction line block. According to the techniques described herein, strain from such lesions can be estimated in LA during ablation. For example, and as embodied herein, a decrease of strain was observed in a same region after ablation. In this manner, ME with ICE can guide the ablation by characterizing the lesions.

Furthermore, as embodied herein, the systolic phase relative to a chamber can be considered as the phase during which the walls of this chamber move towards each other, and the diastolic phase can be considered as the phase during which the walls were moving away from one another. As shown herein, such representations for systolic and diastolic phase detection can allow for results consistent with strain estimation.

As discussed herein, the identification of the systolic and the diastolic phase can be obtained from the myocardial walls relative displacements instead of from an ECG signal. Nevertheless, additionally or alternatively, the cardiac phase identification can be obtained using an ECG signal. Furthermore, synchronous acquisition and saving of the ECG signal with RF data can be performed.

For purpose of illustration, measurement of axial strains are described herein. However, any suitable strains, including for example and without limitation, lateral strains can be estimated using ME and can achieve angle-independency. Additionally or alternatively, the techniques described herein can be utilized to measure strains in one, two or three dimensions, or any suitable number of dimensions. Furthermore, for purpose of illustration, the techniques described herein were performed with reference to a canine and a human subject in vivo during an RF ablation procedure. However, the techniques described herein can be utilized to estimate displacement and strain using ICE for a subject undergoing an suitable arrhythmia of interest.

As described herein, myocardial strains in the plane of an echocardiographic view can be estimated with ICE at a high temporal resolution in vivo. Ablated regions can have different myocardial strains than before ablation. As such, myocardial elastography applied intracardially can be used to monitor thermal lesions during RF ablation.

According to yet another aspect of the disclosed subject matter, persistent atrial fibrillation (AF) can be treated with cardioversion, which can use antiarrhythmic drugs and/or a direct-current approach to return to normal sinus rhythm. In an exemplary technique according to the disclosed subject matter, electromechanical-wave imaging (EWI), which can be considered a direct ultrasound-based imaging technique, can be utilized to map the transmural electromechanical activation in all four chambers in vivo. In the exemplary technique, EWI processing based on analysis of the frequency content of the incremental strain curves can be utilized. In this manner, EWI can differentiate between healthy and AF subjects and can be utilized to predict successful direct-current cardioversion procedures.

With reference to FIGS. 7A-7E, in one example, four patients (i.e., n=4) with AF and admitted for cardioversion and four healthy subjects (i.e., n=4) were examined. As embodied herein, at 701, a Verasonics system (Verasonics, Redmond, Wash.) with a 2.5-MHz phased array can be used to perform EWI transthoracically in free-breathing and conscious subjects using an unfocused beam sequence at 2000 frames/s in the standard apical views. At 702, axial incremental displacement and segmentation can be estimated using RF-cross-correlation, embodied herein using a window size of 6.2 mm (i.e., 10 wavelengths) and a window shift of 0.612 mm (i.e., 90% overlap).

As shown for example at 703, axial electromechanical strains can be estimated and segmented. Strain curves can be generated at points throughout the acquisition sequence and tracked therein. The axial incremental strains can be estimated using a least-squares kernel, embodied herein having a size of 5.0 mm. The atrial myocardium can be segmented and frequency analysis of the corresponding incremental axial strain curves can be performed using a modified Goertzel algorithm, and as shown for example at 704 and as embodied herein, the Goertzel algorithm can be generalized to a non-integer multiple of the fundamental frequency of the strain, which can improve frequency resolution. Dominant frequencies can be extracted from the frequency spectra and converted to cycle lengths, and histograms of the distribution of cycle lengths across the atria can generated. In this manner, at 705, for each time step, the strain distribution can be computed. The strain distributions can be plotted as a function of time, and the prevalence of a particular value of a strain can be represented in the plot. As shown at 705, due at least in part to the large spread of the strain distributions, for clarity, both the strain percentage (%) scale and the prevalence scale can be represented logarithmically.

Figure 8A:
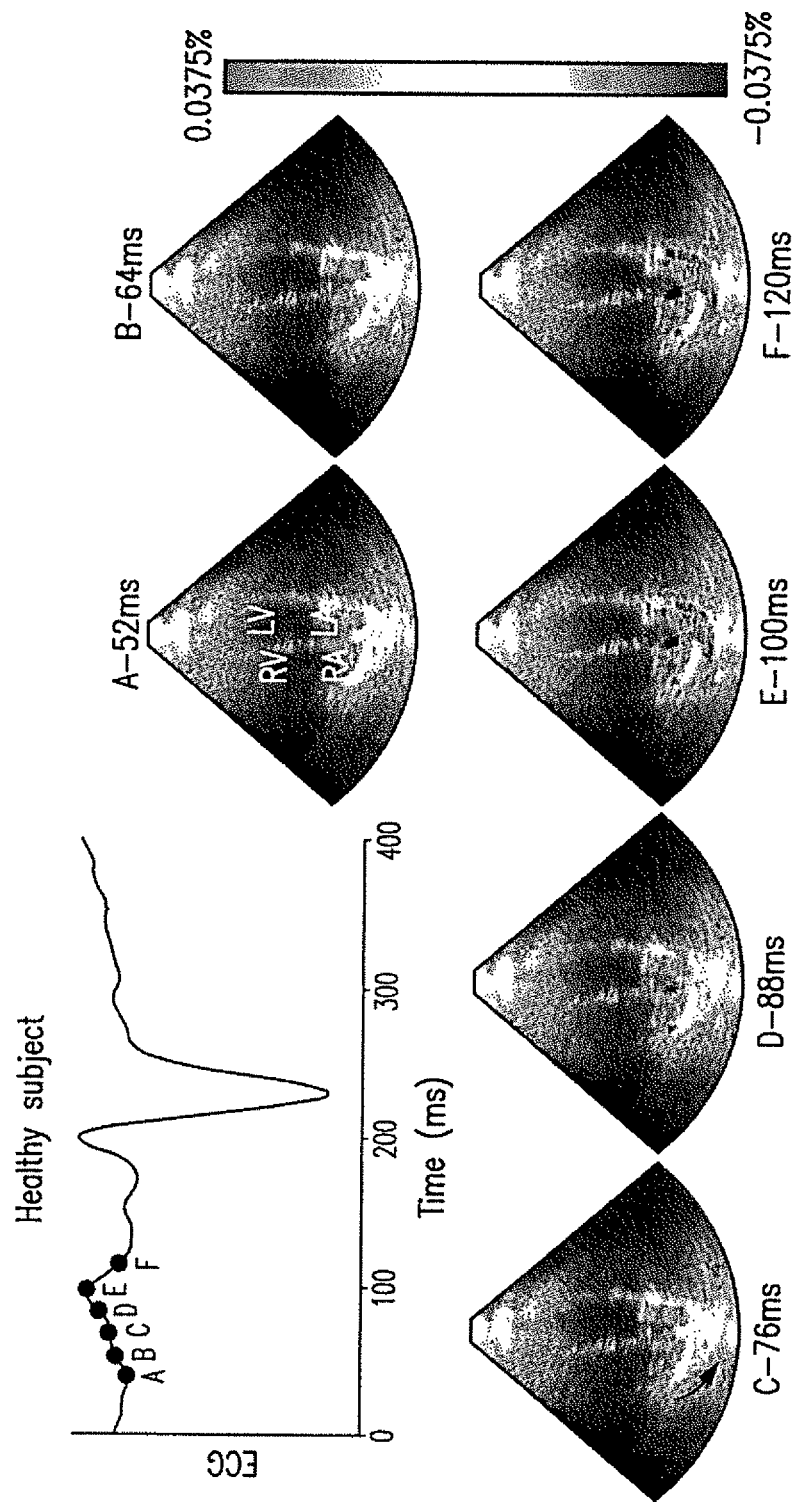
FIGS. 8A-8C illustrates further details of the exemplary techniques of FIGS. 7A-7E.
Figure 8B:
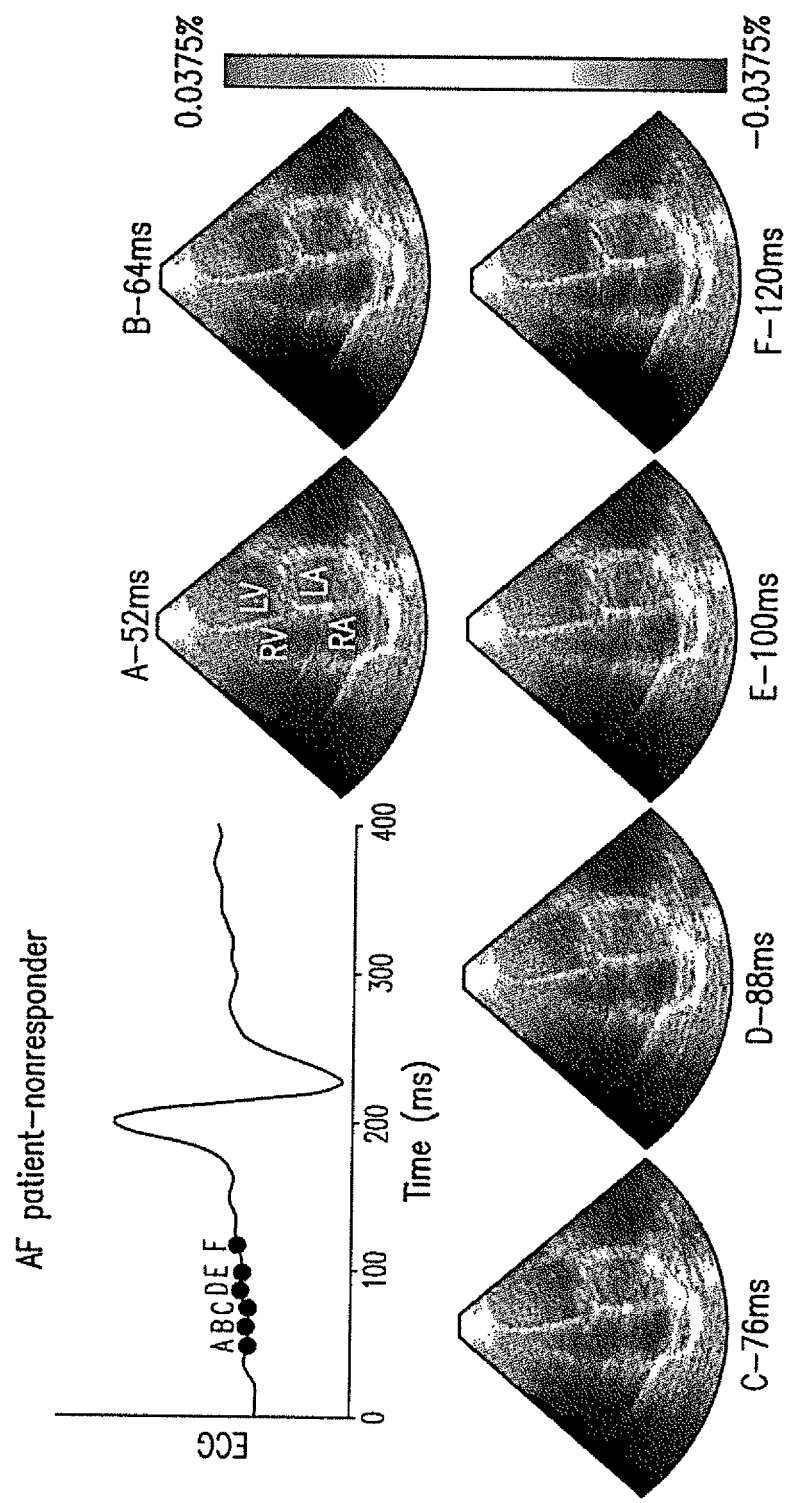
Figure 8C:
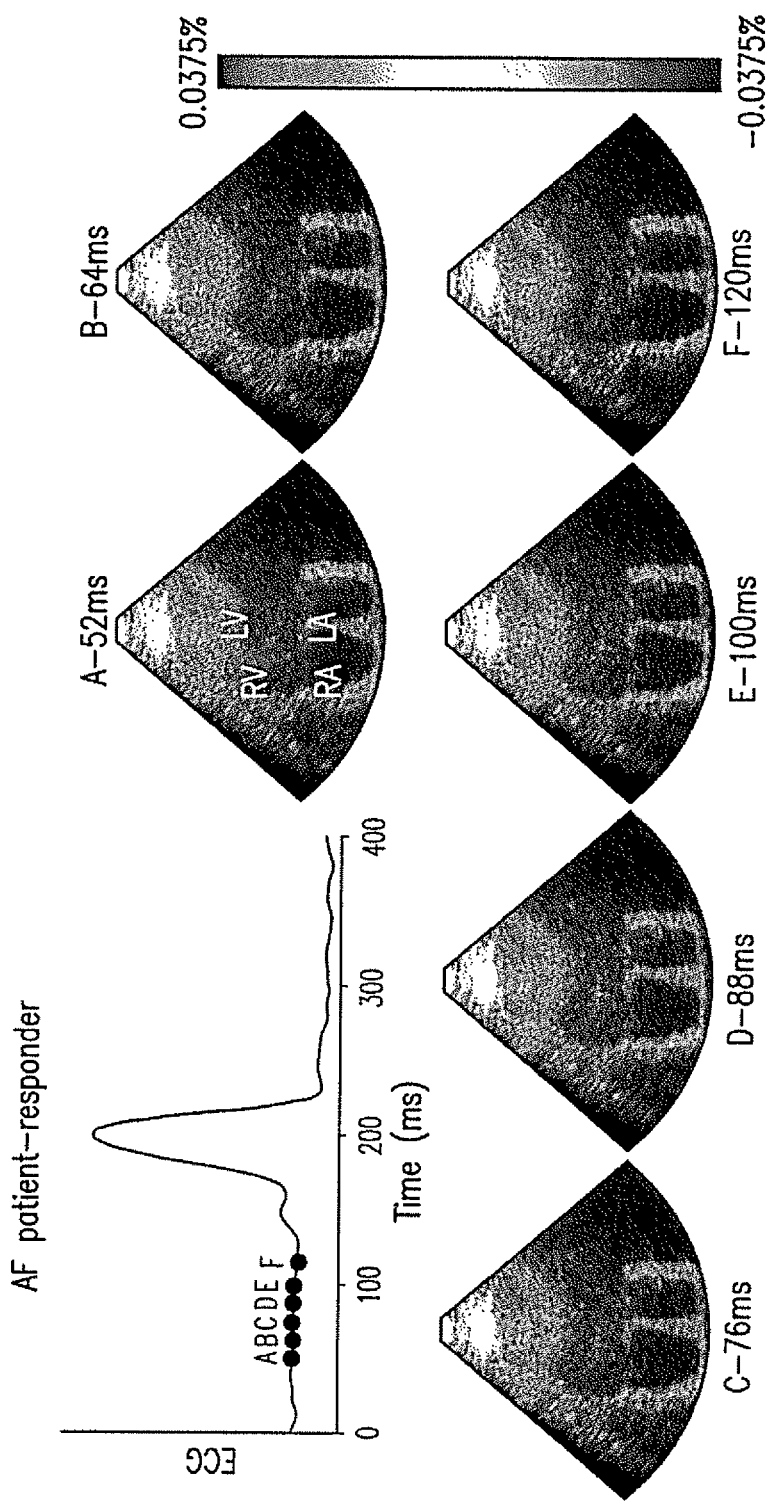
Figures 9A, 9B:
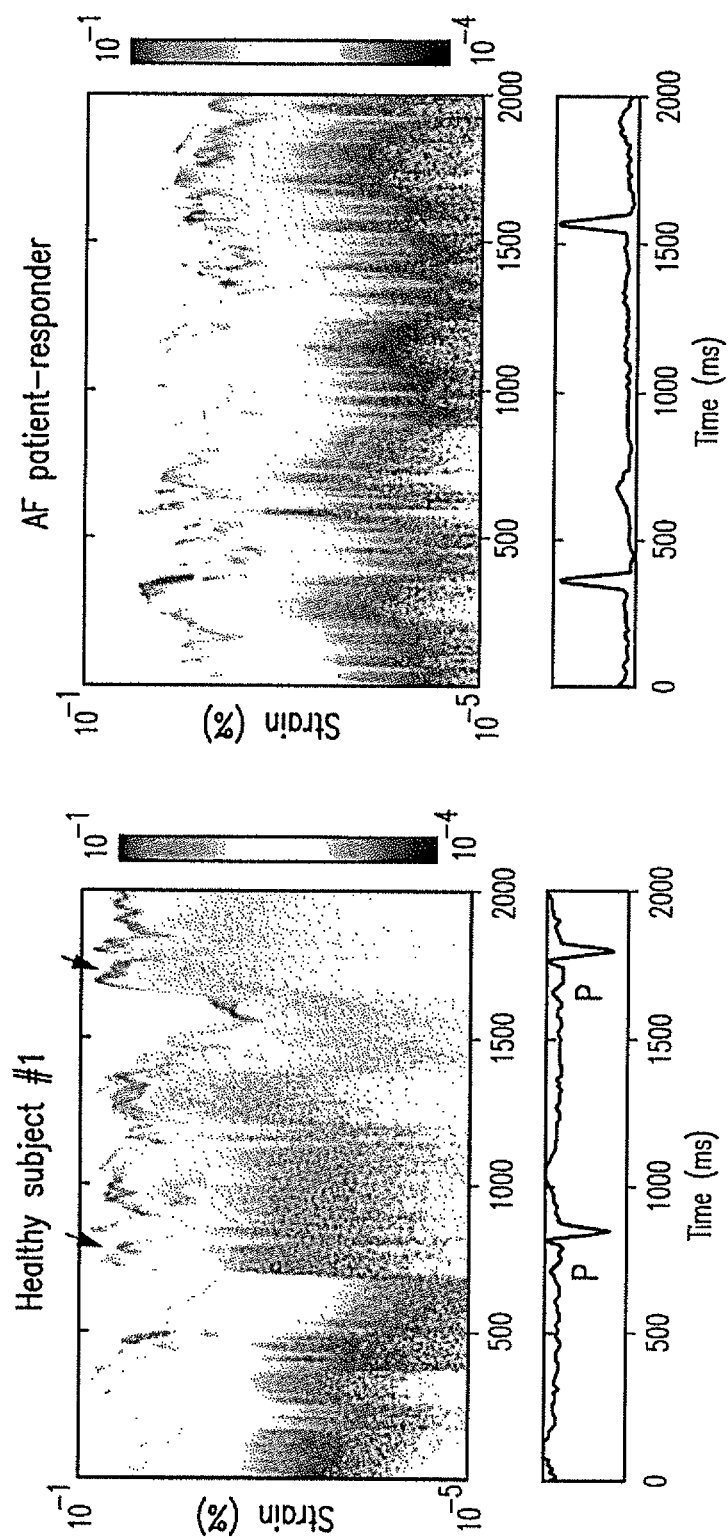

With reference now to FIGS. 8A-8C, an example of atria activation in a healthy subject is illustrated on top, an example of an AF patient non-respondent to cardioversion is illustrated in the middle, and an AF patient respondent to cardioversion is illustrated on bottom. The frames of FIGS. 8A-8C are frames taken from the respective EWI videos at the time portions shown in the corresponding ECG graph, and activated regions are shown in negative incremental strains in the four chamber apical view. The LV, RV, LA and RA portions are marked. In the healthy subject, the activation is shown in the RA and propagates to the LA until both atria are activated. In the AF subjects, no clear activation sequence is illustrated.

Referring now to FIGS. 9A-9D, strain distributions as a function of time are illustrated for two healthy subjects and two AF patients (respondent and non-respondent to cardioversion, respectively) are illustrated. A higher range strain variation can be seen in the healthy subjects, with increased strain values observed shortly after the P-wave (P) corresponding to contraction of the atria, as shown. In both AF patients, the strain magnitude in the atria is increased throughout the cardiac cycle and, in contrast to the healthy subjects, the changes are more rapid and with little or no apparent periodicity.

Figure 10A:
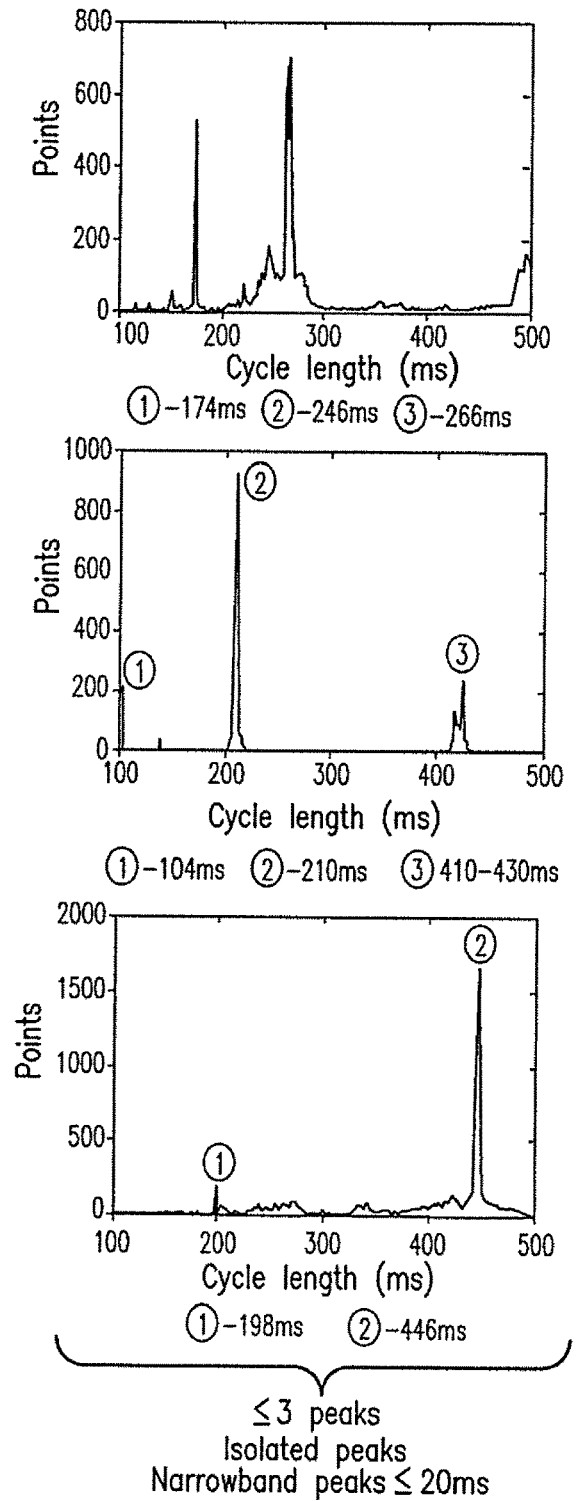
FIGS. 10A-10B each illustrates further details of the exemplary techniques of FIGS. 7A-7E.
Figure 10B:
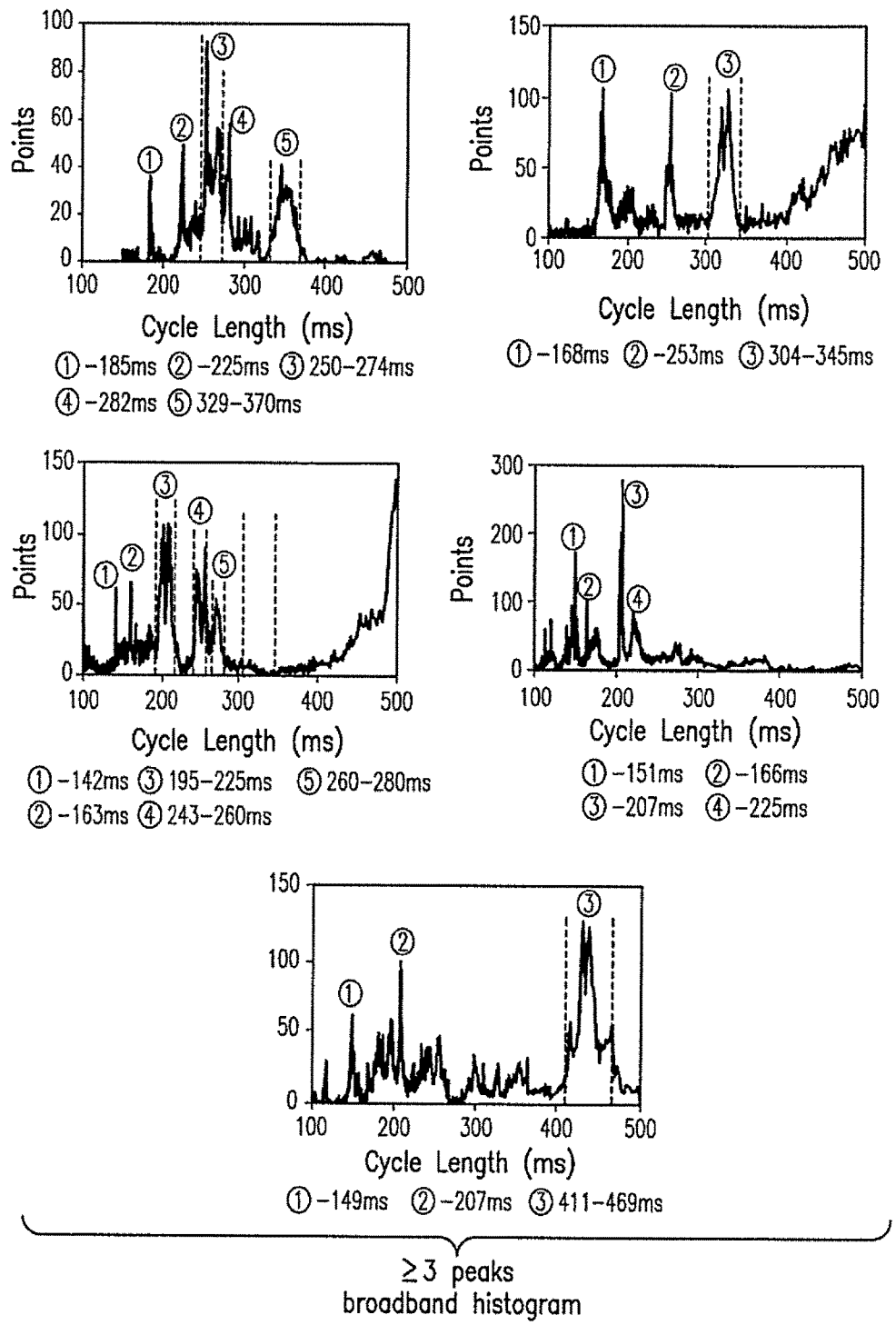

With reference now to FIGS. 10A-10B, histograms of cycle lengths observed in the atria of each of 8 different AF patients are shown. Comparing FIG. 10A with FIG. 10B, two patterns are illustrated. That is, in FIG. 10A, isolated narrowband peaks (i.e., 3 or less peaks, each lasting 20 ms or less) are shown in each of the 3 histograms. By comparison, as shown in FIG. 10B, relatively broadband histograms with more peaks (i.e., 3 or more peaks) are shown in each of the 5 histograms. Furthermore, the patients of FIG. 10A can each be considered a responder to cardioversion. By comparison, the patients of FIG. 10B included both responders and non-responders to cardioversion.

In the healthy patients, the histogram peaks corresponded to cycle lengths which correlated with the measured heart rate of 50-80 beats per minute (i.e. 752-1205 ms). In the AF patients, histogram peaks corresponded to shorter cycle lengths (i.e., 150-400 ms) and the detected peaks were either wideband (i.e., 50 100 ms width) and centered on multiple cycle lengths or narrowband (i.e., 10-30 ms width) and centered on a single cycle length. The shape of the histogram correlated with the success of the cardioversion as histograms with single narrow peaks (n=2) resulted in successful cardioversions whereas histograms with numerous wide peaks (n=2) resulted in unsuccessful cardioversions.

According to the techniques of the disclosed subject matter, techniques for frequency-based processing of the EWI images for analysis of AF and cardioversion are provided. EWI can allow for differentiation between normal rhythm and AF. In healthy subjects, frequency analysis showed that the cycle length distribution histogram peak correlated with the heart rate. In AF patients, the shape of the histogram correlated with success of the cardioversion. As such, EWI can be utilized for imaging AF, as well as for predicting the success of cardioversion treatment.

According to yet another aspect of the disclosed subject matter, the systems and techniques described herein can be utilized to plan and monitor treatment of arrhythmias. For example and without limitation, in one embodiment, a series of two or more images of the heart can be acquired at one or more pixel locations, each pixel location corresponding to a region of the heart. Image data corresponding to the one or more pixel locations during the series of images can be obtained. An image processor can be utilized to measure a periodicity of the image data for each of the one or more pixel locations over the series of images. The periodicity can correspond to an electromechanical signal or wave of the heart in the region corresponding to the measured one or more pixel locations.

The electromechanical signal or wave can be analyzed as described herein, for example using the image processor, to determine patterns characteristic of certain arrhythmias, such as atrial flutter, fibrillation, tachycardia and the like. If the electromechanical signal or wave indicates a focal arrhythmia, such as preventricular contraction and focal atrial tachycardia, electromechanical wave imaging (EWI) methodology can be used, as described herein, to identify the location of the focal zone and the subsequent propagation of cardiac activation. Additionally or alternatively, if the electromechanical signal or wave indicates a reentrant arrhythmia, such as atrial flutter and fibrillation, Fourier analysis of the strains can be performed as described herein, for example to reveal highly correlated mechanical and electrical cycle lengths and propagation patterns. Furthermore, if the electromechanical signal or wave indicates atrial flutter, intracardiac echocardiography (ICE) strains can be used to provide real-time imaging of the heart to identify anatomic structures and guide ablation to treat the arrhythmia, as described herein.

Additionally or alternatively, certain treatment can be performed and monitored. For example, if ablation, such as RF ablation, is performed, myocardial strains can be measured with ICE at a high temporal resolution in vivo and differences in strain can be measured with ICE, each as described herein, before and after radio-frequency ablation. For purpose of illustration and not limitation, monitoring of strains induced by RF ablation is described herein. However, monitoring of strains induced by any ablation technique, for example and without limitation, cryoablation, microwave ablation, ultrasound ablation, laser ablation, can be performed using the techniques described herein.

According to yet another aspect of the disclosed subject matter, techniques for electromechanical cycle length mapping (ECLM) are provided. ECLM can be used, for example and without limitation, for estimating the electromechanical activation rate, or cycle length, e.g., the rate of the mechanical activation of the myocardium following electrical activation. ECLM can utilize frequency analysis of incremental strain within the atria and can be performed in a single acquisition. ECLM can be used, for example and without limitation, to non-invasively characterize atrial arrhythmias and provide feedback on the treatment planning of catheter ablation procedures in the clinic.

ECLM can utilize ultrasound to perform non-invasive transmural estimation of incremental strain, which can also be referred to as inter-frame strain, in the myocardium at high temporal and spatial resolution. ECLM can include analysis of a frequency component of the incremental strain and, additionally or alternatively, of the frequency and rate of activation regardless of an origin of activation. As such, ECLM can be suitable for characterization of non-periodic arrhythmias, for example and without limitation AF and other arrhythmias where choosing an origin of activation does not apply.

Techniques for ECLM can include mapping the electromechanical activation rate of the entire atrium in a single acquisition. An atrial tachycardia model can be generated by pacing the heart from the left atrial appendage at a rate within the range reported during atrial fibrillation. Maps and histograms of the cycle length during pacing can be compared to a known pacing rate and correlation between the paced and detected rate can be computed. The effect of the length of acquisition on the ECLM quality can be evaluated by comparing results obtained from, for example and without limitation, 1 s, 2 s and 4 s long acquisitions. Reproducibility of ECLM techniques can be confirmed by comparing maps and histograms from consecutive acquisitions.

In one example, for purpose of illustration and confirmation of the disclosed subject matter, six male adult mongrel canines weighting 24.1±0.4 kg were evaluated. The canines were anesthetized with an intravenous injection of diazepam (0.5 1.0 mg·kg-1) or an intra-muscular injection of hydromorphone (0.05 mg·kg-1) as premedication, and methohexital (4-11 mg·kg-1) as induction anesthetic. Anesthesia was maintained by a mixture of oxygen and isoflurane (0.5-5.0%) delivered through mechanical ventilation via a rate- and volume-regulated ventilator. Morphine (0.15 mg·kg-1, epidural) was administered before surgery and lidocaine (50 µg·kg-1.h-1, intravenous) was used during the procedure. A 0.9% saline solution was administered intravenously at 5 mL·kg 1.h-1 to maintain blood volume. Oxygen, peripheral blood pressure, and temperature were monitored. Limb leads were placed for surface electrocardiogram (ECG) monitoring. The chest was opened by lateral thoracotomy using electrocautery. A pacing electrode was sutured to the left atrial appendage. Pacing rates were chosen to be within AF and atrial flutter (AFL) range and ranged from 150 to 500 ms (see, e.g., Table 1). Data acquisition was performed on free-breathing, open-chest canines during pacing from the LAA, which was confirmed by monitoring of the ECG. Data was acquired during 18 different setups, or pacing schemes, as shown in Table 1.

TABLE 1

Summary of pacing rates and number of corresponding acquisitions.

| Pacing Rates (ms) | | | | | | | |
|---|---|---|---|---|---|---|---|
| 150 | 170 | 200 | 250 | 300 | 350 | 400 | 500 |

| Number of acquisitions | | | | | | | |
|---|---|---|---|---|---|---|---|
| 2 | 1 | 5 | 4 | 3 | 1 | 1 | 1 |

ECLM was performed in the four-chamber, two chamber, long-axis and "3.5-chamber" echocardiographic apical views during pacing from the LAA. The apical 3.5-chamber view can correspond to an apical view taken in between the four and two-chamber views. ECLM can utilize Radio Frequency (RF)-based motion estimation and gradient operators to map transient deformations, which can be referred to as strains, occurring during electrical activation of the myocardium. As described herein, a suitable frame rate can be utilized for precise estimation of displacement and cardiac strain. In this manner, the frame rate can be sufficiently high to reduce or prevent decorrelation at a high strain value due to loss of motion information in the phase of the signal, but sufficiently low to reduce or prevent incorruption from electronic noise at a low strain value. For purpose of illustration and not limitation, and as embodied herein, a frame rate between 500 Hz and 2000 Hz can provide suitable SNR for incremental strain estimation.

Referring now to FIG. 11-1, an unfocused transmit sequence can be utilized, for example and without limitation, as embodied herein, using a Verasonics system (Verasonics, Redmond, Wash.) to acquire RF frames at 2000 fps using a 2.5 MHz ATL P4 2 phased array. Such a high frame rate can be achieved by emitting unfocused, spherical ultrasound waves using a virtual focus located 10.2 mm behind the array. Beamforming on the raw signals obtained from each of the elements, e.g., signals as recorded by each of the element without any processing or filtering, can be performed during post-processing, resulting in reconstruction of one RF frame per transmission. B-mode images can thus be reconstructed from the unfocused transmit sequences, and can have lower resolution and SNR. As such, segmentation can be challenging, and thus a 64 line, B-mode acquisition can performed following the initial high frame rate acquisition. In this manner, for purpose of illustration and not limitation, the acquisition sequence can include 2 s or 4 s of high frame rate acquisition at 2000 fps (4000 or 8000 frames acquired), along with an anatomical imaging sequence including 1.5 s of 64 line, B-mode acquisition at 30 fps, as illustrated for example in FIG. 11-1. The lengths of acquisition can be chosen according to heart rate and/or pacing rate to acquire a suitable amount of data over at least a couple of cardiac cycles. Retrospective ECG-gating can be used to temporally align the high frame rate acquisition with the anatomical B-mode acquisition.

In this example, RF frames were reconstructed in polar coordinates from raw signals obtained from the probe elements using a delay-and-sum algorithm. The reconstructed images had an angular sampling of 0.7° or 0.025 rad (128 lines spanning 90°) and an axial sampling frequency of 20 MHz (axial sampling of 0.0385 mm). Segmentation of the myocardium was manually initialized on the first frame of the anatomical B-mode sequence, and the endocardial contour was automatically tracked throughout the cardiac cycle using the estimated displacements. With reference to FIGS. 11-2(a) to 11-2(b), displacement estimation was performed using a fast, 1D cross-correlation algorithm with overlapping 9.2 mm axial windows (15 wavelengths) and a 0.385 mm window shift (96% overlap).

For purpose of illustration and not limitation, as embodied herein, a window size in the range of 10 to 15 wavelengths can provide suitable results for motion estimation. A suitably large window size can improve SNR and reduce jitter errors of motion estimation, while an exceedingly large window can increase intra-window deformation and thus affect the spatial resolution of motion estimation. Spatial resolution for motion estimation can be determined by the window shift (or overlap), which for purpose of illustration and not limitation, as embodied herein, can be 0.385 mm and can be chosen increase or maximize the resolution for estimation.

In this example, with reference to FIGS. 11-3(a) to 11-3(b), axial incremental strains (e.g., inter-frame strain in the axial direction) were estimated using a least-square estimator with a 5 mm, 1D-kernel. Strain estimates were filtered using a 12 mm by 10 beams moving average spatial filter and a temporal low-pass filter with a 125 Hz cut-off frequency. Displacement and strain estimation was performed in polar coordinates, which were converted to Cartesian coordinates.

A cycle length parameter can measure the electromechanical activation rate during ablation. To estimate the period of activation in the atria during pacing, e.g., the cycle length, the frequency spectra of all points in the atria can be obtained by applying a Fast Fourier Transform (FFT) to the previously estimated incremental strain curves. The FFT of an N-point signal can provide the N-point discrete Fourier transform with a highest resolvable frequency of fs/2, and a frequency resolution that can be represented as df=fs/N, where df can represent the frequency resolution, fs can represent the sampling frequency of the signal, and N can represent the number of samples acquired. To obtain a frequency resolution of df=0.01 Hz, each strain curve can be resampled to an appropriate frequency following the equation for the FFT frequency resolution. The resampled strain curves can be zero-padded if suitable to match the initial length of the signal acquired before applying the FFT. As such, applying the FFT to 1 s, 2 s and 4 s long signals acquired at 2000 Hz (corresponding to 2000, 4000 and 8000 samples-long signals, respectively), the strain curves can be resampled to 20, 40, and 80 Hz, respectively. In this manner, frequencies ranging from 0 to 10, 20, and 40 Hz, respectively, can be detected. The FFT can be applied to strain curves obtained at each point within the mask of the atria, and from each resulting frequency spectrum, the dominant frequency (DF) can be detected and can be converted to cycle length, as shown for example in FIGS. 12-2(a) to 12-1(c).

Referring now to FIGS. 12-1(a) to 12-2(b), cycle length maps can be generated for each of the apical views (e.g., 4 chamber, 2-chamber, 3.5 chamber and long-axis) by plotting the cycle length detected at each point within the mask, as shown for example in FIG. 12-2(a). From these maps, pseudo-3D cycle length maps can be generated for each acquisition, as shown for example in FIG. 12-2(b). Histograms of the cycle lengths in the atria during pacing can be generated for each view, and each single-view histogram can be included into a single histogram per acquisition at a given pacing rate, as shown for example in FIG. 12-3(a). From the histograms, the global cycle length for each acquisition can be detected by sliding a 10 ms-wide window over the range of cycle lengths. The value at the center of the window containing the majority of the regions in the atria can be taken to represent the global cycle length for the considered acquisition, and in some embodiments, the global cycle length can include at least 50% of all regions in the atria, as shown for example in FIG. 12-3(b).

Figure 15:
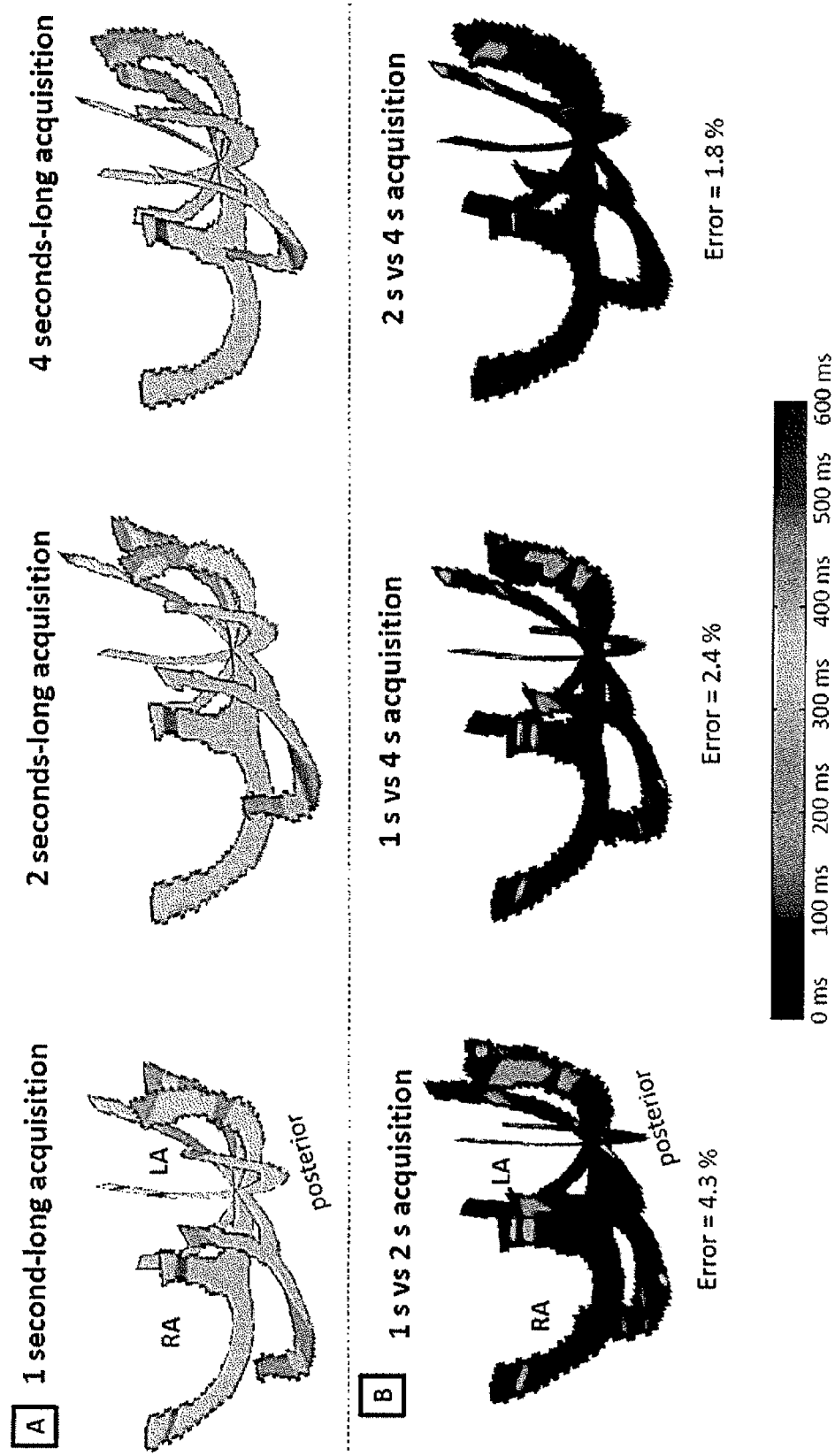
FIG. 15 illustrates further details of the exemplary techniques of FIGS. 12-1(a) to 12-3(b).
Figure 16:
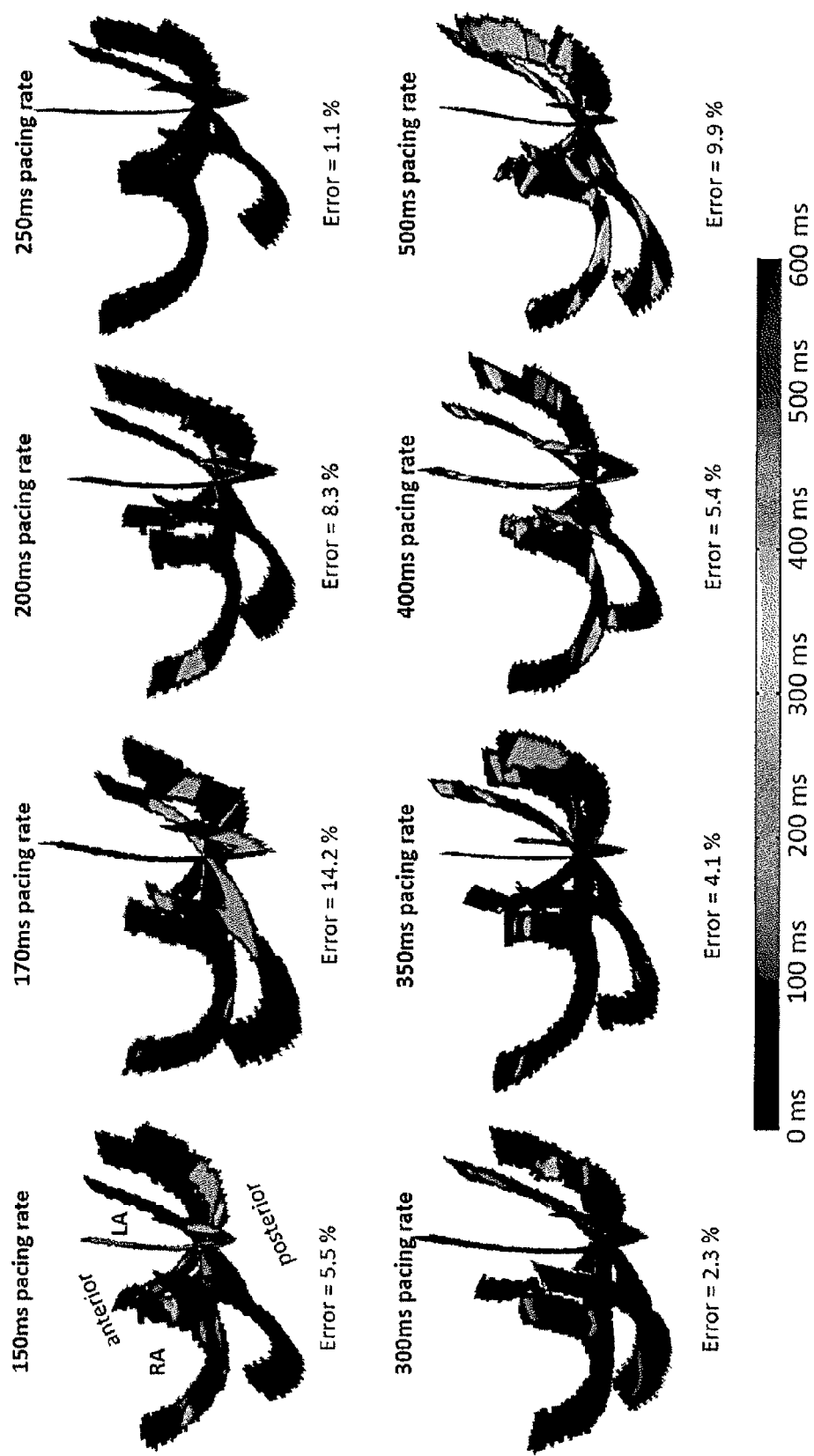
FIG. 16 illustrates further details of the exemplary techniques of FIGS. 12-1(a) to 12-3(b).

With reference to FIGS. 15 and 16, varying lengths of acquisition (FIG. 15) and successive acquisitions (FIG. 16) can be compared by generating maps of the absolute difference of corresponding views between two acquisitions for example, successive acquisitions or acquisitions of varying lengths. Pseudo-3D difference maps can be generated from these maps. For purpose of illustration and not limitation, as embodied herein, a quantitative metric of the difference can be determined by computing the sum of the absolute difference (SAD) between ECLM maps from each type of acquisitions and by expressing that value relative to the average sum of all cycle lengths within the mask between the two acquisitions. The resulting value can be referred to as the error, and can be represented as follows:

$$\text{error} = \frac{\sum_{1}^{M} |f(i) - g(i)|}{1/2 \sum_{1}^{M} (f(i) + g(i))} \quad (1)$$

where f and g can represent the maps of the ECLM-detected cycle length for the first and second acquisition, respectively, and M can represent the total number of points in the segmented region.

Figure 13:
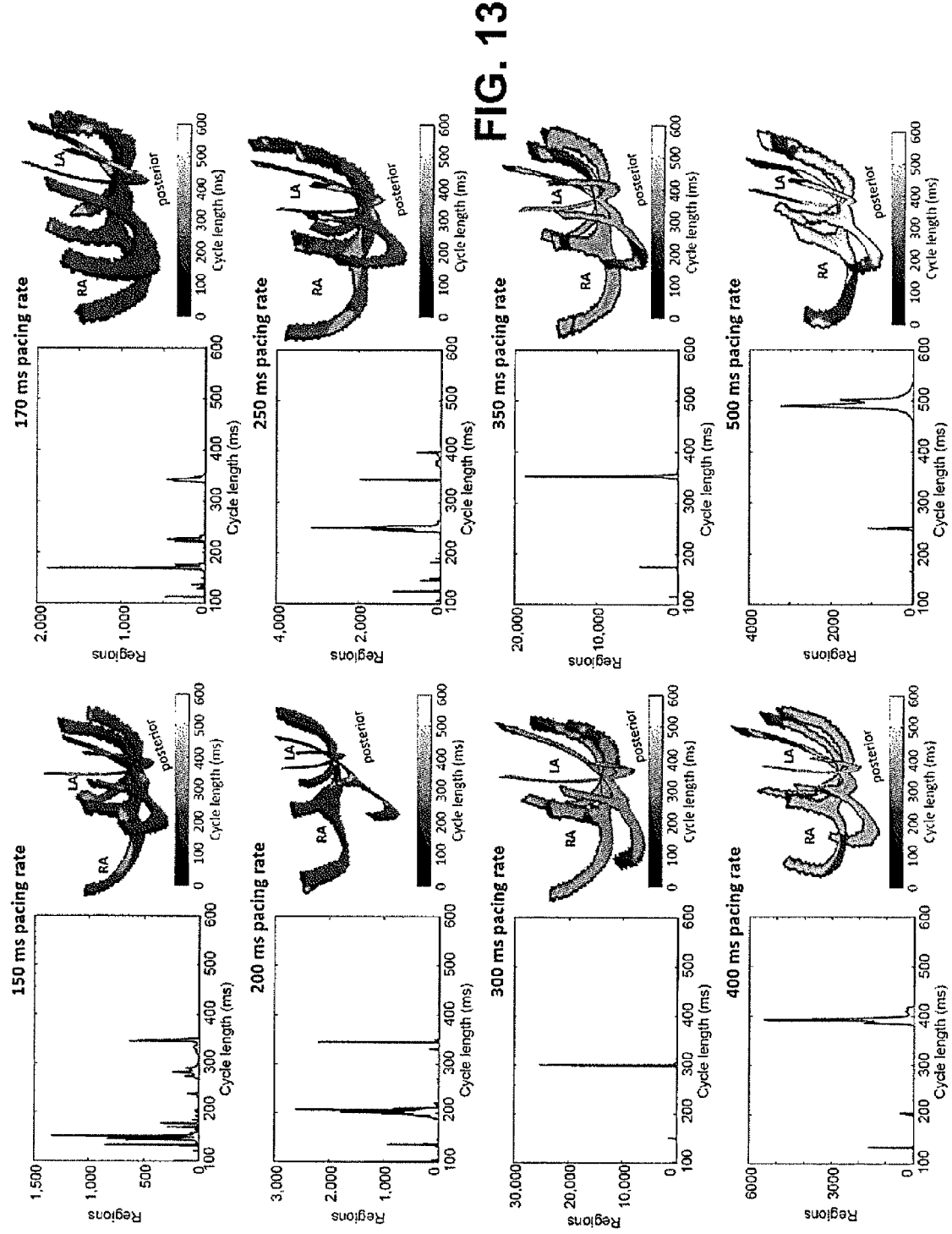
FIG. 13 illustrates exemplary histograms and cycle length maps illustrating further details of the exemplary techniques of FIGS. 12-1(a) to 12-3(b).

Referring now to FIG. 13, histograms and cycle maps in canines in vivo during pacing from the LAA are shown. In these examples, the rates of pacing ranged from 150 to 500 ms. As embodied herein, pseudo-3D cycle length maps can be shown with the posterior side facing front. Additionally, and as embodied herein, for each pacing rate, the global maximum on the histogram can correspond to the pacing rate. As shown for example in FIG. 13, and as embodied herein, as the pacing rate decreases, the global maximum in the histogram becomes clearer. As such, in this example, for pacing at 150 through 250 ms, although the global maximum is at the pacing rate, numerous local maxima located around the pacing rate are shown. For purpose of illustration and not limitation, and as embodied herein, cycle length maps presented next to the corresponding histogram can confirm that most or all of the atria activated at the same cycle length as the pacing rate. Furthermore, and as embodied herein, as the pacing rate decreases, the cycle length maps become more uniform, which can indicate a bigger percentage of the atria activates at the pacing rate.

Figure 14:
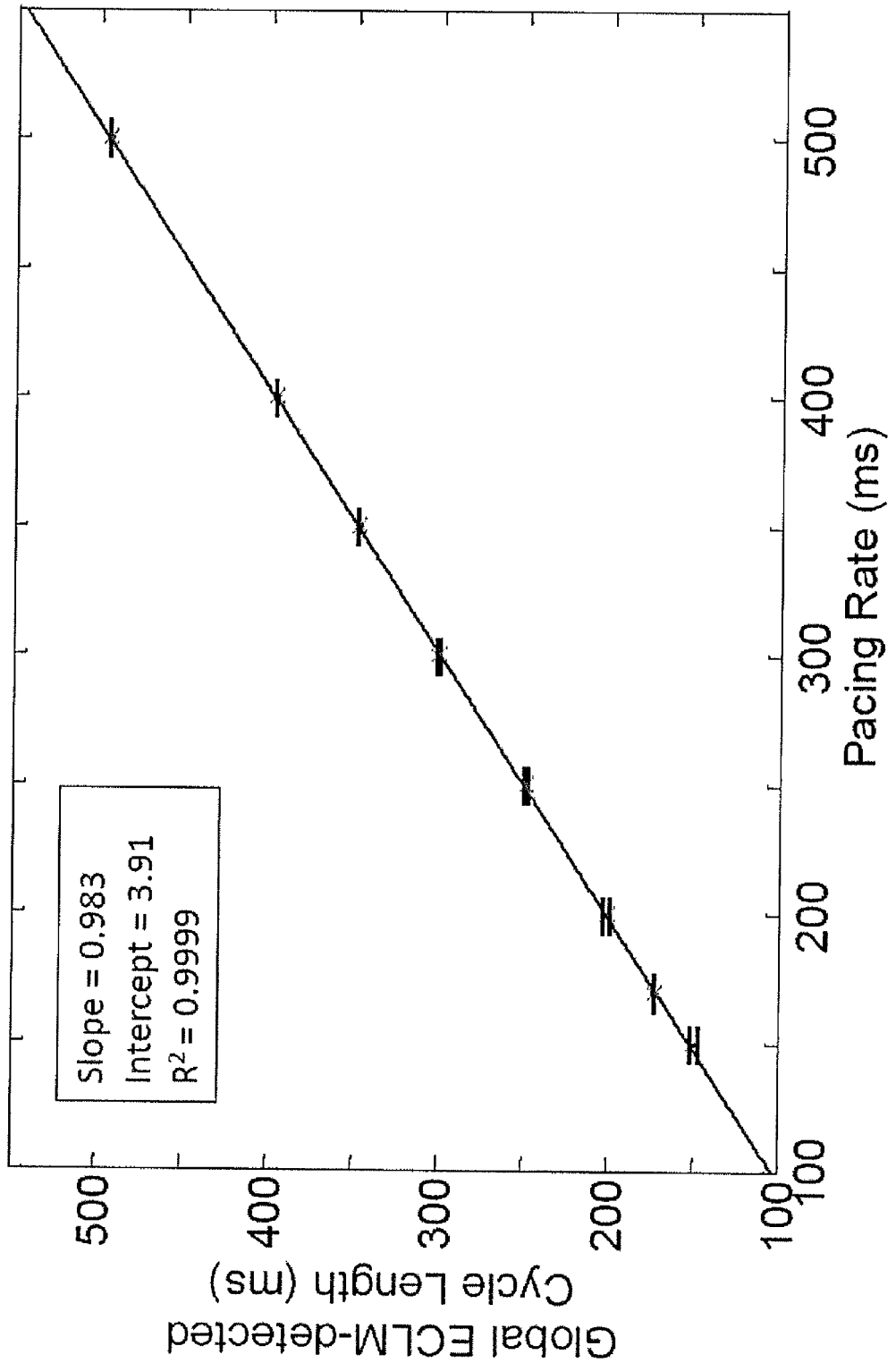
FIG. 14 illustrates further details of the exemplary techniques of FIGS. 12-1(a) to 12-3(b).

Referring now to FIG. 14, a chart illustrating the global ECLM-detected activation cycle length, as described herein, compared with the LAA pacing rate is shown. For purpose of illustration and not limitation, and as embodied herein, the chart was obtained by considering 18 points, each corresponding to the different pacing schemes described above in Table 1. For each pacing scheme, the average value and standard deviation of the global ECLM-detected activation cycle lengths were determined from all acquisitions, as applicable. A summary of the determined values is shown in Table 2. A correlation between the ECLM-detected activation cycle lengths and the underlying pacing rate was obtained.

TABLE 2

Summary of the global ECLM-detected activation rate for each pacing scheme and of the corresponding global ECLM-detected activation cycle lengths.

| Pacing Rate (ms) | Global Activation Rate (ms) | ECLM-detected Cycle Length (ms) |
|---|---|---|
| 150 | 151.3 147.7 | 149.5 ± 2.5 |
| 170 | 172.4 | 172.4 |
| 200 | 200.4 202.8 201.2 200.3 198.8 | 200.7 ± 1.5 |
| 250 | 248.1 250.6 248.8 249.4 | 249.2 ± 1.1 |
| 300 | 300.3 301.2 300.8 | 300.8 ± 0.5 |
| 350 | 348.6 | 348.6 |
| 400 | 396.8 | 396.8 |
| 500 | 495.1 | 495.1 |

Referring now to FIG. 15, effects of the length of acquisition on the performance of ECLM is illustrated. In this example, the difference between 1 s, 2 s and 4 s long acquisitions during pacing at 350 ms was examined. Comparison of the corresponding cycle length maps illustrates that, qualitatively, all three CL maps are similar, as shown for example in FIG. 15(a). Absolute difference maps are also illustrated, and in this example, show that the cycle length maps differ in localized areas, as shown for example in FIG. 15(b). The error was determined to be 4.3% between 1 s and 2 s long acquisitions, 2.4% between 1 s and 4 s long acquisitions, and 1.8% between 2 s and 4 s long acquisitions.

Referring now to FIG. 16, ECLM reproducibility can be demonstrated by comparing ECLM results between consecutive 2 s long acquisitions for each of the pacing rates described herein. In this example, most or all of the difference maps show that the differences between corresponding acquisitions are low, except in some localized areas, which can be located, for example and without limitation, near the base in the lateral wall of the LA (350 ms case) or in the septum (170, 300 and 350 ms cases), and/or at the mid-level in the lateral wall of the RA (200 ms case). A wide region of error was determined while pacing at 170 ms in the posterior atrial apical region. This region corresponded to an absolute error of 170 ms, and as such, for one of the acquisitions, ECLM determined the region to be activating only once every two pacing cycles. Cases corresponding to pacing at 400 ms and 500 ms illustrate regions of relatively higher errors than in other pacing case. Additionally, pacing at 500 ms illustrates a relatively higher number of errors. The errors between cycle length maps from consecutive acquisitions are summarized in Table 3. Reproducibility error was determined to be less than 10% for all cases, except pacing at 170 ms, with pacing at 250 and 300 ms showing the least errors. The average error between consecutive acquisitions was determined to be 6.3±4.3%.

TABLE 3

Summary of errors between consecutive acquisitions for all pacing rates.

| | Pacing Rates (ms) | | | | | | | |
|---|---|---|---|---|---|---|---|---|
| | 150 | 170 | 200 | 250 | 300 | 350 | 400 | 500 |
| Error (%) | 5.5 | 14.2 | 8.3 | 1.1 | 2.3 | 4.1 | 5.4 | 9.9 |

For purpose of illustration and not limitation, as embodied herein, ECLM can map the cycle length of electromechanical activation of the heart noninvasively. Furthermore, and as embodied herein, ECLM can be applied against well-defined and controlled heart rhythms to provide analysis of more complex atrial arrhythmias, for example and without limitation, atrial fibrillation or flutter.

As described herein, ECLM can include characterization of the electromechanical activation of the heart using motion and strain estimation techniques on RF signals. The electromechanical activation of the heart can correspond to an electrical activation pattern with a delay of a few milliseconds, and can correspond to the initial time point, at which the cardiac muscle starts its contraction. ECLM can analyze the frequency information of the electromechanical activation, e.g., the periodicity at which the heart activates. ECLM can thus analyze arrhythmias, such as fibrillation, where the heart can be considered to activate chaotically on a global scale, whereas, locally, regions of the myocardium can be considered to activate at various rates, which can be mapped by ECLM.

ECLM can detect frequencies of activation, or cycle lengths, for more organized arrhythmias, for example and without limitation, tachycardia. FIGS. 13 and 14 both illustrate that ECLM can detect the pacing rate of the atria from the LAA. As embodied herein, the pacing rates can range from 150 ms to 500 ms, which can be considered within the range of cycle lengths for AF. Cycle length maps for each of the pacing rate can illustrate that most or all of the atria can be activated at a cycle length corresponding to the pacing rate. Histograms can further illustrate this as the global maximum detected at a cycle length corresponding to the pacing rate. At the fastest pacing rates, both the map and the histogram can show that some regions in the heart can activate relatively slowly, e.g., at a higher cycle length, than the expected pacing rate. In the frequency domain, these can correspond to subharmonics of the fundamental frequency of activation corresponding to the pacing rate.

Subharmonics can be a result of several phenomena. For example, and as embodied herein, the refractory period of cells in the myocardium can be longer than the rate at which the atria are paced. The refractory period duration in normal cardiac cells can be about 200-240 ms, but can reduce to 80-85 ms during AF. As such, parts of the atria can be unable to be captured with every pacing beat, resulting in a 2:1 or 3:1 activation pattern in those regions, which can results in regions presenting a higher cycle length. Additionally or alternatively, ventricular contractions can occur, and in this manner, for example at a fast pacing rate, the ventricle can be able to be captured only every 2 to 3 pacing beats. When contracting, the ventricles can affect atrial electromechanical activation via tethering of the cardiac tissue, which can result in lower apparent activation.

Although ECLM can utilize the frequency content of the incremental strain curve and, as such, utilizes a periodic change in the incremental strain curves to derive information about cycle length, in addition or as a further alternative, incremental strain can be estimated in the longitudinal direction, and thus can introduce an inherent angle dependence. In this manner, the walls of the heart can be aligned with the longitudinal direction, and incremental strain can alternate between negative values during systole, e.g., contraction, and positive values during diastole, e.g., lengthening. Alternatively, the wall can be perpendicular to the longitudinal direction, and incremental strain can alternate between positive values during systole, e.g., thickening of the wall during contraction, and negative values during diastole, e.g., thinning of the wall. As a further alternative, the walls can be aligned such that the longitudinal direction intersects the myocardium at an angle close to 45°, and the magnitude of the changes in incremental strain can be lower than when the wall is directly aligned or perpendicular to the direction of estimation, which can in turn result in noise and thus reduce accuracy of estimation. At longer pacing rates (e.g., 250-500 ms), some regions in the atria can contract about twice as fast as the pacing rate, for example due to peak hopping. That is, in these regions uncertainties in the strain estimation can result in noisy incremental strain curves as well as spectral distortion. Such factors can lead to peaks corresponding to harmonics of the fundamental frequency, e.g., the pacing frequency, having higher amplitudes in the frequency domain than the peak corresponding to the pacing frequency. As such, incorrect dominant frequencies can be estimated and a cycle length can be detected that is half of the pacing cycle length.

Referring now to FIG. 15, the effect of the length of acquisition on the ECLM performance is illustrated. In this example, the different lengths of acquisition were chosen such that at least two pacing cycles were acquired for all pacing rates. FIG. 15 shows only minor differences between the 1 s, 2 s and 4 s long acquisitions both qualitatively and qualitatively, as all three CL maps can be considered qualitatively similar, and the values for the error between the acquisitions were below 5%. The error between the 2 s and 4 s long acquisitions was the lowest at 1.8%. For the 1 s long acquisitions, results were slightly noisier although they still correctly detected the global CL at the pacing rate. In this example, to obtain the desired frequency resolution when applying the FFT algorithm, the incremental strain curve signals were resampled. For purpose of illustration and not limitation, 2 s and 4 s long signals were resampled at 40 Hz and 80 Hz, which allowed detection of frequencies up to 20 Hz and 40 Hz, respectively. Compared to certain ranges of frequencies e.g., 1.7 Hz to 10 Hz (or, cycle lengths from 100 ms to 600 ms), the sampling was suitable for accurate mapping.

For the 1 s long acquisition, the signal was resampled at 20 Hz, which allowed for detection of frequencies up to 10 Hz, which can account for slightly less even results compared to longer acquisition lengths. As such, acquisition lengths of at least 1 s can be sufficient, and acquisition lengths of at least 2 s can provide improved results. Technical considerations for improving the quality of dominant frequency analysis can include averaging multiple electrocardiograms to improve precision as well as increasing the length of acquisition, with at least 2 s being suitable for accurate estimation. Furthermore, although point-by-point acquisition of the electrocardiograms can be performed, simultaneous signal acquisition can reduce both the temporal and spatial variability of dominant frequency analysis. As such, ECLM can overcome certain challenges currently attributed to conventional techniques, among other things, by enabling simultaneous, whole-atria acquisition.

Referring now to FIG. 16, ECLM can be shown to be reproducible across the range of pacing rates described herein, including results for cycle length in the range of 250 to 350 ms being relatively more reproducible. In this example, a model of arrhythmia which produced organized rhythms was considered. By pacing the atria at pre-determined pacing rates, a canine atrial tachycardia model was obtained where most of the myocardium was expected to activate at a similar rate. Additionally or alternatively, when considering more complex arrhythmias such as AF, the global activation rate can be considered less adapted due at least in part to the chaotic nature of activation during AF resulting in regions activating at different rates across the atria, and due at least in part to the presence of drivers less spatiotemporally stable, which can include meandering re-entry circuits and rotors. ECLM can allow for simultaneous mapping of the whole atria in a single heartbeat, and can be used for analysis of local activation rates in a neighborhood of points within the myocardium. As such, analysis of AF drivers and guiding or shortening of the duration of treatment of such arrhythmias can be performed. In this manner, ECLM can be used for planning and follow up for the characterization of atrial arrhythmias, such as AF or AFL, for example and as embodied herein, by non-invasively and transthoracically providing analysis of the underlying diseases, and can reduce the duration while increasing the success rate of catheter ablation procedures.

According to yet another aspect of the disclosed subject matter, techniques for intracardiac echocardiography (ICE) are provided. ICE can be used, for example and without limitation, for identifying anatomical structures during radiofrequency (RF) ablation procedures. For purpose of illustration and not limitation, as embodied herein, ICE can be used in adjunct with myocardial elastography (ME) to provide additional information on the mechanical properties of cardiac tissue and provide information on mechanical changes due to ablation. Additionally, for purpose of illustration, and as embodied herein, ICE can be used at high frame rate using a diverging beam transmit sequence to image myocardial strain and differentiate myocardial tissue properties before, during and after ablation for a clinical ablation procedure. Additionally or alternatively, and as embodied herein, ICE can be used as an imaging modality for lesion characterization, which can be performed without additional equipment or modification of the ablation procedure or clinical setup.

For purpose of illustration and not limitation, as embodied herein, exemplary techniques for ICE can include using myocardial elastography (ME) with ICE for assessment of the mechanical properties of the myocardium, a surrogate marker of electrical conduction, and thus can be used to characterize the extension and efficacy of ablation lesions. LA strain can be used to predict the success of AF ablation. Strains can be obtained with ME at a high frame rate and a large field of view of the heart. High frame rate ultrasound imaging can be achieved, for purpose of illustration and not limitation, with techniques such as composite imaging or parallel beamforming using plane wave or diverging beams. For example and without limitation, as embodied herein, diverging beams can allow for reconstruction of a large field of view at a high frame rate. As such, for purpose of illustration and not limitation, as embodied herein, exemplary techniques for ICE can include using diverging wave imaging and parallel beamforming with ICE to image myocardial strain at high temporal resolution during atrial emptying in vivo. Additionally or alternatively, as embodied herein, strain imaging can be used with ICE to differentiate myocardial tissue properties before, during and after ablation for a clinical ablation procedure.

For purpose of illustration and confirmation of the disclosed subject matter, in a first example, three male canines ranging from 23 to 25 kg in weight were premedicated with diazepam 0.5-1.0 mg/kg injected intravenously and then anesthetized with an intravenous injection of propofol 2 5 mg/kg. Each canine was mechanically ventilated with a rate- and volume-regulated ventilator on a mixture of oxygen and titrated 0.5 5.0% isoflurane. An ICE catheter was inserted into the jugular vein through a 10 F introducer sheath and advanced to the right atrium (RA).

Additionally, for purpose of illustration and confirmation of the disclosed subject matter, in a second example, eight patients (61.1±15.1 years old) underwent AF ablation, during which ICE was used as a component of their procedure. The ICE catheter was inserted into the femoral vein and advanced under direct fluoroscopic guidance to the right atrium. B-mode images of the right and left atrium with the ablation catheter in the ultrasound view were recorded. Ultrasound data were acquired before, during and/or after ablation in similar echocardiographic views and similar heart rhythm, as illustrated for example in Table 4.

TABLE 4

Patients scanned for different acquisitions

| Acquisition | Patients ID number |
|---|---|
| Reproducibility | #1, #2 |
| Before and after ablation | #3, #4, #5 |
| Before and during ablation | #3, #6 |
| After (t) and after (t + Δt) ablation | #4, #6, #7 |
| During and after ablation | #8 |

With reference to Table 4, for purpose of illustration and not limitation, two patients (Patient #1 and Patient #2) were investigated to carry out a reproducibility study. The number of patients for which data were acquired both before and after ablation was N=3 (Patient #3, Patient #4 and Patient #5). The number of patients for which data were acquired both before and during ablation was N=2 (Patient #3 and Patient #6). The number of patients for which data were acquired after ablation at different times was N=3 (Patient #4, Patient #6 and Patient #7). The number of patients for which data were acquired both during and after ablation was N=1 (Patient #8). RF ablation was either performed around the pulmonary veins, and/or cavotricuspid isthmus (CTI) and/or left atrium (LA).

Figure 17:
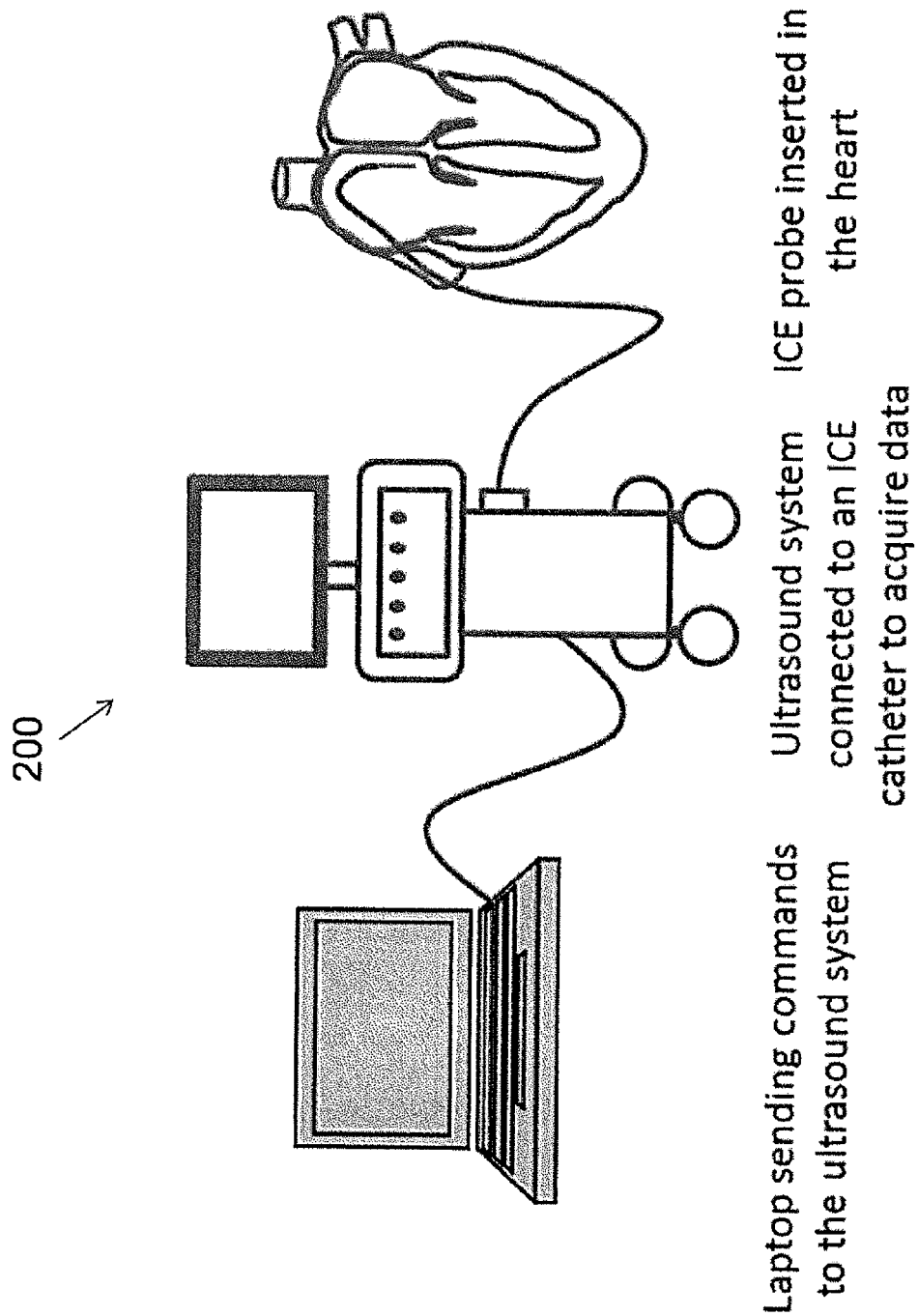
FIG. 17 illustrates an exemplary system for intracardiac echocardiography (ICE) according to another aspect of the disclosed subject matter.

Furthermore, for purpose of illustration and not limitation, and as embodied herein, a 5.8-MHz ICE catheter with 64 elements and 13 mm active aperture (ViewFlex PLUS ICE catheter, St. Jude Medical, St. Paul, Minn., USA) on an ultrasound system (Viewmate Z, St. Jude Medical, St. Paul, Minn., USA) was used. As embodied herein, the imaging depth was set to 90 mm to be able to image at least one heart chamber such as the left atrium. As shown for example in FIG. 17, exemplary ultrasound system 200 was connected to a computer via a serial cable, which allowed control over the parameters and the acquisition as well as data transfer to a hard drive connected to the ultrasound system 200. As embodied herein, high frame rate imaging was achieved by reconstructing the entire frame from a single beam transmit.

Figure 18:
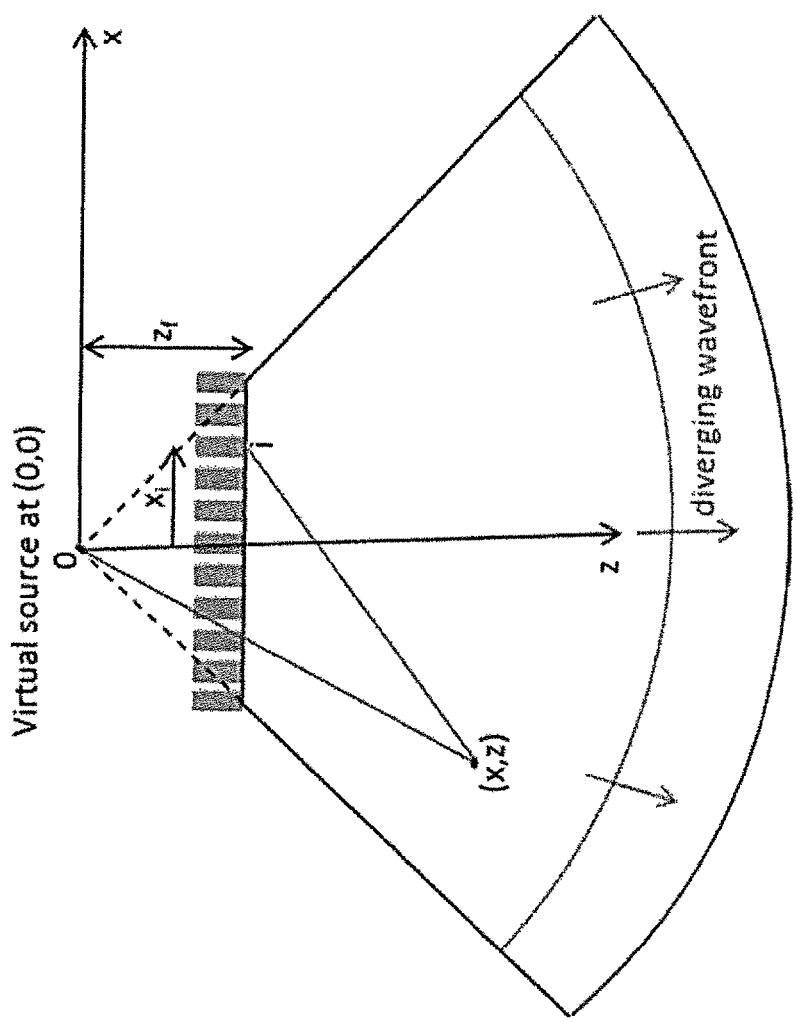
FIG. 18 illustrates additional details of the exemplary system of FIG. 17.

Referring now to FIG. 18, an unfocused diverging beam transmit was used to achieve a frame rate of 1200 fps at a depth of 90 mm. A virtual source was placed 6.5 mm behind the transducer, which corresponds to half the size of the active aperture, to send an unfocused beam with a diverging angle of 90°. The virtual source was centered relative to the transducer. The distance between the virtual source and each element of the transducer was computed in order to obtain the time delay to apply to each element to obtain a diverging wave. The 24 central elements had no apodization whereas the remaining 20 elements on each side had a weak apodization in transmit. Prior to in vivo application, the transmitted unfocused beam was characterized with a hydrophone (HGL-0200, ONDA, Sunnyvale, Calif., USA) in a water-filled tank. The hydrophone was set on a mechanical stage and the probe was attached to the wall of the tank. The hydrophone was moved along the lateral direction at three different axial depths (e.g., 2 mm, 50 mm and 90 mm) and a maximum pressure was obtained for each lateral position. Echocardiographic views of LA were acquired for each canine in the first example, and views of LA as well as RA and right ventricle (RV) in the region of the CTI were acquired for each human in the second example.

Figure 19:
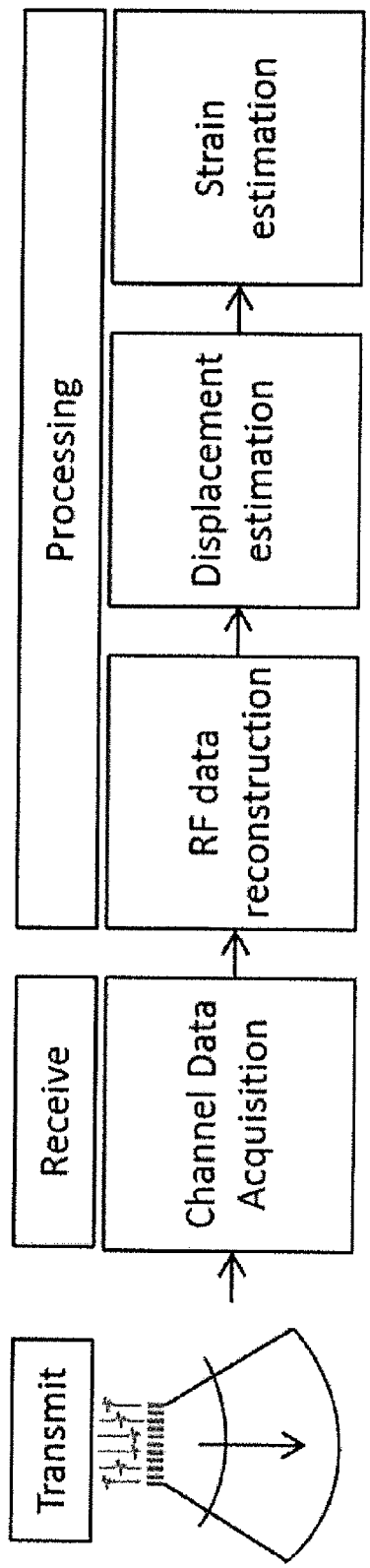
FIG. 19 illustrates exemplary techniques for intracardiac echocardiography (ICE) according to another aspect of the disclosed subject matter.

Referring now to FIG. 19, In-phase/Quadrature (IQ) data were acquired on all the 64 channels in parallel and stored in the system buffer. At 90-mm depth and 1200 fps, the buffer of the ultrasound system 200 stored up to 620 ms of IQ signals. B-mode images were acquired at 35 fps at the same location to help for structure identification. The data were transferred to a computer for off-line processing.

The RF signals were obtained from the IQ data and upsampled to 50 MHz to increase the quality of the motion estimation. The RF signals were then reconstructed using a standard delay-and-sum algorithm. That is, for purpose of illustration and not limitation, a grid of points onto which the RF signals can be reconstructed was defined in a polar coordinate system on a region of 90° field of view with 128 lines and depth of 90 mm with a radial grid step of 15.4 μm and which origin was the virtual source. The time of flight $T_f$ between the emission from the transducer and the reception on all the elements of the signals from every points of the grid was represented as:

$$T_f = T_t + T_r - T_d + T_b \quad (2)$$

where $$T_t = \frac{\sqrt{x^2 + z^2}}{c} \quad (3)$$

represented the time of flight from the virtual source to a point of the grid located at (x,z) and c represented the speed of sound, e.g., 1540 m·s$^{-1}$.

$$T_r = \frac{\sqrt{(x - x_i)^2 + (z - z_f)^2}}{c} \quad (4)$$

represented the time of flight from the pixel located at (x,z) to the i$^{th}$ element of the transducer located at $(x_i, z_f)$, and $$T_d = \frac{z_f}{c} \quad (5)$$

represented a time removed from $T_f$ to account for the beginning of acquisition when emitted from the center element located at $(0, z_f)$ and $T_b$ accounts for a bulk delay related to the ultrasound system and the propagation in the lens at the surface of the transducer, as shown for example in FIG. 18.

With continued reference to FIG. 19, the amplitude of each RF channel signal at each point of the grid was computed using 1-D linear interpolation. Receive focusing at each point of the grid was performed, for purpose of illustration and not limitation, by summing the interpolated amplitude of the RF channel signals across all the elements of the transducer. The reconstruction operation was performed on a GPU (Tesla C2075, NVIDIA, Santa Clara, Calif.) to increase the computation speed.

Figure 20B:
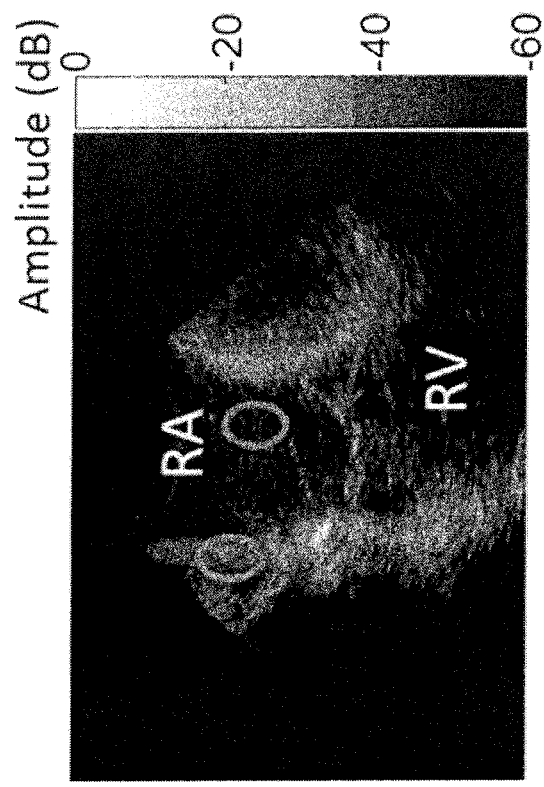
FIGS. 20(a)-20(b) are exemplary images illustrating further details of the techniques of FIG. 19.
Figure 20A:
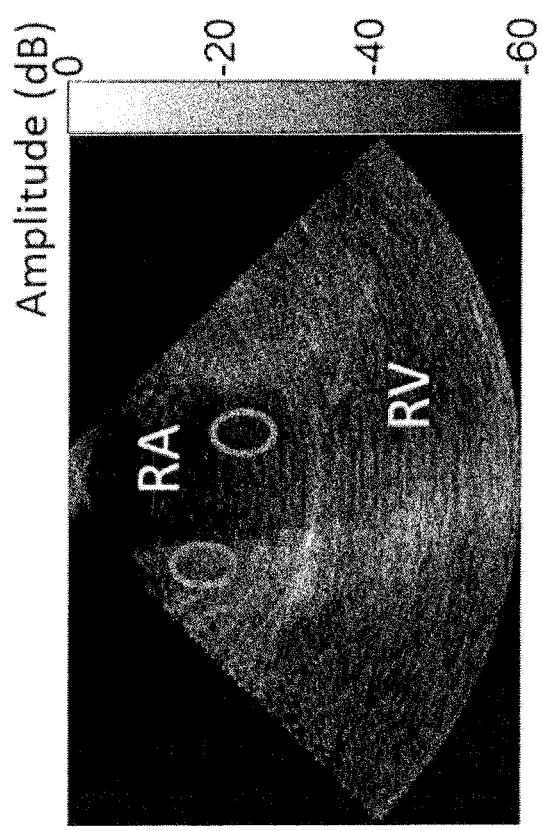

With reference to FIGS. 20(a)-20(b), a B-mode image was obtained from the reconstructed RF data by a Hilbert transform. Manual segmentation was performed to retrieve the myocardium. The conventional B-mode provided landmarks to assist the myocardial segmentation. The contrast-to-noise ratio (CNR) was computed for the reconstructed B-mode obtained from the diverging wave transmit and for the conventional B-mode for approximately the same view and same phase of the cardiac cycle. The CNR was represented as $$CNR = \frac{2(\mu_t - \mu_b)^2}{\sigma_t^2 + \sigma_b^2} \quad (6)$$

where $\mu t_t$ and $\mu t_b$ represented the mean of the amplitude inside the region of interest corresponding to the tissue and to the background, respectively, and $\sigma_t$ and $\sigma_b$ represented the standard deviation of the amplitude inside the region of interest corresponding to the tissue and to the background, respectively.

Referring again to FIG. 19, for purpose of illustration and not limitation, displacement between two successive frames was estimated by normalized 1-D cross-correlation with a window length of 10 wavelengths (2.7 mm) and 95% overlap. The displacements were integrated during atrial emptying (passive and active) to obtain the cumulative displacements. The relative myocardial wall displacement was thus used as a surrogate to determine the emptying phase. Volume of the heart chamber decreased during emptying. Displacement images obtained at high temporal resolution can allow for identifying the beginning and the end of the inward motion. For LA imaging, the phase from maximal size to minimal size of the LA can include LA conduit (passive emptying) and/or contractile (active emptying) function. Although out-of-plane motion can affect the apparent size of the LA in the echocardiographic view, the LA maximum volume can correspond to the beginning of LA conduit, and LA minimum volume can correspond to the end of LA active emptying. Patients for which no clear inward motion was observed were not utilized. End-emptying atrial strain was represented as the strain accumulated from the beginning to the end of the atrial inward motion. End-diastole (systole) was represented as the frame in the cardiac cycle in which the cardiac dimension is the largest (smallest), respectively. The selection of the frames corresponding to emptying was performed using criteria such as myocardial wall relative displacement for the ablation and the non-ablation cases. For RA and RV imaging, the closure of the tricuspid valve was used as a reference for the phase selection. Cumulative axial strains were computed from cumulative axial displacements by applying a least-squares estimator with a kernel equal to 2 mm using a Savitzky-Golay filter to decrease the noise amplification due to gradient operation. For purpose of illustration, computation of axial strains are described herein. However, any suitable strains, including for example and without limitation, lateral strains can be determined using the techniques described herein. Additionally or alternatively, the techniques described herein can be utilized to measure strains in one, two or three dimensions, or any suitable number of dimensions.

Additionally, and as embodied herein, a region of interest of approximately the same size and location was selected in the lateral wall of each canine LA in the first example to compute the value of the cumulative axial strain at end atrial emptying. To compare before, during and after ablation in patients in the second example, strains were estimated approximately at the same location and approximately the same phase of the cardiac cycle and during the same rhythm (normal sinus rhythm, AF or atrial flutter) in a region of interest of approximately 5×5 mm$^2$. The size of the region of interest was chosen to be larger than the size of the tip of the ablation catheter due to heat diffusion as well as catheter movement during the ablation. Mean and standard deviation of the strain in the selected region of interest were computed. For the canine results in the first example or when comparing different groups (before, during and after) in the second example, the mean and standard deviation reported are computed across the individuals in the group.

Furthermore, and as embodied herein, for purpose of illustration and confirmation of the disclosed subject matter, ultrasound data were acquired twice with approximately one minute between each acquisition in the same echocardiographic view without moving the ICE catheter in two patients in the second example. For one patient, the LA was imaged, and for the other patient the RA and RV were imaged. In each patient, the ultrasound data were acquired before ablation and during sinus rhythm. End-emptying atrial strain were imaged and compared for both acquisitions in each patient.

As described herein, for purpose of illustration and confirmation of the disclosed subject matter, myocardial displacement and strain were imaged with ICE at 1200 fps using parallel beamforming in three canines and eight humans in vivo. The acquisition duration was less than the duration of a cardiac cycle. For each acquisition either the entire emptying or filling phase was obtained. The acquisition duration was also less than the duration of the ablation at a specific location. The ultrasound data were acquired during normal sinus rhythm, AF or atrial flutter. B-mode images were also acquired to assist myocardial segmentation. The CNR was computed for both the reconstructed B-mode obtained from a diverging wave imaging and for a conventional B-mode. The CNR for the reconstructed B-mode and the B-mode was 5.1 and 9.3 respectively.

Referring now to FIGS. 21(a)-21(g), axial displacement and strain were assessed in the first example in the LA from ICE acquisitions in LA short axis view of three canines during atrial emptying. As embodied herein, the ICE probe can be located in the RA and oriented towards the LA.

With reference to FIGS. 21(a)-21(c), axial displacements are illustrated at the end of LA emptying. Displacements in the lateral (anatomical) direction are indicated in the negative end of the scale, and displacements in the medial direction are indicated in the positive end of the scale. As such, and as embodied herein, the interatrial septum wall is detected moving in the lateral direction (negative) whereas the left lateral wall is moving in the medial direction (positive). A schematic indicating the LA wall displacements is shown for example in FIG. 21(g).

With reference to FIGS. 21(d)-21(f), the corresponding strains show that positive strain indicated at the positive end of the scale can occur in the lateral wall and the interatrial septum, and negative strain (e.g., circumferential shortening) can occur in the anterior and posterior walls. Similar displacement and strain patterns occurred for each of the three canines. The mean absolute axial cumulative strain at the atrial emptying phase in the selected region of interest in the lateral wall across the three canines was 15.8±12.1%, where 12.1% represents a variability among the three canines.

Referring now to FIGS. 22(a)-22(f), illustration and confirmation of the disclosed subject matter was performed in the second example in two patients before ablation in sinus rhythm. End atrial emptying strains for two consecutive acquisitions in two different patients are illustrated. With reference to FIGS. 22(a)-22(b), end LA emptying strain is illustrated for two consecutive acquisitions in Patient #1. With reference to FIGS. 22(d)-22(e), end RA emptying strain is illustrated for two consecutive acquisitions in Patient #2. A schematic of the LA displacement for Patient #1 in FIG. 22(c) and of RA and RV displacement for Patient #2 in FIG. 22(f) are shown. A similar strain pattern is obtained for both acquisitions in each patient. Although atrial strains are illustrated for example in FIGS. 22(a)-22(f), additionally or alternatively, any suitable strains, such as ventrical strains, can be determined using the techniques described herein.

Referring now to FIGS. 23(a)-23(e), as embodied herein, displacements and strains were estimated in the LA of AF patients before, during and after an RF ablation procedure. Cumulative axial displacement before ablation at end LA emptying for Patient #4 during atrial fibrillation is shown in FIG. 23(a). As embodied herein, the ICE probe was located in the RA and oriented towards the LA. During LA emptying, LA contracted inwards, as shown for example in the schematic diagram of FIG. 23(e). The corresponding strains at end LA emptying are shown for example in FIG. 23(b). In this view, radial thickening was observed in the anterior wall and end LA emptying absolute strain magnitude reached approximately 16.4±10.1%. Axial displacements during ablation in the LA of the same patient and for approximately the same cardiac phase and rhythm are shown for example in FIG. 23(c). As embodied herein, LA contracted inwards. The corresponding strains are shown for example in FIG. 23(d). The black ellipse indicates the region of ablation and the arrow identifies the ablation catheter. The absolute strain magnitude was lower, approximately 0.9±3.0%, in the region where ablation occurred which was less than prior to ablation. As embodied herein, the decrease in strain was observed in the region of ablation whereas the regions where no ablation was performed did not exhibit a significant change in strain. This decrease in strain can indicate that the contractility of the myocardium was reduced in the ablated region which indicates lesion formation. Although atrial strains are illustrated for example in FIGS. 23(a)-23(e), additionally or alternatively, any suitable strains, such as ventrical strains, can be determined using the techniques described herein.

Referring now to FIGS. 24(a)-24(e), as embodied herein, cumulative axial displacements and strains at RA end-emptying were evaluated in the CTI region of Patient #6 in sinus rhythm during and after RF ablation in this region. In this example, the ICE probe was located in the RA and oriented towards the right ventricle (RV). Axial displacements in the patient RA and RV during ablation were shown for example in FIG. 24(a). The RA and RV lateral walls moved in the superior direction as illustrated for example in the schematic diagram of FIG. 24(e). The corresponding strains are shown for example in FIG. 24(b). In this view, RA longitudinal shortening and RV longitudinal lengthening are shown for example in their respective lateral walls. The absolute strain magnitude in the RA lateral wall was approximately 43.0±18.1%. Axial displacements in the same patient RA and RV in the CTI region after ablation and during approximately the same cardiac phase are shown for example in FIG. 24(c). The RA and RV lateral walls moved in the superior direction. The corresponding strain is shown for example in FIG. 24(d) and was approximately 33.7±15.8% in the region of ablation, which was less than prior to ablation. Additionally, and as embodied herein, the strain magnitude in the ablated region decreased on the endocardial side of the myocardium more than on the epicardial side, which can indicate that the transmurality of the lesion can be imaged using the techniques described herein. Although atrial strains are illustrated for example in FIGS. 24(a)-24(e), additionally or alternatively, any suitable strains, such as ventrical strains, can be determined using the techniques described herein.

Figures 25A, 25B, 25C:
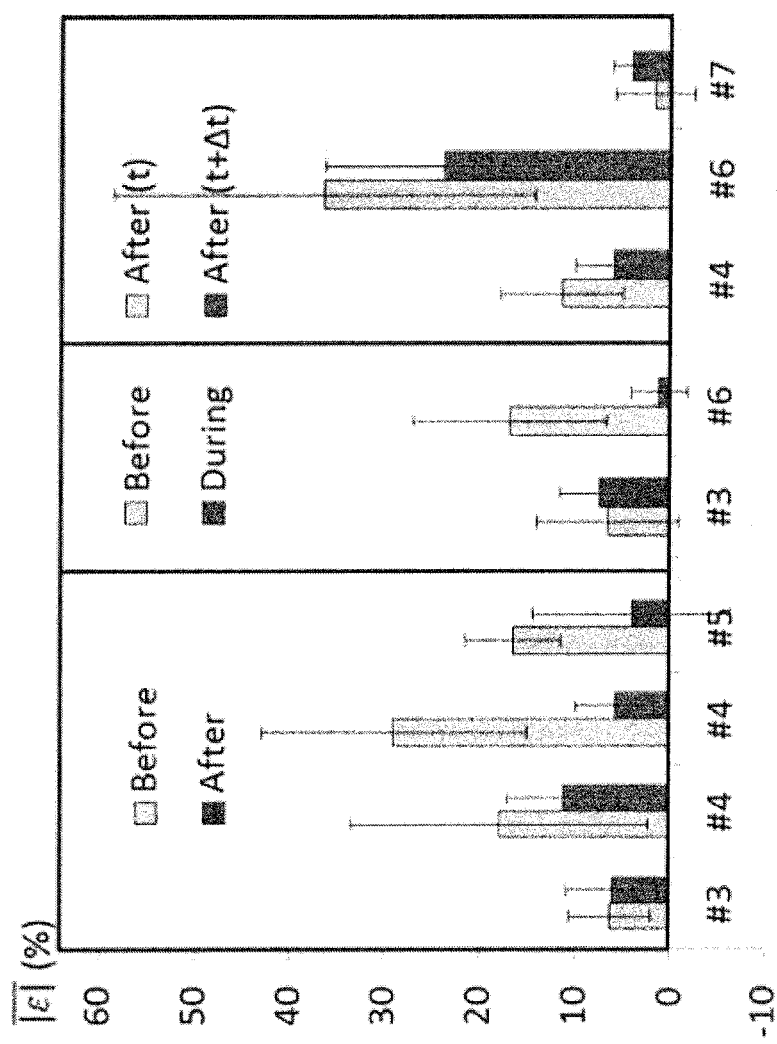
FIGS. 25(a)-25(c) are diagrams illustrating further details of the techniques of FIG. 19.

Referring now to FIGS. 25(a)-25(c), as embodied herein, the strain variation at the different stages of the ablation for all patients is illustrated. For purpose of illustration and not limitation, as embodied herein, error bars represent standard deviation in the selected region of interest corresponding to the region of ablation. Strain was compared before and after ablation for three patients and a total of four ultrasound views. Two ultrasound views were obtained for one of the three patients. The average absolute strain magnitude before ablation was 17.4±9.3% and decreased to 6.7±3.1% after ablation. Strain was also compared before and during ablation for two patients with one ultrasound view per patient. The average absolute value of strain magnitude was 11.3±7.2% before ablation and 4.0±4.4% during ablation. Strain after ablation at a certain time ($\varepsilon^t$) was also compared to strain after ablation later on ($\varepsilon^{t+\Delta t}$). The average absolute value of strain magnitude was 16.2±17.7% ablation at time t and 10.9±10.7% after ablation at time t+Δt.

For purpose of illustration and not limitation, as embodied herein, thermal lesions created by radio-frequency (RF) ablation of the heart can be characterized to provide real time assessment of lesions, which can include characterization of transmurality and gaps that can aid in long term success of an ablation procedure. Myocardial Elastography (ME), and other suitable ultrasound techniques, can be combined with intracardiac echocardiography (ICE) to provide information on the mechanical properties of tissues. For example, and as embodied herein, diverging wave imaging and parallel beamforming can be used with ICE to image myocardial strain at high temporal resolution during atrial emptying in vivo. Additionally or alternatively, and as embodied herein, differences in myocardial strains with ICE before, during and after radio-frequency ablation can be analyzed, for example and without limitation during a clinical ablation procedure.

For purpose of illustration and confirmation of the disclosed subject matter, diverging wave imaging was compared to that of B-mode imaging by comparing the contrast-to-noise ratio (CNR) using each technique. The CNR was found to be 5.1 for reconstructed B-mode and 9.3 for regular B-mode images. The regular B-mode images can have greater contrast, which can be due at least in part to focused transmit for each line, which can have improved lateral resolution. The acquisition of RF channel data for diverging wave imaging can allow for improved temporal resolution compared to regular B-mode imaging, and RF signals can provide improved performance over envelope signals. In the first example, as described herein, three canines were imaged to illustrate imaging of axial strain with ICE at high frame rate using diverging waves and to assess the performance of the ME technique with ICE. In the second example, eight patients undergoing RF ablation, which utilized ICE during ablation delivery in their left atrium and cavotricuspid isthmus (CTI), were investigated to illustrate feasibility of clinical application of the disclosed subject matter. The techniques described herein can be utilized, for purpose of illustration and not limitation, for assessment of lesion location induced by RF ablation during the ablation procedure to improve the efficiency of electrical isolation and conduction block to treat the arrhythmia as mechanical contraction at a region of the myocardium follows electrical activation of the same region.

In the first example, as described herein, ME was performed in the LA of three canines, as shown for example in FIGS. 21(a)-21(g). Axial displacements and strains were accumulated during LA emptying. The orientation of the ICE transducer relative to LA chamber allowed estimation in the radial (e.g., in septum and lateral regions) and circumferential (e.g., in anterior and posterior regions) directions. Strains at end LA emptying indicated radial thickening (positive scale) in the lateral wall and the interatrial septum, and circumferential shortening (negative scale) occurred in anterior and posterior region. Additionally, LA displacement showed that the interatrial septum wall moved in the lateral direction (negative scale), and the left lateral wall moved in the medial direction (positive scale). Similar axial strain pattern were found in each of the three canines. For purpose of illustration and not limitation, according to the disclosed subject matter, ME can be combined with ICE to indicate successful delivery of ablation lesions as demarcated by changes in tissue mechanics after ablation.

In the second example, as described herein, exemplary techniques for ICE with ME was performed in two patients before ablation in sinus rhythm. Similar end atrial emptying strain was obtained for two consecutive acquisitions in each patient, which indicates reproducibility of axial strain imaging using diverging wave with ICE. Additionally, as described herein, AF patients underwent ICE before, during and after RF ablation. Axial displacements and strains were obtained during LA or RA emptying. The average absolute value of strain at end atrial emptying was found to be lower after ablation (6.7±3.1%) than before (17.4±9.3%) in approximately the same region. The average value of strain after ablation was 2.6 times lower than before ablation. This decrease in strain can be due at least in part to local stiffening of the tissue caused by the thermal ablation. For another set of ultrasound views, average absolute value of strain at end atrial emptying was found to be lower during ablation (4.0±4.4%) than before (11.3±7.2%) in approximately the same region. The average value of strain during ablation was 2.8 times lower than before ablation. For another set of ultrasound views, strain after ablation at a certain time was compared to strain after ablation later on following with several ablations in between. The average absolute strain magnitude was 16.2±17.7% after ablation and 10.9±10.7% further after ablation. The average value of strain after ablation at time t+Δt was 1.5 times lower than after ablation at time t.

Additionally, and as embodied herein, with reference to FIGS. 24(*a*)-24(*e*), cumulative axial displacements and strains were obtained in the RA and RV regions during RA emptying during and after CTI ablation. In this view, only longitudinal displacements and strains in the lateral wall were estimated. At end atrial emptying, the RA and RV lateral walls moved in the superior direction. End-emptying atrial absolute strain was 43.0±18.1% during ablation and 33.7±15.8% after ablation.

As embodied herein, for purpose of illustration and not limitation, myocardial strain estimation using RF signals at high temporal resolution and high line density with ICE during a clinical ablation procedure was performed. As embodied herein, high temporal resolution can provide improved motion estimation, and thus improved strain quality, at least in part because it can be subjected to reduced decorrelation. Additionally or alternatively, atrial strain imaging can be used to characterize the mechanical properties of the atria transmurally as well as along the myocardium. In this manner, the efficacy of lesions to inhibit conduction can be assessed, and conduction recovery can be related to the non-transmurality and gap between lesions generated during ablation. The RF ablation procedure of AF can be initiated with pulmonary vein isolation and can include targeted sites for linear ablation, such as without limitation, the LA roof, the anterior and posterior walls or CTI in RA. As such, ability to characterize thermal lesions in these regions can improve the assessment of efficacy of lesion delivery. As described herein, strain can be estimated in LA and RA during ablation according to the disclosed subject matter. Exemplary techniques described herein can be applied to image the heart in different cardiac rhythms using images taken in normal sinus rhythm, AF and atrial flutter. A decrease in strain can be identified during and after ablation in the LA and the RA, which can indicate a change in tissue mechanics. LA strain during atrial relaxation and strain rate during atrial contraction can be lower in patients have undergone RF ablation of AF and can maintain sinus rhythm for 6 months follow-up than normal controls. The global left atrial strain in patients who have undergone RF ablation can be 2.4 times lower than in normal controls. Although not expressing the same quantity as the ratio determined herein, such a ratio can reflect a change of mechanical properties due at least in part to ablation as described herein. Such measurements can be due at least in part to atrial scarring and loss of atrial myocardial mass.

Additionally or alternatively, as embodied herein, patients remaining in sinus rhythm three months after RF ablation of AF can have increased strain in LA during emptying and diastole, and patients having recurrent AF after three months can have decreased strain in LA compared to before ablation. However, in certain techniques, atrial function in ablated patients can be measured after several months follow-up. As embodied herein, strains can be measured several minutes to hours before, during and after ablation.

In addition or as a further alternative, a change of acoustic radiation force can induce displacement of myocardial tissue with ICE during an RF ablation. Displacements in ablated sites can be reduced compared to displacement in unablated sites. ARFI-induced displacements in ablated sites can be 1.9 times lower than in unablated sites, which can be due at least in part to lesion formation in tissue pathology from RF ablation. As embodied herein, strain in the RF ablated region decreased. As such, ME when integrated with ICE can be used to guide the ablation by ascertaining myocardium mechanics as an indication of adequate ablation delivery.

For purpose of illustration and not limitation, as embodied herein, identification of the emptying phase can be obtained from the myocardial walls relative displacements. As such, the phase of the cardiac cycle can vary before, during and after ablation in a moving heart. In this manner, the inward motion during AF can be less clear than during sinus rhythm, which can indicate that AF can induce additional errors in the selection of the cardiac phase. The cardiac phase identification can have improved accuracy and consistency with ECG compared to assessment of wall displacement. Phase selection can be performed from the beginning to the end of the LA inward motion, and thus LA conduit and contractile function to end-emptying atrial strain and to the change in strain can have different relative contributions. Additionally or alternatively, synchronous acquisition and storage of the ECG with RF data can be performed.

Additionally, and as embodied herein, selection of the same region of interest before, during and after ablation on the diverging wave images and on the B-mode images can be performed manually by visually identifying landmarks such as the position of heart valve. As such, certain ultrasound views before, during and after ablation on the diverging wave images and on the B-mode images can include a mismatch on the selected region of interest. In this manner, strain can be indicated as higher during ablation than before ablation. As embodied herein, estimation can be performed on the axial component and thus can be angle-dependent. Additionally or alternatively, the comparison in strain can be performed before, during and after ablation on the selected ROIs. As embodied herein, the average value of strain after ablation was 2.6 times lower than before ablation, which can be due at least in part to the ablation than to the error due to incorrectly matched ROIs. When different ROIs are compared, different strain values can be obtained due at least in part to a strain inhomogeneity in the mechanical properties of the tissue and/or to the angle-dependency. The strain value can thus be under- or overestimated based at least in part on the inherent strain distribution in the tissue and/or on insonification angle relative to the orientation of the myocardial wall. Additionally or alternatively, radial thickening, circumferential and longitudinal shortening can occur during atrial systole. As such, when the axial direction is aligned with the radial direction, positive strain can be obtained, and negative strain can be obtained when the axial direction is aligned with the circumferential or longitudinal direction. In addition, or as a further alternative, angle-independency can be achieved by estimating the lateral displacement and strain to derive the angle-independent radial and circumferential strain.

Furthermore, and as embodied herein, high frame rate can be obtained with parallel beamforming using a diverging wave transmit sequence. One frame can be obtained from a single firing, which can yield a reduced lateral resolution. Spatial compounding of diverging waves can be used to increase the lateral resolution, which can result in reduced frame rate and increased decorrelation. As such, a trade-off between compounding and frame rate can be adjusted to improve elastographic signal-to-noise ratio.

Figure 26:
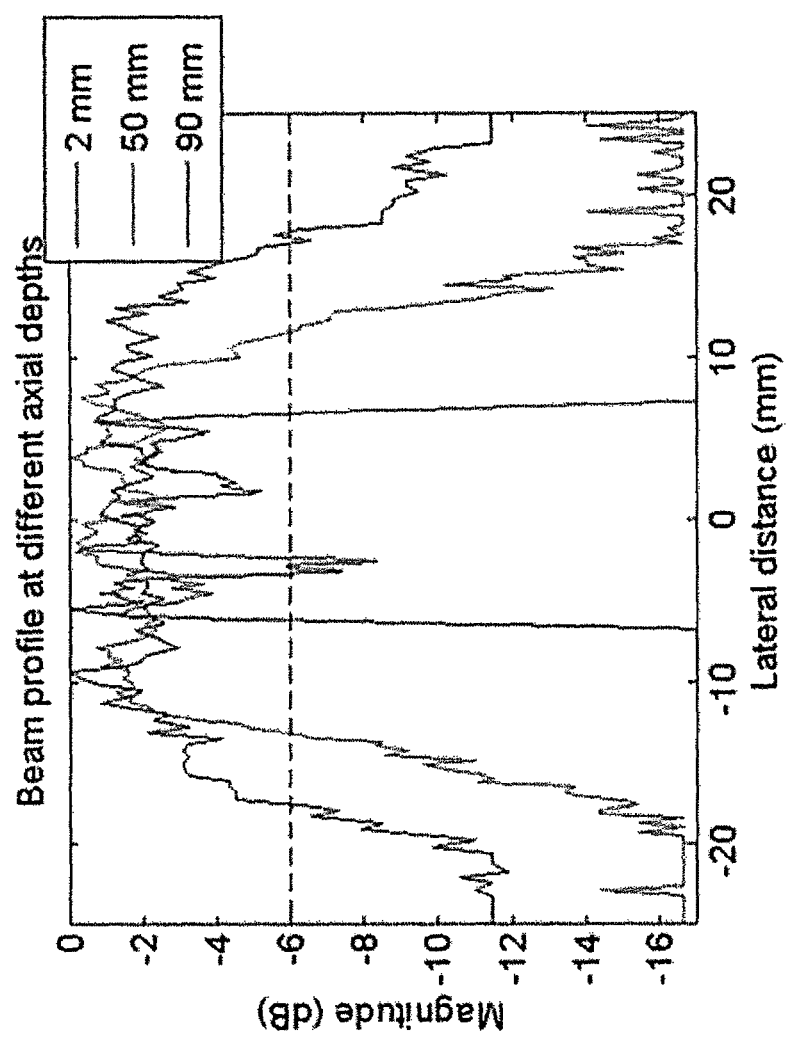
FIG. 26 is a diagram illustrating further details of the techniques of FIG. 19.

In addition, and as embodied herein, the pressure profile can be measured in the lateral direction, for example and without limitation at 90 mm axial depth, which can indicate a beamwidth of approximately 35 mm at −6 dB as shown for example in FIG. 26. The transmit sequence can be adjusted to yield a transmit beam with improved divergence to overcome any apodization on the lateral elements of the transducer. In this manner, accuracy of motion estimation, including on the outer regions, can be improved.

Furthermore, and as embodied herein, the techniques described herein were performed, for purpose of illustration and not limitation, on three canines without RF ablation in the first example and eight humans in vivo during a clinical RF ablation procedure in the second example. The results described herein thus illustration and confirm the disclosed subject matter, including clinical and laboratory incorporation of such imaging techniques. Such techniques can be applied, for example and without limitation, in other chambers of the heart, such as the right and left ventricle during VT ablation. Comparison of mechanical properties of the myocardium in ablated regions to lesion features that can be obtained with histology can also be performed.

As described herein, myocardial strains can be imaged with ICE at high temporal and high line density, including in vivo. The ablated regions in the human myocardium can have lower strains than before ablation. Myocardial elastography applied intracardially can be used to visualize thermal lesions during RF ablation.

The foregoing merely illustrates the principles of the disclosed subject matter. Various modifications and alterations to the described embodiments will be apparent to those skilled in the art in view of the teachings herein. It will thus be appreciated that those skilled in the art will be able to devise numerous techniques which, although not explicitly described herein, embody the principles of the disclosed subject matter and are thus within its spirit and scope.

The invention claimed is:

1. An imaging system for mapping behavior of a heart, comprising:
   an imaging device configured to acquire a series of two or more images of the heart over a period at one or more pixel locations, each pixel location corresponding to a region of the heart; and
   an image processor, coupled to the imaging device, configured to:
      obtain image data of the one or more pixel locations during the-period,
      measure a periodicity of the image data for each of the one or more pixel locations over the series of images, wherein the periodicity corresponds to an electromechanical signal of the heart in the region corresponding to the measured one or more pixel locations, and
      analyze the electromechanical signal to determine one or more patterns characteristic of an arrhythmia,
      determine a source or a type of the arrhythmia based on the one or more patterns determined from the electromechanical signal, wherein the arrhythmia comprises at least one of a focal arrhythmia, a reentrant arrhythmia, and atrial flutter, and
      if the one or more patterns determined from the electromechanical signal indicates the arrhythmia is the focal arrhythmia, identifying a location of a focal zone and a subsequent propagation of cardiac activation;
      if the one or more patterns determined from the electromechanical signal indicates the arrhythmia is the reentrant arrhythmia, perform a Fourier analysis on the electromechanical signal to determine a cycle length and one or more propagation patterns; and
      if the one or more patterns determined from the electromechanical signal indicates the atrial flutter, analyze strain images of the heart to identify an anatomic structure and guide ablation to treat the arrhythmia.

2. The imaging system of claim 1, wherein the image processor is configured to measure the periodicity of the image data by measuring a peak frequency of the image data for each of the one or more pixel locations, the image processor being further configured to determine a peak cycle length from each peak frequency, the peak cycle length corresponding to an electrical cycle length of the electromechanical signal of the heart in the region corresponding to the measured one or more pixel locations.

3. The imaging system of claim 2, wherein the image processor is further configured to measure a phase associated with each peak frequency, the phase corresponding to a direction of propagation of the electromechanical signal in the heart.

4. The imaging system of claim 1, wherein the image processor is further configured to measure the periodicity by measuring a crossing of a threshold of the image data for each of the one or more pixel locations.

5. The imaging system of claim 4, wherein the threshold corresponds to a condition of zero strain at the region of the heart corresponding to the one or more pixel locations.

6. The imaging system of claim 1, wherein the image processor is further configured to measure the periodicity by performing a Fourier transform of the image data for each of the one or more pixel locations.

7. The imaging system of claim 1, wherein the image data comprises an intensity of each of the one or more pixel locations.

8. The imaging system of claim 1, wherein the imaging device comprises an ultrasound transducer.

9. The imaging system of claim 1, wherein the image data comprises first image data corresponding to one or more first pixel locations corresponding to a first region of the heart and second image data corresponding to one or more second pixel locations corresponding to a second region of the heart, and the image processor is further configured to compare a first periodicity corresponding to the first region and a second periodicity corresponding to the second region.

10. The imaging system of claim 9, wherein the image processor is further configured to compare a first phase associated with the first periodicity and a second phase associated with the second periodicity, and compare the first phase with the second phase to determine a direction of propagation of the electromechanical signal in the heart.

11. The imaging system of claim 10, wherein the first region of the heart comprises at least a portion of the right atrium and the second region of the heart comprises at least a portion of the left atrium or ventricles.

12. The imaging system of claim 1, wherein the imaging processor is configured to determine the type of the arrhythmia.

13. The imaging system of claim 12, wherein the imaging processor is further configured to estimate a likelihood of success of a treatment for the arrhythmia.

14. The imaging system of claim 13, wherein the treatment comprises ablation or cardioversion.

15. The imaging system of claim 1, wherein the image processor is further configured to analyze the electromechanical signal by identifying a first zero-crossing of a strain characteristic over time determined based on the electromechanical signal.

16. The imaging system of claim 1, wherein the imaging device is further configured to acquire the strain images using an intracardiac echocardiography catheter in communication with the imaging device.

17. A method for planning and monitoring treatment of an arrhythmia in a heart, comprising:

acquiring a series of two or more images of the heart over a period, the series of images taken at one or more pixel locations, each pixel location corresponding to a region of the heart;

obtaining image data corresponding to the one or more pixel locations during the period;

measuring, by an image processor, a periodicity of the image data for each of the one or more pixel locations over the series of images, wherein the periodicity corresponds to an electromechanical signal of the heart in the region corresponding to the measured one or more pixel locations;

analyzing the electromechanical signal to determine one or more patterns characteristic of the arrhythmia;

determining a source or a type of the arrhythmia based on the one or more patterns determined from the electromechanical signal, wherein the arrhythmia comprises at least one of a focal arrhythmia, a reentrant arrhythmia, and atrial flutter, and if the one or more patterns determined from the electromechanical signal indicates the arrhythmia is the focal arrhythmia, identifying a location of a focal zone and a subsequent propagation of cardiac activation;

if the one or more patterns determined from the electromechanical signal indicates the arrhythmia is the reentrant arrhythmia, performing a Fourier analysis on the electromechanical signal to determine a cycle length and one or more propagation patterns; and if the one or more patterns determined from the electromechanical signal indicates the atrial flutter, imaging the heart to identify an anatomic structure and guide ablation to treat the arrhythmia.

18. The method of claim 17, further comprising performing the ablation, wherein the ablation comprises radio-frequency ablation, the method further comprising measuring myocardial strains and differences between the myocardial strains before or after the radio-frequency ablation.

19. The method of claim 17, wherein analyzing the electromechanical signal includes identifying a first zero-crossing of a strain characteristic over time determined based on the electromechanical signal.

20. The method of claim 17, wherein imaging the heart comprises acquiring strain images of the heart using an intracardiac echocardiography catheter.

21. The method of claim 17, wherein measuring the periodicity of the image data comprises measuring a peak frequency of the image data for each of the one or more pixel locations, the method further comprising determining a peak cycle length from each peak frequency, the peak cycle length corresponding to an electrical cycle length of the electromechanical signal of the heart in the region corresponding to the measured one or more pixel locations.

22. The method of claim 21, further comprising measuring a phase associated with each peak frequency, the phase corresponding to a direction of propagation of the electromechanical signal in the heart.

23. The method of claim 17, wherein measuring the periodicity comprises measuring a crossing of a threshold of the image data for each of the one or more pixel locations.

24. The method of claim 23, wherein the threshold corresponds to a condition of zero strain at the region of the heart corresponding to the one or more pixel locations.

25. The method of claim 17, wherein measuring the periodicity comprises performing a Fourier transform of the image data for each of the one or more pixel locations.

26. The method of claim 17, wherein the image data comprises first image data corresponding to one or more first pixel locations corresponding to a first region of the heart and second image data corresponding to one or more second pixel locations corresponding to a second region of the heart, the method further comprising comparing a first periodicity corresponding to the first region and a second periodicity corresponding to the second region.

27. The method of claim 26, further comprising measuring a first phase associated with the first periodicity and a second phase associated with the second periodicity, and comparing the first phase with the second phase to determine a direction of propagation of the electromechanical signal in the heart.

28. The method of claim 27, wherein the first region of the heart comprises at least a portion of the right atrium and the second region of the heart comprises at least a portion of the left atrium or ventricles.

29. The method of claim 17, further comprising, determining a type of arrhythmia based on the one or more patterns determined from the electromechanical signal.

30. The method of claim 29, further comprising, estimating a likelihood of success of a treatment for the arrhythmia.

31. The method of claim 30, wherein the treatment comprises ablation or cardioversion.

\* \* \* \* \*